US011202759B2

(12) United States Patent
Huebsch et al.

(10) Patent No.: US 11,202,759 B2
(45) Date of Patent: Dec. 21, 2021

(54) INJECTABLE, PORE-FORMING HYDROGELS FOR MATERIALS-BASED CELL THERAPIES

(75) Inventors: Nathaniel D. Huebsch, Colma, CA (US); Christopher M. Madl, Vestal, NY (US); Kangwon Lee, Lexington, MA (US); Maria M. Xu, Morgantown, WV (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/877,572

(22) PCT Filed: Oct. 6, 2011

(86) PCT No.: PCT/US2011/055174
§ 371 (c)(1),
(2), (4) Date: Nov. 19, 2013

(87) PCT Pub. No.: WO2012/048165
PCT Pub. Date: Apr. 12, 2012

(65) Prior Publication Data
US 2014/0079752 A1    Mar. 20, 2014

Related U.S. Application Data

(60) Provisional application No. 61/390,594, filed on Oct. 6, 2010.

(51) Int. Cl.
| | |
|---|---|
| *A61L 27/20* | (2006.01) |
| *A61L 27/22* | (2006.01) |
| *A61L 27/26* | (2006.01) |
| *A61L 27/38* | (2006.01) |
| *A61L 27/54* | (2006.01) |
| *A61L 27/56* | (2006.01) |
| *A61L 27/58* | (2006.01) |
| *A61L 27/52* | (2006.01) |
| *A61L 27/48* | (2006.01) |
| *A61K 9/16* | (2006.01) |

(52) U.S. Cl.
CPC ............ *A61K 9/1652* (2013.01); *A61L 27/20* (2013.01); *A61L 27/26* (2013.01); *A61L 27/38* (2013.01); *A61L 27/48* (2013.01); *A61L 27/52* (2013.01); *A61L 27/54* (2013.01); *A61L 27/56* (2013.01); *A61L 27/58* (2013.01); *A61L 2300/414* (2013.01); *A61L 2400/06* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,160,084 A | 12/2000 | Langer et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 * | 11/2003 | Mooney .................. A61L 27/20 536/3 |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |

(Continued)

FOREIGN PATENT DOCUMENTS

| | | |
|---|---|---|
| AU | 2018201930 A1 | 4/2018 |
| CN | 1757662 A | 4/2006 |

(Continued)

OTHER PUBLICATIONS

Holland et al., Journal of Controlled Release, vol. 94, pp. 101-114; 2004.*
Vieira et al. Biomacromolecules, vol. 9, pp. 1195-1199 (2008).*
Fischbach et al., Advances in Polymer Science, vol. 203, pp. 191-221 (2006).*
Annabi et al., Tissue Engineering: Part B, vol. 16, No. 4, pp. 371-383 (electonically published Mar. 17, 2010).*
Annabi et al., Tissue Engineering: Part B, vol. 16, No. 4, pp. 371-383; electonically published Mar. 17, 2010 (of record).*
Bouhadir et al., Biotechnology Progress, vol. 17, pp. 945-950; 2001 (of record).*
Boontheekul et al., Biomaterials, vol. 26, pp. 2455-2465; 2005 (of record).*

(Continued)

*Primary Examiner* — Soren Harward
*Assistant Examiner* — Paul D Pyla
(74) *Attorney, Agent, or Firm* — McCarter & English, LLP; Maria Laccotripe Zacharakis; Maneesh Gulati

(57) ABSTRACT

The invention provides compositions and methods to form pores in situ within hydrogels following hydrogel injection. Pores formed in situ via degradation of sacrificial porogens within the surrounding hydrogel facilitate recruitment or release of cells. Disclosed herein is a material that is not initially porous, but which becomes macroporous over time.

50 Claims, 20 Drawing Sheets

Specification includes a Sequence Listing.

(56) References Cited

U.S. PATENT DOCUMENTS

| | | |
|---|---|---|
| 6,797,738 B2 | 9/2004 | Harris et al. |
| 6,800,733 B2 | 10/2004 | Tsien et al. |
| 6,858,222 B2 | 2/2005 | Nelson et al. |
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,410,953 B2 | 8/2008 | Kawasaki |
| 7,427,602 B1 | 9/2008 | Shea et al. |
| 7,569,850 B2 | 8/2009 | Noy et al. |
| 7,575,759 B2 | 8/2009 | Murphy et al. |
| 7,592,326 B2 | 9/2009 | Karaolis |
| 7,687,241 B2 | 3/2010 | Chen |
| 7,709,458 B2 | 5/2010 | Karaolis et al. |
| 7,790,699 B2 | 9/2010 | Melvik et al. |
| 8,067,237 B2 | 11/2011 | Mooney et al. |
| 8,188,058 B2 | 5/2012 | Hackam et al. |
| 8,273,373 B2 | 9/2012 | Alsberg et al. |
| 8,354,119 B2 | 1/2013 | Geistlich et al. |
| 8,367,628 B2 | 2/2013 | Goodwin et al. |
| 8,535,719 B2 | 9/2013 | Badylak et al. |
| 8,709,464 B2 | 4/2014 | Ma et al. |
| 8,728,456 B2 | 5/2014 | Sands et al. |
| 8,883,308 B2 | 11/2014 | Polshettiwar et al. |
| 8,932,583 B2 | 1/2015 | Mooney et al. |
| 9,012,399 B2 | 4/2015 | Cao et al. |
| 9,132,210 B2 | 9/2015 | Mooney et al. |
| 9,139,809 B2 | 9/2015 | Porcelli et al. |
| 9,150,631 B2 | 10/2015 | Super et al. |
| 9,370,558 B2 | 6/2016 | Ali et al. |
| 9,381,235 B2 | 7/2016 | Sands et al. |
| 9,446,107 B2 | 9/2016 | Mooney et al. |
| 9,486,512 B2 | 11/2016 | Kim et al. |
| 9,591,360 B2 | 3/2017 | Jennings et al. |
| 9,675,561 B2 | 6/2017 | Bencherif et al. |
| 9,770,535 B2 | 9/2017 | Mooney et al. |
| 9,821,045 B2 | 11/2017 | Ali et al. |
| 9,937,249 B2 | 4/2018 | Kim et al. |
| 10,045,947 B2 | 8/2018 | Bencherif et al. |
| 10,080,789 B2 | 9/2018 | Sands et al. |
| 10,137,184 B2 | 11/2018 | Mooney et al. |
| 10,149,897 B2 | 12/2018 | Mooney et al. |
| 2002/0045672 A1 | 4/2002 | Harris et al. |
| 2002/0131853 A1 | 9/2002 | Nagasawa |
| 2002/0131953 A1 | 9/2002 | Takashima et al. |
| 2002/0150604 A1 | 10/2002 | Yi et al. |
| 2003/0075822 A1 | 4/2003 | Slivka et al. |
| 2003/0082806 A1 | 5/2003 | Berenson et al. |
| 2003/0095994 A1 | 5/2003 | Geistlich et al. |
| 2003/0100527 A1 | 5/2003 | Krieg et al. |
| 2003/0194397 A1 | 10/2003 | Mishra |
| 2003/0232895 A1 | 12/2003 | Omidian et al. |
| 2004/0028745 A1 | 2/2004 | Bouhadir et al. |
| 2004/0043034 A1 | 3/2004 | Jensenius et al. |
| 2004/0058883 A1 | 3/2004 | Phillips et al. |
| 2004/0063206 A1 | 4/2004 | Rowley et al. |
| 2004/0136968 A1 | 7/2004 | Zheng et al. |
| 2004/0151764 A1 | 8/2004 | Zamora |
| 2004/0213795 A1 | 10/2004 | Collins et al. |
| 2004/0220111 A1 | 11/2004 | Kleinman et al. |
| 2004/0228858 A1 | 11/2004 | Hanson et al. |
| 2004/0242469 A1 | 12/2004 | Lee et al. |
| 2004/0242482 A1 | 12/2004 | Gehring et al. |
| 2005/0002915 A1 | 1/2005 | Atala et al. |
| 2005/0037330 A1 | 2/2005 | Fischer et al. |
| 2005/0053667 A1 | 3/2005 | Irvine et al. |
| 2005/0079159 A1 | 4/2005 | Shastri et al. |
| 2005/0090008 A1 | 4/2005 | Segura et al. |
| 2005/0106211 A1 | 5/2005 | Nelson et al. |
| 2005/0154376 A1 | 7/2005 | Riviere et al. |
| 2005/0177249 A1 | 8/2005 | Kladakis et al. |
| 2005/0202394 A1 | 9/2005 | Dobson |
| 2006/0083712 A1 | 4/2006 | Anversa |
| 2006/0141018 A1 | 6/2006 | Cochrum et al. |
| 2006/0264380 A1 | 11/2006 | Hellstrom et al. |
| 2006/0292134 A1 | 12/2006 | Stohs |
| 2007/0003595 A1 | 1/2007 | Wang et al. |
| 2007/0020232 A1 | 1/2007 | Rossignol et al. |
| 2007/0026518 A1 | 2/2007 | Healy et al. |
| 2007/0081972 A1 | 4/2007 | Sandler et al. |
| 2007/0116680 A1 | 5/2007 | Stegemann et al. |
| 2007/0178159 A1 | 8/2007 | Chen et al. |
| 2007/0190646 A1 | 8/2007 | Engler et al. |
| 2008/0044900 A1 | 2/2008 | Mooney et al. |
| 2008/0044990 A1 | 2/2008 | Lee |
| 2008/0051490 A1 | 2/2008 | Williams et al. |
| 2008/0113929 A1 | 5/2008 | Lipford et al. |
| 2008/0138416 A1 | 6/2008 | Rauh et al. |
| 2008/0152624 A1 | 6/2008 | Paludan et al. |
| 2008/0206308 A1 | 8/2008 | Jabbari et al. |
| 2008/0233181 A1 | 9/2008 | Nagy et al. |
| 2008/0268019 A1 | 10/2008 | Badylak et al. |
| 2008/0268052 A1 | 10/2008 | Voytik-Harbin et al. |
| 2009/0017096 A1 | 1/2009 | Lowman et al. |
| 2009/0061014 A1 | 3/2009 | Messersmith et al. |
| 2009/0192079 A1 | 7/2009 | Santos et al. |
| 2009/0238853 A1 | 9/2009 | Liu et al. |
| 2009/0252752 A1 | 10/2009 | Tahara et al. |
| 2009/0297579 A1 | 12/2009 | Semino et al. |
| 2009/0305983 A1 | 12/2009 | Ying et al. |
| 2010/0015709 A1 | 1/2010 | Rehfeldt et al. |
| 2010/0055102 A1 | 3/2010 | Langermann |
| 2010/0055186 A1 | 3/2010 | Dadsetan et al. |
| 2010/0080816 A1 | 4/2010 | Hadeiba et al. |
| 2010/0129422 A1 | 5/2010 | Han et al. |
| 2010/0159008 A1 | 6/2010 | Barron et al. |
| 2010/0189760 A1 | 7/2010 | Schaffer et al. |
| 2010/0190741 A1 | 7/2010 | Cohen et al. |
| 2010/0272771 A1 | 10/2010 | Harlow et al. |
| 2011/0008443 A1 | 1/2011 | Alsberg et al. |
| 2011/0020216 A1 | 1/2011 | Mooney et al. |
| 2011/0117170 A1 | 5/2011 | Cao et al. |
| 2011/0207166 A1 | 8/2011 | Vaiselbuh |
| 2011/0223255 A1 | 9/2011 | Thiesen et al. |
| 2011/0253643 A1 | 10/2011 | Polshettiwar et al. |
| 2011/0256184 A1 | 10/2011 | Lei et al. |
| 2011/0300186 A1 | 12/2011 | Hellstrom et al. |
| 2012/0100182 A1 | 4/2012 | Mooney et al. |
| 2012/0121539 A1 | 5/2012 | Sands et al. |
| 2012/0122218 A1 | 5/2012 | Huebsch et al. |
| 2012/0134967 A1 | 5/2012 | Mooney et al. |
| 2012/0256336 A1 | 10/2012 | Yano et al. |
| 2012/0264599 A1 | 10/2012 | Komatsu et al. |
| 2012/0294888 A1 | 11/2012 | Kishimoto et al. |
| 2012/0329791 A1 | 12/2012 | Ashwell et al. |
| 2013/0029030 A1 | 1/2013 | Larsen |
| 2013/0035283 A1 | 2/2013 | Super et al. |
| 2013/0045246 A1 | 2/2013 | Edwards et al. |
| 2013/0052117 A1 | 2/2013 | Imai et al. |
| 2013/0072547 A1 | 3/2013 | Hackam et al. |
| 2013/0145488 A1 | 6/2013 | Wang et al. |
| 2013/0177536 A1 | 7/2013 | Mooney et al. |
| 2013/0202707 A1 | 8/2013 | Ali et al. |
| 2013/0302396 A1 | 11/2013 | Mooney et al. |
| 2013/0331343 A1 | 12/2013 | Cao et al. |
| 2014/0072510 A1 | 3/2014 | Shea et al. |
| 2014/0112990 A1 | 4/2014 | Bencherif et al. |
| 2014/0178964 A1 | 6/2014 | Mooney et al. |
| 2014/0193488 A1 | 7/2014 | Kim et al. |
| 2014/0205653 A1 | 7/2014 | Dubensky, Jr. et al. |
| 2014/0227327 A1 | 8/2014 | Bencherif et al. |
| 2014/0227723 A1 | 8/2014 | Ingber et al. |
| 2014/0234423 A1 | 8/2014 | Sands et al. |
| 2015/0024026 A1 | 1/2015 | Mooney et al. |
| 2015/0030669 A1 | 1/2015 | Platscher et al. |
| 2015/0072009 A1 | 3/2015 | Kim et al. |
| 2015/0359928 A1 | 12/2015 | Gu et al. |
| 2015/0366956 A1 | 12/2015 | Mooney et al. |
| 2016/0033511 A1 | 2/2016 | Pannell et al. |
| 2016/0220667 A1 | 8/2016 | Mooney et al. |
| 2016/0220668 A1 | 8/2016 | Mooney et al. |
| 2016/0228543 A1 | 8/2016 | Mooney et al. |

(56) References Cited

U.S. PATENT DOCUMENTS

| | | |
|---|---|---|
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0182138 A1 | 6/2017 | Kim et al. |
| 2017/0246281 A1 | 8/2017 | Super et al. |
| 2017/0362307 A1 | 12/2017 | Ingber et al. |
| 2018/0021253 A1 | 1/2018 | Sandeep et al. |
| 2018/0117171 A1 | 5/2018 | Mooney et al. |
| 2018/0164298 A1 | 6/2018 | Ali et al. |
| 2018/0243231 A1 | 8/2018 | Bencherif et al. |
| 2018/0289789 A1 | 10/2018 | Ali et al. |
| 2018/0320157 A1 | 11/2018 | Super et al. |
| 2018/0344821 A1 | 12/2018 | Kim et al. |
| 2018/0371058 A1 | 12/2018 | Watters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |
| 2019/0292517 A1 | 9/2019 | Cheung et al. |

FOREIGN PATENT DOCUMENTS

| | | | |
|---|---|---|---|
| CN | 101655611 A | 2/2010 | |
| EP | 0562862 A1 | 9/1993 | |
| EP | 1452191 A2 | 9/2004 | |
| EP | 1561481 A2 | 8/2005 | |
| EP | 1712238 A1 | 10/2006 | |
| EP | 1975230 A1 | 10/2008 | |
| JP | 2000503884 A | 4/2000 | |
| JP | 2001-524136 A | 11/2001 | |
| JP | 2003506401 A | 2/2003 | |
| JP | 2003180815 A | 7/2003 | |
| JP | 2004-159849 A | 6/2004 | |
| JP | 2004520043 A | 7/2004 | |
| JP | 2005160669 A | 6/2005 | |
| JP | 2005170816 A | 6/2005 | |
| JP | 2005528401 A | 9/2005 | |
| JP | 2007500673 A | 1/2007 | |
| JP | 2007-505827 A | 3/2007 | |
| JP | 2007503881 A | 3/2007 | |
| JP | 2007528848 A | 10/2007 | |
| JP | 2008515503 A | 5/2008 | |
| JP | 2008528114 A | 7/2008 | |
| JP | 2009519042 A | 5/2009 | |
| JP | 2009521406 A | 6/2009 | |
| JP | 2009540921 A | 11/2009 | |
| JP | 2010502824 A | 1/2010 | |
| JP | 2010508976 A | 3/2010 | |
| JP | 2010-227012 A | 10/2010 | |
| JP | 2011-511834 A | 4/2011 | |
| JP | 2011511684 A | 4/2011 | |
| JP | 2013-531043 A | 8/2013 | |
| WO | WO-1996/02555 A1 | 2/1996 | |
| WO | WO-9616086 A1 | 5/1996 | |
| WO | WO-98012228 A1 | 3/1998 | |
| WO | WO-9816266 A1 | 4/1998 | |
| WO | WO-1999/44583 A2 | 9/1999 | |
| WO | WO-9951259 A2 | 10/1999 | |
| WO | WO-2000050006 A2 | 8/2000 | |
| WO | WO-2001/10421 A1 | 2/2001 | |
| WO | WO-2001/37810 A2 | 5/2001 | |
| WO | WO-0135932 A2 | 5/2001 | |
| WO | WO-0216557 A2 | 2/2002 | |
| WO | WO-200240071 A1 | 5/2002 | |
| WO | WO-02058723 A2 | 8/2002 | |
| WO | WO-2002/092054 A2 | 11/2002 | |
| WO | WO-2003/020161 A2 | 3/2003 | |
| WO | WO-03020884 A2 | 3/2003 | |
| WO | WO-2003/088905 A2 | 10/2003 | |
| WO | WO-04006990 A2 | 1/2004 | |
| WO | WO-04030706 A2 | 4/2004 | |
| WO | WO-2004029230 A2 | 4/2004 | |
| WO | WO-2004031371 A2 | 4/2004 | |
| WO | WO-04089413 A1 | 10/2004 | |
| WO | WO-05013896 A2 | 2/2005 | |
| WO | WO-05013933 A1 | 2/2005 | |
| WO | WO-2005/025614 A2 | 3/2005 | |
| WO | WO-05026318 A2 | 3/2005 | |
| WO | WO-2005020849 A2 | 3/2005 | |
| WO | WO-05037190 A2 | 4/2005 | |
| WO | WO-05037293 A1 | 4/2005 | |
| WO | WO-05046748 A1 | 5/2005 | |
| WO | WO-05072088 A2 | 8/2005 | |
| WO | WO-2005/104755 A2 | 11/2005 | |
| WO | WO-2006/039045 A2 | 4/2006 | |
| WO | WO-2006040128 A1 | 4/2006 | |
| WO | WO-2006078987 A2 | 7/2006 | |
| WO | WO-2006/113407 A2 | 10/2006 | |
| WO | WO-06119619 A1 | 11/2006 | |
| WO | WO-06136905 A2 | 12/2006 | |
| WO | 2007/001332 A2 | 1/2007 | |
| WO | WO-07030901 A1 | 3/2007 | |
| WO | WO-2007/039150 A2 | 4/2007 | |
| WO | WO-2007/042554 A2 | 4/2007 | |
| WO | 2007/051120 A2 | 5/2007 | |
| WO | 2007/068489 A2 | 6/2007 | |
| WO | WO-07063075 A1 | 6/2007 | |
| WO | WO-07064152 A1 | 6/2007 | |
| WO | WO-07070660 A2 | 6/2007 | |
| WO | WO-07078196 A1 | 7/2007 | |
| WO | WO-2007/087585 A1 | 8/2007 | |
| WO | WO-2007/089870 A2 | 8/2007 | |
| WO | WO-07107739 A1 | 9/2007 | |
| WO | WO-2007/149161 A2 | 12/2007 | |
| WO | WO-07150020 A1 | 12/2007 | |
| WO | WO-2008/008266 A2 | 1/2008 | |
| WO | WO-08018707 A1 | 2/2008 | |
| WO | WO-2008031525 A1 | 3/2008 | |
| WO | WO-2008/043157 A1 | 4/2008 | |
| WO | WO-2008/057600 A2 | 5/2008 | |
| WO | WO-08109852 A2 | 9/2008 | |
| WO | WO-08114149 A2 | 9/2008 | |
| WO | WO-08148761 A1 | 12/2008 | |
| WO | WO-08157394 A2 | 12/2008 | |
| WO | WO-09002401 A2 | 12/2008 | |
| WO | WO-09005769 A2 | 1/2009 | |
| WO | 2009/024775 A1 | 2/2009 | |
| WO | WO-09018500 A1 | 2/2009 | |
| WO | WO-09072767 A2 | 6/2009 | |
| WO | WO-09074341 A1 | 6/2009 | |
| WO | WO-2009/100716 A2 | 8/2009 | |
| WO | WO-09102465 A2 | 8/2009 | |
| WO | WO-2009102465 A2 * | 8/2009 | ............. A61P 37/04 |
| WO | WO 2009102465 A2 * | 8/2009 | ............. A61K 39/39 |
| WO | WO-09146456 A1 | 12/2009 | |
| WO | WO-09155583 A1 | 12/2009 | |
| WO | WO-201078209 A2 | 7/2010 | |
| WO | WO-10120749 A2 | 10/2010 | |
| WO | WO-11014871 A2 | 2/2011 | |
| WO | WO-2011/043834 A1 | 4/2011 | |
| WO | WO-2011/043835 A1 | 4/2011 | |
| WO | WO-11063336 A2 | 5/2011 | |
| WO | WO-11109834 A2 | 9/2011 | |
| WO | WO-11130753 A2 | 10/2011 | |
| WO | WO-11150240 A1 | 12/2011 | |
| WO | WO-11151431 A1 | 12/2011 | |
| WO | WO-11163669 A2 | 12/2011 | |
| WO | WO-12009611 A2 | 1/2012 | |
| WO | WO-12019049 A1 | 2/2012 | |
| WO | WO-2012048165 A2 | 4/2012 | |
| WO | WO-12064697 A2 | 5/2012 | |
| WO | WO-12148684 A1 | 11/2012 | |
| WO | WO-12149358 A1 | 11/2012 | |
| WO | WO-12167230 A1 | 12/2012 | |
| WO | WO-2013/012924 A2 | 1/2013 | |
| WO | WO-13106852 A1 | 7/2013 | |
| WO | WO-13158673 A1 | 10/2013 | |
| WO | WO-2013/172967 A1 | 11/2013 | |
| WO | WO-2013/190555 A1 | 12/2013 | |
| WO | WO-2014/063128 A1 | 4/2014 | |
| WO | 2014/189805 A1 | 11/2014 | |

(56) References Cited

FOREIGN PATENT DOCUMENTS

| WO | 2014/190229 A1 | 11/2014 |
|---|---|---|
| WO | 2015/066535 A1 | 5/2015 |
| WO | WO-2015/077354 A1 | 5/2015 |
| WO | WO-2015/154078 A1 | 10/2015 |
| WO | WO-2015168379 A2 | 11/2015 |
| WO | 2016/004068 A1 | 1/2016 |
| WO | WO-2016123573 A1 | 8/2016 |
| WO | WO-2016161372 A1 | 10/2016 |
| WO | WO-2017/143024 A2 | 8/2017 |
| WO | WO-2018/013797 A1 | 1/2018 |
| WO | WO-2018/026884 A1 | 2/2018 |

OTHER PUBLICATIONS

Vieira et al. Biomacromolecules, vol. 9, pp. 1195-1199 (2008) (of record).*
Fischbach et al., Advances in Polymer Science, vol. 203, pp. 191-221 (2006) (of record).*
Annabi et al., Tissue Engineering: Part B, vol. 16, No. 4, pp. 371-383; electonically published Mar. 17, 2010 (of record). (Year: 2010).*
Bouhadir et al., Biotechnology Progress, vol. 17, pp. 945-950; 2001 (of record). (Year: 2001).*
Boontheekul et al., Biomaterials, vol. 26, pp. 2455-2465; 2005 (of record). (Year: 2005).*
Vieira et al. Biomacromolecules, vol. 9, pp. 1195-1199 (2008) (of record). (Year: 2008).*
Fischbach et al., Advances in Polymer Science, vol. 203, pp. 191-221 (2006) (of record). (Year: 2006).*
"Collagen: The Fibrous Proteins of the Matrix." *Molecular Cell Biology*. Lodish et al., eds. New York: W.H. Freeman. Section 22.3(2000):979-985.
"Transient." Merriam-Webster Dictionary. Web. Jul. 18, 2014. www.merriam-webster.com/dictionary/transient.
Agache et al."Mechanical Properties and Young's Modulus of Human Skin in Vivo." *Arch. Dermatol. Res.* 269.3(1980):221-232.
Aguado et al. "Improving Viability of Stem Cells During Syringe Needle Flow Through the Design of Hydrogel Cell Carriers." *Tissue Eng. Part A.* 18.7-8(2012):806-815.
Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011 ):2418-2427.
American Diabetes Association. "Standards of Medical Care in Diabetes—2013." *Diabetes Care.* 36.S1(2013):S11-S66.
Annaidh et al. "Characterization of the Anistropic Mechanical Properties of Excised Human Skin." *J. Mech. Behav. Biomed. Mater.* 5.1(2012):139-148.
Aschner et al. "Metabolic Memory for Vascular Disease in Diabetes." *Diabetes Technol. Ther.* 14.S1(2012):S68-S74.
Aubin et al. "Directed 3D Cell Alignment and Elongation in Microengineered Hydrogels." *Biomater.* 31.27(2010):6941-6951.
Babensee et al. "Host Response to Tissue Engineered Device." *Adv. Drug Deli. Rev.* 33.1-2(1998):111-139.
Becker et al. "Cytological Demonstration of the Clonal Nature of Spleen Colonies Derived from Transplanted Mouse Marrow Cells." *Nature.* 197(1963):452-454.
Bell. "Models for the Specific Adhesion of Cells to Cells." *Science.* 200.4342(1978):618-627.
Bencherif et al. "Influence of Cross-Linker Chemistry on Release Kinetics of PEG-co-PGA Hydrogels." *J. Biomed. Mater. Res. A.* 90.1(2009):142-153.
Bencherif et al. "End-Group Effects on the Properties of PEG-co-PGA Hydrogels." *Acta Biomater.* 5.6(2009):1872-1883.
Bencherif et al. "Influence of the Degree of Methacrylation of Hyaluronic Acid Hydrogels Properties." *Biomater.* 29.12(2008):1739-1749.
Bencherif et al. "Injectable Preformed Scaffolds with Shape-Memory Properties." *PNAS.* 109.48(2012):19590-19595.

Bencherif et al. "Nanostructured Hybrid Hydrogels Prepared by a Combination of Atom Transfer Radical Polymerization and Free Radical Polymerization." *Biomater.* 30.29(2009):5270-5278.
Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.
Benton et al. "Photocrosslinking of Gelatin Macromers to Synthesize Porous Hydrogels that Promote Valvular Interstitial Cell Function." *Tissue Eng. Part A.* 15.11(2009):3221-3230.
Berg et al. "IL-10 is a Central Regulator of Cyclooxygenase-2 Expression and Prostaglandin Production." *J. Immunol.* 166.4(2001):2674-2680.
Bergstraesser et al. "Stimulation and Inhibition of Human Mammary Epithelial Cell duct Morphogenesis In Vitro." *Proc. Assoc. Am. Physicians.* 108.2(1996):140-154.
Bianco et al. "The Meaning, the Sense and the Significance: Translating the Science of Mesenchymal Stem Cells into Medicine." *Nat. Med.* 19.1 (2013):35-42.
Bilodeau et al. "Regular Pyramid Punch Problem." *J. Appl. Mech.* 59.3(1992):519-523.
Boateng et al. "Wound Healing Dressings and Drug Delivery Systems: A Review." *J. Pharm. Sci.* 97.8(2008):2892-2923.
Boerckel et al. "Mechanical Regulation of Vascular Growth and Tissue Regeneration in vivo." *PNAS.* 108.37(2011):E674-E680.
Boontheekul et al. "Controlling Alginate Gel Degradation Utilizing Partial Oxidation and Bimodal Molecular Weight Distribution." *Biomaterials.* 26.15(2005):2455-2465.
Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.
Broxmeyer et al. "Insights into the Biology of Cord Blood Stem/Progenitor Cells." *Cell Prolif.* 44.S1(2011):55-59.
Buckwaiter et al. "Form of Antigen Dictates Immunity: Irradiated Cell vs. Whole Cell Lysate Vaccination." *J. Immunol.* 178(2007).
Bullard et al. "Fetal Wound Healing: Current Biology." *World J. Surg.* 27.1(2003):54-61.
Buonaguro et al. "Translating Tumor Antigens into Cancer Vaccines." *Clin. Vaccine Immunol.* 18.1 (2011):23-34.
Burdick et al. "Controlled Degradation and Mechanical Behavior of Photopolymerized Hyaluronic Acid Networks." *Biomacromol.* 6.1(2005):386-391.
Burdick et al. "Photoencapsulation of Osteoblasts in Injectable RGD-Modified PEG Hydrogels for Bone Tissue Engineering." *Biomater.* 23.22(2002):4315-4323.
Béguéet al. "Vaccination Against Human Papillomavirus. Implementation and Efficacy Against Cervical Cancer Control." *Bull. Acad. Natl. Med.* 191.9(2007): 1805-1 816. (French original and English abstract).
Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.
Cameron et al. "The Influence of Substrate Creep on Mesenchymal Stem Cell Behaviour and Phenotype." *Biomater.* 32.26(2011):5979-5993.
Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Traction Dynamics of Filopodia on Compliant Substrates." *Science.* 322.5908(2008):1687-1691.
Chang. "Mouse Models for Studies of Retinal Degeneration and Diseases." *Methods Mol. Biol.* 935(2013):27-39.
Chen et al. "Adipogenic Differentiation of Adipose Tissue-Derived Human Mesenchymal Stem Cells: Effects of Gastric Bypass Surgery." *Surg. Endosc.* 26(2012):3449-3456.

(56) References Cited

OTHER PUBLICATIONS

Chen et al. "Functional Human Vascular Network Generated in Photocrosslinkable Gelatin Methacrylate Hydrogels." *Adv. Funct. Mater.* 22.10(2012):2027-2039.
Chiang et al. "Whole Tumor Antigen Vaccines." *Semin. Immunol.* 22.3(2010):132-143.
Choi et al. "In Vitro Mineralization by Preosteoblasts in Poly(DL-lactide-co-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Chou et al. "Characterization of Photocross Linked Alginate Hydrogels for Nucleus Pulposus Cell Encapsulation." *J. Biomed. Mater. Res. A.* 91A.1(2009):187-194.
Clark et al. "Myosin II and Mechanotransduction: A Balancing Act." *Trends Cell Biol.* 17.4(2007):178-186.
Comisar et al. "Engineering RGD Nanopatterned Hydrogels to Control Preosteoblast Behavior: A Combined Computational and Experimental Approach." *Biomaterials.* 28(2007):4409-4417.
Cook et al. "A Sialomucopeptide Liberated by Trypsin from the Human Erythrocyte." *Nature.* 188(1960):1011-1012.
Cooper. "Metabolic Memory: Implications for Diabetic Vascular Complications." *Pediatr. Diabetes.* 10.5(2009):343-346.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001): 1708-1712.
Dar et al. "Optimization of Cardiac Cell Seeding and Distribution in 3D Porous Alginate Scaffolds." *Biotechnol. Bioeng.* 80(2002):305-312.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
Dembo et al. "Stresses at the Cell-to-Substrate Interface During Locomotion of Fibroblasts." *Biophys. J.* 76.4(1 999):2307-2316.
Dexter et al. "Conditions Controlling the Proliferation of Haemopoietic Stem Cells In Vitro." *J. Ceil. Physiol.* 91,3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001 ):353-362.
Discher et al. "Tissue Cells Feel and Respond to the Stiffness of their Substrate." *Science.* 310.5751 (2005):1139-1143.
Disis et al. "Granulocyte-Macrophage Colony-Stimulating Factor: An Effective Adjuvant for Protein and Peptide-Based Vaccines." *Blood.* 88.1(1996):202-210.
Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1 Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A*0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183.6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AEQ22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NM_002421.3_May 11, 2014.
GenBank Accession No. NM_002982.3, May 3, 2014.
GenBank Accession No. NM_003377.4, May 5, 2014.
GenBank Accession No. NM_003392.4, May 5, 2014.
GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.

(56) References Cited

OTHER PUBLICATIONS

GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America*. NIH Publication No. 95-1468. Chapter2. (1995):15-36.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli*." *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chern.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Kang et al. "Effect of Porous Structure on the Degradation of Freeze-Dried Gelatin Hydrogels." *J. Bioact. Compat. Poly.* 14.4(1999):331-343.
Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11 (2013):1004-10017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Kim et al. "Multifunctional Capsule-in-Capsules for Immunoprotection and Trimodal Imaging." *Angew. Chem. Int. Ed.* 50.10(2011):2317-2321.
Klein et al. "Cell-Cycle Control by Physiological Matrix Elasticity and In Viivo Tissue Stiffening." *Curr. Biol.* 19.18(2009):1511-1518.
Kohane. "Microparticles and Nanoparticles for Drug Delivery." *Biotechnol. Bioeng.* 96.2(2007):203-209.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8+ T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Langenkamp et al. "Kinetics of Dendritic Cell Activation: Impact on Priming of TH1, TH2 and Nonpolarized T Cells." *Nat. Immunol.* 1.4(2000):311-316.
Lee et al. " Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lele et al. "Investigating Complexity of Protein-Protein Interactions in Focal Adhesions." *Biochem. Biophys. Res. Commun.* 369.3(2008):929-934.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "On the Viscoelastic Character of Liver Tissue: Experiments and Modelling of the Linear Behaviour." *Biorheol.* 37.3(2000):191-201.
Lo et al. "Cell Movement is Guided by the Rigidity of the Substrate." *Biophys. J.* 79.1(2000):144-152.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Majeti et al. "Identification of a Hierarchy of Multipotent Hematopoietic Progenitors in Human Cord Blood." *Cell Stem Cell.* 1.6(2007):635-645.
Malmqvist. "Biospecific Interaction Analysis Using Biosensor Technology." *Nature.* 361.6408(1993):186-187.
Mammoto et al. "Mechanical Control of Tissue and Organ Development." *Development.* 137.9(2010):1407-1420.
Manavski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.
Marui et al. "Simultaneous Application of Basic Fibroblast Growth Factor and Hepatocyte Growth Factor to Enhance the Blood Vessels Formation." *J. Vase. Surg.* 41.1(2005):82-90.
Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 110.43(2013):17253-17258.
Melief et al. "Immunotherapy of Established (Pre)Malignant Disease by Synthetic Long Peptide Vaccines." *Nat. Rev. Cancer.* 8(2008):351-360.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.

(56) References Cited

OTHER PUBLICATIONS

Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Mohan et al. "Novel Porous, Polysaccharide Scaffolds for Tissue Engineering Applications." *Trends Biomater. Artif. Organs.* 18.2(2005):219-224.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The 6β4 Integrin is a Receptor for Both Lamin and Kalinin." *Exp. Cell Res.* 211.2(1994):360-367.
Ohashi et al. "Surgical Excision Combined with Autologous Whole Tumor Cell Vaccination is an Effective Therapy for Murine Neuroblastoma." *J. Ped. Surg.* 41(2006): 1361-1368.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Stiffness on Mesenchymal Stem Cell Differentiation in a 3D Thixotropic Gel." *Biomater.* 31.3(2010):385-391.
Pena et al. "Effects of TGF-β and TGF-β Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFRα and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecularly Engineered PEG Hydrogels: A Novel Model System for Proteolyrically Mediated Cell Migration." *Biophys. J.* 89.2(2005):1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Reis e Sousa. "Activation of Dendritic Cells: Translating Innate into Adaptive Immunity." *Curr. Opin. Immunol.* 16.1(3005):21-25.
Roccaro et al. "BM Mesenchymal Stromal Cell-Derived Exosomes Facilitate Multiple Myeloma Progression." *J. Clin. Invest.* 123. 4(2013):1542-1555.
Rodriguez et al. "Minimal "Self" Peptides that Inhibit Phagocytic Clearance and Enhance Delivery of Nanoparticles." *Science.* 339. 6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Salem et al. "Defining the Antigen-Specific T-Cell Response to Vaccination and Poly(l:C)/TLR3 Signaling." *J. Immunother.* 28.3(2005):220-228.
Sarkar et al. "Condensation of Oligonucleotides Assembled into Nicked and Gapped Duplexes: Potential Structures for Oligonucleotide Delivery." *Nucleic Acids Res.* 33.1(2005):143-151.
Scheel et al. "Toll-Like Receptor-Dependent Activation of Several Human Blood Cell Types by Protamine Condensed mRNA." *Eur. J. Immunol.* 35(2005):1557-1566.
Schofield. "The Relationship Between the Spleen Colony-Forming Cell and the Haemopoietic Stem Cell." *Blood. Cells.* 4.1-2(1978):7-25.
Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110. 47(2013):18892-18897.
Shin et al. "Myonsin-II Inhibition and Soft 2D Matrix Maximize Multinucleation and Cellular Projections Typical of Platelet-Producing Megakaryocytes." *PNAS.* 10 8.28(201 1):11458-11463.
Shoichet et al. "Stability of Hydrogels Used in Cell Encapsulation: An In Vitro Comparison of Alginate and Agarose." *Biotechnol. Bioeng.* 50(1996):374-381.
Siegwart et al. "Synthesis, Characterization, and in vitro Cell Culture Viability of Degradable Poly(N-isopropylacrylamide-co-5,6-benzo-2-methylene-1,3-dioxepane)-Based Polymers and Cross-linked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Singer et al. "Cutaneous Wound Healing." *N. Engl. J. Med.* 341. 10(1999):738-746.
Solon et al. "Fibroblast Adaptation and Stiffness Matching to Soft Elastic Substrates." *Biophys. J.* 93.12(2007):4453-4461.

(56) References Cited

OTHER PUBLICATIONS

Stachowiak et al. "Inverse Opal Hydrogel-Collagen Composite Scaffolds as a Supportive Microenvironment for Immune Cell Migration." *J. Biomed. Mater. Res.* 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter*. 8(2012):2398-2404.
Sun et al. "Highly Stretchable and Tough Hydrogels." *Nature*. 489.7414(2012):133-136.
Suri et al. "Photopatterned Collagen-Hyaluronic Acid Interpenetrating Polymer Network Hydrogels." *Acta Biomater*. 5.7(2009):2385-2397.
Swift et al. "Nuclear Lamin-A Scales with Tissue Stiffness and Enhances Matrix-Directed Differentiation." *Science*. 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release*. 31.2(1994):189-199.
Tannous. "*Gaussia* Luciferase Reporter Assay for Monitoring Biological Processes in Culture and in vivo." *Nat. Protoc*. 4.4(2009):582-591.
Thomas et al. "Intravenous Infusion of Bone Marrow in Patients Receiving Radiation and Chemotherapy." *N. Engl. J. Med*. 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med*. 190.11(1999):1669-1678.
Tong et al. "Engineering Interpenetrating Network Hydrogels as Biomimetic Cell Niche with Independently Tunable Biochemical and Mechanical Properties." *Biomater*. 35.6(2014):1807-1815.
Trappmann et al. "Extracelluar-Matrix Tethering Regulates Stem-Cell Fate." *Nat. Mater*. 11.7(2012):642-649.
Trappmann et al. "How Cells Sense Extracellular Matrix Stiffness: A Material's Perspective." *Curr. Opin. Biotechnol*. 24.5(2013):948-953.
Ugarte et al. "Notch Signaling Enhances Osteogenic Differentiation While Inhibiting Adipogenesis in Primary Human Bone Marrow Stromal Cells." *Exp. Hematol*. 37(2009):867-875.
Uhlenbruck. "Action of Proteolytic Enzymes on the Human Erythrocyte Surface." *Nature*. 190(1961):181.
Ulrich et al. "Probing Cellular Mechanobiology in Three-Dimensional Culture with Collagen-Agarose Matrices." *Biomater*. 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.

Van der Bruggen et al. "T Cell-Defined Tumor Antigens." *Cancer Immunity*. (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun*. 303.2(2003):508-513.
Vincent et al. "Stem Cell Differentiation: Post-Degradation Forces Kick in." *Nat. Mater*. 12.5(2013):384-386.
Vogel et al. "Local Force and Geometry Sensing Regulate Cell Functions." *Nat. Rev. Mol. Cell Biol*. 7.4(2006):265-275.
Wang et al. "Mechanotransduction at a Distance: Mechanically Coupling the Extracellular Matric with the Nucleus." *Nat. Rev. Mol. Cell. Biol*. 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs*. 31.3(2013):707-713.
Warner et al. "Cyclooxygenases: New Forms, New Inhibitors, and Lessons from the Clinic." *FASEB J*. 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res*. 30(1963):331-338.
Wen et al. "Mechanically Robust Gelatin-Alginate IPN Hydrogels by a Combination of Enzymatic and Ionic Crosslinking Approaches." *Macromol. Mater. Eng*. 299(2013):504-513.
Wieland et al. "Engineering Molecular Circuits Using Synthetic Biology in Mammalian Cells." *Annu. Rev. Chem. Biomol. Eng*. 3(2012):209-234.
Wipff et al. "Myofibroblast Contraction Activates Latent TGF-$\beta$1 from the Extracellular Matrix." *J. Cell Biol*. 179.6(2007):1311-1323.
Wong et al. "Focal Adhesion Kinase Links Mechanical Force to Skin Fibrosis via Inflammatory Signaling." *Nat. Med*. 18.1(2011):148-152.
Wong et al. "Mechanical Force Prolongs Acute Inflammation via T-Cell-Dependent Pathways During Scar Formation." *FASEB. J*. 25.12(2011):4498-4510.
Wong et al. "Pushing Back: Wound Mechanotransduction in Repair and Regeneration." *J. Invest. Dermatol*. 131.11(2011):2186-2196.
Wozniak et al. "Mechanotransduction in Development: A Growing Role for Contractility." *Nat. Rev. Mol. Cell Biol*. 10.1(2009):34-43.
Yeung et al. "Effects of Substrate Stiffness on Cell Morphology, Cytoskeletal Structure, and Adhesion." *Cell Motil. Cytoskeleton*. 60.1(2005):24-34.
Yoo et al. "Bio-Inspired, Bioengineered and Biomimetic Drug Delivery Carriers." *Nat. Rev. Drug Discov*. 10.7(2011):521-535.
Yoon. "Hidden Markov Models and their Applications in Biological Sequene Analysis." *Curr. Genomics*. 10.6(2009):402-415.
Young et al. "Gelatin as a Delivery Vehicle for the Controlled Release of Bioactive Molecules." *J. Control. Release*. 109.1-3(2005):256-274.
Zemel et al. "Optimal Matrix Rigidity for Stress Fibre Polarization in Stem Cells." *Nat. Phys*. 6.6(2010):468-473.
Zhang et al. "A Tension-Induced Mechanostransduction Pathway Promotes Epithelial Morphogenesis." *Nature*. 471.7336(2011):99-103.
Zhang et al. "Talin Depletion Reveals Independence of Initial Cell Spreading from Integrin Activation and Traction." *Nat. Cell Biol*. 10.9(2008):1062-1068.
Zhao et al. "Stress-Relaxation Behavior in Gels with Ionic and Covalent Crosslinks." *J. Appl. Phys*. 107.6(2010):63509.
Corcione et al. "CCL19 and CXCL12 trigger in vitro chemotaxis of human mantle cell lymphoma B cells." *Clin CancerRes*. Feb. 1, 2004;10(3):964-71.
Latorre et al. "Applications of magnetic nanoparticles in medicine: magnetic fluid hyperthermia." *P R Health Sci J*. Sep. 2009;28(3):227-38.
Malhotra et al. "Use of an oncolytic virus secreting GM-CSF as combined oncolytic and immunotherapy for treatment of colorectal and hepatic adenocarcinomas." *Surgery*. Apr. 2007;141(4):520-9.
Nestle et al. "Vaccination of melanoma patients with peptide- or tumor lysate-pulsed dendritic cells." *Nat Med*. Mar. 1998;4(3):328-32.

(56) References Cited

OTHER PUBLICATIONS

Wang et al. "Photothermal effects of supramolecularly assembled gold nanoparticles for the targeted treatment of cancer cells." *Angew Chem Int Ed Engl.* May 17, 2010;49(22):3777-81.
Sato, "Human dendritic cells." *Biotherapy.* Nov. 2004;18(6):467-77.
*Annual Review Meneki (Immunity).* 2007;2008:122-31.
Fransen et al. "Local immunomodulation for cancer therapy: Providing treatment where needed." *Oncoimmunology.* Nov. 1, 2013;2(11):e26493.
Yamazaki et al., "CD8+ CD205+ splenic dendritic cells are specialized to induce Foxp3+ regulatoryT cells." *J. Immunology.* 181:6923-6933 (2008).
Yang, Fan et al., "The effect of incorporating RGD adhesive peptide in polyethylene glycol diacrylate hydrogel on osteogenesis of bone marrow stromal cells," *Biomaterials*, vol. 26(2005):5991-5998.
"Antigens and Receptors." *Immunology.* Doan et al., eds. Philadelphia: Wolters Kluwer/Lippincott Williams & Wilsons. (2008):11-23.
"Wound Management: Past, Present, and Future." *Clinicians' Pocket Guide to Chronic Wound Repair.* Mulder et al., eds. Springhouse, PA: Springhouse Corporation. (1998):85-90.
Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and a Set of Arteries." *New Scientist.* 2547(2006):19.
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
Ali et al. "Converging Cell Therapy with Biomaterials." *Cell Transplantation from Laboratory to Clinic.* Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Ali et al. "Sustained GM-CSF and PEI Condensed pDNA Presentation Increases the Level and Duration of Gene Expression in Dendritic Cells." *J. Control. Release.* 132.3(2008):273-278.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11 (2001):2025-2029.
Alsberg et al. "Engineering Growing Tissues." *PNAS.* 99.18(2002):12025-12030.
Alsberg et al. "Regulating Bone Formation via Controlled Scaffold Design." *J. Dent. Res.* 82.11(2003):903-908.
Anderson et al. "Biomaterial Microarrays: Rapid, Microscale Screening of Polymer-Cell Interaction." *Biomaterials.* 26.23(2005):4892-4897.

Anderson et al. "Nanoliter-Scale Synthesis of Arrayed Biomaterials and Application to Human Embryonic Stem Cells." *Nat. Biotechnol.* 22.7(2004):863-866.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.
Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Augst et al. "Alginate Hydrogels as Biomaterials." *Macromol. Biosci.* 6(2006):623-633.
Bachem et al. "Superior Antigen Cross-Presentation and XCR1 Expression Define Human CD11 c+CD141 * Cells as Homologues of Mouse CD8+ Dendritic Cells." *J. Exp. Med.* 207.6(2010):1273-1281.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Balakrishna et al. "Structural Correlates of Antibacterial and Membrane-Permeabilizing Activities in Acylpolyamines." *Antimicrob. Agents Chemother.* 50.3(2006):852-861.
Banchereau et al. "Dendritic Cells and the Control of Immunity." *Nature.* 392.6673(1998):245-252.
Bar-Cohen et al. "Electroactive Polymer Actuators and Sensors." *MRS Bullet.* 33.3(2008): 173-181.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation-A Cell Therapy Approach." *J. Cell. Physiol.* 186(2001): 183-192.
Barrio et al. "A Two-Dimensional Numerical Study of Spatial Pattern Formation in Interacting Turing Systems." *Bull. Math Biol.* 61.3(1999):483-505.
Bates. "Improved Muscle Regeneration by Combining VEGF With IGF1." *Regen. Med.* 5.6(2010):853-854.
Beaucage et al. "The Functionalization of Oligonucleotides Via Phosphoramidite Derivatives." *Tetrahedron.* 49.10(1993):1925-1963.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Beebe et al. "Functional Hydrogel Structures for Autonomous Flow Control Inside Microfluidic Channels." *Nature.* 404(2000):588-590.
Bekiari et al. "Study of Poly(N,M-dimethylacrylamide)/CdS Nanocomposite Organic/Inorganic Gels." *Langmuir.* 20.19(2004):7972-7975.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.
Bohl et al. "Role of Synthetic Extracellular Matrix in Development of Engineered Dental Pulp." *J. Biomater. Sci. Polym. Ed.* 9.7(1998):749-764.
Bonauer et al. "MicroRNA-92a Controls Angiogenesis and Functional Recovery of Ischemic Tissues in Mice." *Science.* 324.5935(2009):1710-1713.
Boontheekul et al. "Regulating Myoblast Phenotype Through Controlled Gel Stiffness and Degradation." *Tissue Engin.* 13.7(2007):1431-1442.

(56) References Cited

OTHER PUBLICATIONS

Borselli et al. "Functional Muscle Regeneration with Combined Delivery of Angiogenesis and Myogenesis Factors." *PNAS.* 107.8(2010):3287-3292.
Bouhadir et al. "Degradation of Partially Oxidized Alginate and its Potential Application for Tissue Engineering." *Biotechnol. Prog.* 17.5(2001):945-950.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brinkmann et al. "Neutrophil Extracellular Traps Kill Bacteria." *Science.* 303.5663(2004):1532-1535.
Brouwers et al. "Can the Growth Factors PTHrP, Ihh and VEGF, Together Regulate the Development of a Long Bone?" *J. Biomech.* 39.15(2006):2774-2782.
Bryant et al. "Photo-Patterning of Porous Hydrogels for Tissue Engineering." *Biomater.* 28.19(2007):2978-2986.
Burdick et al. "Stimulation of Neurite Outgrowth by Neurotrophins Delivered From Degradable Hydrogels." *Biomater.* 27.3(2006):452-459.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB J.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engingeered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Conboy et al. "The Regulation of Notch Signaling Controls Satellite Cell Activation and Cell Fate Determination in Postnatal Myogenesis." *Dev. Cell.* 3.3(2002):397-409.
Conconi et al. "In vitro and in vivo Evaluation of Acellular Diaphragmatic Matrices Seeded with Muscle Precursors Cells and Coated with VEGF Silica Gel to Repair Muscle Defect of the Diaphragm." *J. Biomed. Mater. Res.* 89A.2(2009):304-316.

Conn et al. "Purification of a Glycoprotein Vascular Endothelial Cell Mitogen from a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1 (2001):79-94.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1 (2000):49-58.
De Temmerman et al. "Particulate Vaccines: On the Quest for Optimal Delivery and Immune Response." *Drug Disc. Today.* 16.13/14(2011):569-582.
Den Haan et al. "CD8+ by not CD8- Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Doan et al. "Subcellular Localization of a Sporulation Membrane Protein is Achieved Through a Network of Interactions Along and Across the Septum." *Mol. Microbiol.* 55.6(2005):1767-1781.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
Egholm et al. "Peptide Nucleic Acids (PNA). Oligonucleotide Analogues with an Achiral Peptide Backbone." *J. Am. Chem. Soc.* 114.5(1992):1895-1897.
Egholm et al. "PNA Hybridizes to Complementary Oligonucleotides Obeying the Watson-Crick Hydrogen-Bonding Rules." *Nature.* 365.6446(1993):566-568.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.

(56) References Cited

OTHER PUBLICATIONS

Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(Lactic-Co-Glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in Drosophila Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lingeage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Falsey et al. "Peptide and Small Molecule Microarray for High Throughput Cell Adhesion and Functional Assays." *Bioconjug. Chem.* 12.3(2001):346-353.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.
Ferrara et al. "Discovery and Development of Bevacizumab, an Anti-VEGF Antibody for Treating Cancer." *Nat. Rev. Drug Discov.* 3.5(2004):391-400.
Fischer et al. "A Brilliant Monomeric Red Fluorescent Protein to Visualize Cytoskeleton Dynamics in *Dictyostelium*." *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Fontaine et al. "Surgical Treatment of Peripheral Circulation Disorders." *Helv. Chir. Acta.* 21.56(1954):499-533. (German Original, No English Translation Available).
Fox. "Management of Worsening Multiple Sclerosis with Mitoxantrone: A Review." *Clin. Ther.* 28.4(2006):461-474.
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
Gamvrellis et al. "Vaccines that Facilitate Antigen Entry into Dendritic Cells." *Immunol. Cell Biol.* 82(2004):506-516.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAI44040, Mar. 18, 2009.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. EF064765.1, Nov. 13, 2006.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Glasbey et al. "Image Analysis and Three-Dimensional Modelling of Pores in Soil Aggregates." *Eur. J. Soil Sci.* 42.2(1991):479-486.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol. Head Neck Surg.* 130.10(2004):1191-1196.
Gros et al. "A Common Somitic Origin for Embryonic Muscle Progenitors and Satellite Cells." *Nature.* 435(2005):954-958.

(56) References Cited

OTHER PUBLICATIONS

Gullberg et al. "Extracellular Matrix and Its Receptors During Development." *Int. J. Dev. Biol.* 39(1995):845-854.
Gupta et al. "Magnetically Controlled Targeted Micro-Carrier Systems." *Life Sci.* 44.3(1989):175-186.
Gussoni et al. "Dystophin Expression and in the mdx Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3(1999):169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG Dna: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004):1407-1414.
Hawke et al. "Myogenic Satellite Cells: Physiology to Molecular Biology." *J. Appl. Physiol.* 91(2001):534-551.
Heath. "Cells for Tissue Engineering." *Trends Biotechnol.* 18.1(2006):17-19.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.
Hermanson. *Bioconjugate Techniques.* New York: Academic Press. (1996):152-185.
Heslop et al. "Transplanted Primary Neonatal Myoblasts can Give Rise to Functional Satellite Cells as Identified Using the Myf5nlacZI+ Mouse." *Gene Ther.* 8(2001 ):778-783.
Hildner et al. "Batf3 Deficiency Reveals a Critical Role for CD8α+ Dendritic Cells in Cytotoxic T Cell Immunity." *Science.* 322. 5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.

Hodge-Dufour et al. "Inhibition of Interferon γ Induced Interleukin 12 Production: A Potential Mechanism for the Anti-Inflammatory Activities of Tumor Necrosis Factor." *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *Bio/Tech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Jain. "Molecular Regulation of Vessel Maturation." *Nat. Med.* 9.6(2003):685-693.
Jain. "The Manufacturing Techniques of Various Drug Loaded Biodegradable Poly(lactide-co-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primorida." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of Gm-CSF." *J. Clin. Invest.* 117.7(2007):1902-1913.
Johnson et al. "Activation of Skeletal Muscle Satellite Cells and the Role of Fibroblast Growth Factor Receptors." *Exp. Cell Res.* 219.2(1995):449-453.
Juntanon et al. "Electrically Controlled Release of Sulfosalicylic Acid from Crosslinked Poly(Vinyl Alcohol) Hydrogel." *Int. J. Pharm.* 356(2008):1-11.
Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.1-2(1999):279-287.
Khownium et al. "Novel Endotoxin-Compounds with Terephthalaldehyde-bis-guanylhydrazone Scaffolds." *Bioorg. Med. Chem. Lett.* 16(2006):1305-1308.
Kim et al. "An Overview of Cartilage Tissue Engineering." *Yonsei Med. J.* 41.6(2000):766-773.
Kim et al. "The Effect of VEGF on the Myogenic Differentiation of Adipose Tissue Derived Stem Cells Within Thermosensitive Hydrogel Matrices." *Biomaterials.* 31.6(2010):1213-1218.

(56) References Cited

OTHER PUBLICATIONS

Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish Pomacanthus." *Nature.* 376(2002):765-768.
Kong et al. "Controlling Degradation of Hydrogels via the Size of Crosslinked Junctions." *Adv. Mater.* 16.21 (2004):1917-1921.
Kong et al. "Controlling Rigidity and Degradation of Alginate Hydrogels via Molecular Weight Distribution." *Biomacromolec.* 5.5(2004):1720-1727.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Kong et al. "Designing Alginate Hydrogels to Maintain Viability of Immobilized Cells." *Biomat.* 24.22(2003):4023-4029.
Kong et al. "Non-Viral Gene Delivery Regulated By Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumamoto et al. "Induction of Tumor-Specific Protective Immunity by in situ Langerhans Cell Vaccine." *Nat. BioTechnol.* 20.1(2002):64-69.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "Electrically Erodible Polymer Gel for Controlled Release of Drugs." *Nature.* 354(1991):291-293.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langer et al. "Tissue Engineering." *Science.* 260(1993):920-926.
Lanzavecchia et al. "Regulation of T Cell Immunity by Dendritic Cells." *Cell.* 106.3(2001):263-266.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α+ DCs and Human BDCA3+ DCs are Major Producers of IFN-λ in Response to Poly IC." *J. Exp. Med.* 207.12(2010):2703-2717.
Leach et al. "Coating of VEGF-Releasing Scaffolds with Bioactive Glass for Angiogenesis and Bone Regeneration." *Biomater.* 27.17(2006):3249-3255.
Lee et al. "Hydrogel Formation via Veil Crosslinking." *Adv. Mat.* 15.21 (2003):1828-1832.
Lee et al. "Hydrogels for Tissue Engineering." *Chem. Rev.* 101.7(2001):1869-1879.
Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embryonic Stem Cells." *Blood.* 107.7(2006):2605-2612.
Leor et al. "Cells, Scaffolds, and Molecules for Myocardial Tissue Engineering." *Pharmacol. Therapeutics.* 105(2005):151-163.

Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Letsinger et al. "Phosphoramidate Analogs of Oligonucleotides." *J. Org. Chem.* 35.11(1970):3800-3803.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu et al. "Nanostructured Materials Designed for Cell Binding and Transduction." *Biomacromolecules.* 2.2(2001):362-368.
Liu. "Dendritic Cell Subsets and Lineages, and Their Functions in Innate and Adaptive Immunity." *Cell.* 106.3(2001):259-262.
López et al. "Magnetic Applications of Polymer Gels." *Macromol. Symp.* 166.1(2001):173-178.
Lu et al. "Muscle-Derived Stem Cells Seeded Into Acellular Scaffolds Develop Calcium-Dependent Contractile Activity That is Modulated by Nicotinic Receptors." *Urology.* 61.6(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Lutolf et al. "Repair of Bone Defects Using Synthetic Mimetics of Collagenous Extracellular Matrices." *Nat. Biotechnol.* 21.5(2003):513-518.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin αvβ3-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-β Superfamily Member." *Nature.* 387(1997):83-90.
Meier et al. "Peptide Nucleic Acids (PNAs)—Unusual Properties of Noionic Oligonucleotide Analogues." *Angew. Chern. Int. Ed.* 31.8(1992):1008-1010.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meraz et al. "Mesoporous Silicon Particles for the Presentation of Tumor Antigens and Adjuvantfor Anti-Cancer Immunity." *Cancer Res.* 71.S24(2011):159s-160s. (Abstract #P1-01-12).

(56) References Cited

OTHER PUBLICATIONS

Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Miller et al. "Lipopolysaccharide Sequestrants: Structural Correlates of Activity and Toxicity in Novel Acylhomospermines." *J. Med. Chem.* 48(2005):2589-2599.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Miyata et al. "Biomolecule-Sensitive Hydrogels." *Adv. Drug Deliv. Rev.* 54.1(2002):79-98.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_004119, Apr. 14, 2013.
NCBI Accession No. NM_006274.2, Mar. 31, 2013.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Niamlang et al. "Electrically Controlled Release of Salicylic Acid from poly(p-phenylene vinylene) Polyacrylamide Hydrogels." *Int. J. Pharm.* 371(2009):126-133.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1 (2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Orner et al. "Arrays for the Combinatorial Exploration of Cell Adhesion." *J. Am. Chem. Soc.* 126.35(2004):10808-10809.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor a Gene Expression in Respiratory and Peripheral Muscles." *Arch. Bronconeumol.* 38.7(2002):311-316. (Spanish Original and English Abstract).
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Partridge et al. "Conversion of mdx Myofibres From Dystrophin-Negative to -Positive by Injection of Normal Myoblasts." *Nature.* 337(1989):176-179.
Pedersen et al. "Induction of Regulatory Dendritic Cells by Desamethasone and 1α,25-Dihydroxyvitamin $D_3$." *Immunol. Lett.* 91(2004):63-69.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to Listeria monocytogenes Infection." *J. Immunol.* 166(2001):3402-3409.
Porter et al. "Separation of Natural Populations of Coliform Bacteria from Freshwater and Sewage by Magnetic-Bead Cell Sorting." *J. Microbiol. Meth.* 33.3(1998):221-226.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.
Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Qui et al. "Environment-Sensitive Hydrogels for Drug Delivery." *Adv. Drug Deliv. Rev.* 53.3(2001):321-339.
Rajagopalan et al. "Regional Angiogenesis With Vascular Endothelial Growth Factor in Peripheral Arterial Disease: A Phase II Randomized, Double-Blind, Controlled Study of Adenoviral Delivery of

(56) References Cited

OTHER PUBLICATIONS

Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.*10(1998):366. (Abstract #153.07).
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.*15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rizzo et al. "An Improved Cyan Fluorescent Protein Variant Useful for FRET." *Nat. Biotechnol.* 22.4(2004):445-449.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Facilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salvador et al. "Combination of Immune Stimulating Adjuvants With Poly(lactide-co-glycolide) Microspheres Enhances the Immune Response of Vaccines." *Vaccine.* 30.3(2011):589-596.
Salvay et al. "Inductive Tissue Engineering with Protein and DNA-Releasing Scaffolds." *Mol. Biosyst.* 2.1(2006):36-48.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.

Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(l:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Shaner et al. "Improved Monomeric Red, Orange and Yellow Fluorescent Proteins Derived from *Discosoma sp.* Red Fluorescent Protein." *Nat. Biotechnol.* 22.12(2004):1567-1572.
Shansky et al. "Letter to the Editor: A Simplified Method for Tissue Engineering Skeletal Muscle Organoids In Vitro." *In Vitro Cell. Dev. Biol.* 33(1997):659-661.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Material-Based Deployment Enhances Efficacy of Endothelial Progenitor Cells." *PNAS.* 105.38(2008):14347-14352.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8- DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Muse. Res. Cell. Motil.* 24.4-6(2003):285-300.
Smidsrod et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161 (2007):419-426.
Storrie et al. "Sustained Delivery of Plasmid DNA From Polymeric Scaffolds for Tissue Engineering."*Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takahashi et al. "Induction of Pluripotent Stem Cells from Adult Human Fibroblasts by Defined Factors." *Cell.* 131.5(2007):861-872.

(56) References Cited

OTHER PUBLICATIONS

Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.
Tanaka et al. "Collapse of Gels in an Electric Field." *Science.* 218(1982):467-469.
Tatsumi et al. "HGF/SF Is Present in Normal Adult Skeletal Muscle and Is Capable of Activating Satellite Cells." *Dev. Biol.* 194.1(1998):114-128.
Ten Dijke et al. "Growth Factors for Wound Healing." *Nat. Biotechnol.* 7(1989):793-798.
Thurston et al. "The Delta Paradox: DLL4 Blockade Leads to More Tumour Vessels but Less Tumour Growth." *Nat. Rev. Cancer.* 7.5(2007):327-331.
Tidball. "Inflammatory Cell Response to Acute Muscle Injury." *Med. Sci. Sports Exerc.* 27.7(1995):1022-1032.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Turing. "Discussion: Turing's Theory of Morphogenesis—It's Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.
Uchida et al. "Immunization by Particle Bombardment of Antigen-Loaded poly-(DL-lactide-co-glycolide) Microspheres in Mice." *Vaccine.* 12(2006):2120-2130.
Urbanek et al. "Stem Cell Niches in the Adult Mouse Heart." *PNAS.* 103.24(2006):9226-9231.
Van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced lgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
Von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wang et al. "Evolution of New Nonantibody Proteins via Iterative Somatic Hypermutation." *PNAS.* 101.48(2004):16745-16749.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Muse. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Xie et al. "Preparation and Application of Surface-Coated Superparamagnetic Nanobeads in the Isolation of Genomic DNA." *J. Magn. Magnetic Mater.* 277.1(2004):16-23.
Yancopoulos et al. "Vascular-Specific Growth Factors and Blood Vessel Formation." *Nature.* 407.6801(2000):242-248.
Yu et al. "Induced Pluripotent Stem Cell Lines Derived from Human Somatic Cells." *Science.* 318.5858(2007):1917-1920.
Yuen et al. "Mimicking Nature by Codelivery of Stimulant and Inhibitor to Create Temporally Stable and Spatially Restricted Angiogenic Zones." *PNAS.* 107.42(2010):17933-17938.
Yuk et al. "Electric Current-Sensitive Drug Delivery System Using Sodium Alginate/Polyacrylic Acid Composites." *Pharm. Res.* 9.7(1992):955-957.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
De Jong et al. "Regulation of Notch Signaling Genes During BMP2-lnduced Differentiation of Osteoblast Precursor Cells." *Biochem. Biophys. Res. Commun.*320(2004):100-107.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007):1113-1124.
Miljkovic et al. "Chondrogenesis, Bone Morphogenetic Protein-4 and Mesenchymal Stem Cells." *Osteoarthritis Cartilage.* 16(2008):1121-1130.
NCBI Accession No. NP_001193, May 3, 2014.
Brunner et al. Enhanced dendritic cell maturation by TNF-alpha or cytidine-phosphate-guanosine DNA drives T cell activation in citro and therapeutic anti-tumor immune responses in vivo. J Immunol. Dec. 1, 2000;1;165(11):6278-86.
Kathuria et al. "Synthesis and characterization of elastic and macroporous chitosan-gelatin cryogels for tissue engineerin" Act Abiomaterialia 5 (2009) 406-418.
Liu et al. Immunostimulatory CpG oligodeoxynucleotides enhance the immune response to vaccine strategies involving granulocyte-macrophage colony-stimulating factor. Blood. Nov. 15, 1998;92(10):3730-6.
Liu et al., "Preparation of uniform calcium alginate gel beads by membrane emulsification coupled with internal gelation." Journal of Applied Polymer Science. Nov. 22, 2002;87:848-852.

(56) References Cited

OTHER PUBLICATIONS

Holland et al.. Dual growth factor delivery from degradable oligo(poly(ethylene glycol) fumarate) hydrogel scaffolds for cartilage tissue engineering. Journal of Controlled Release. 2005;101:111-125.
Aharoni et al., New findings and old controversies in the research of multiple sclerosis and its model experimental autoimmune encephalomyelitis. Expert Rev Clin Immunol. May 2013;9(5):423-40.
Ali et al., Biomaterial-based vaccine induces regression of established intracranial glioma in rats. Pharm Res. May 2011;28(5):1074-80.
Ali et al., Identification of immune factors regulating antitumor immunity using polymeric vaccines with multiple adjuvants. Cancer Res. Mar. 15, 2014;74(6):1670-81.
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Ali et al., The efficacy of intracranial PLG-based vaccines is dependent on direct implantation into brain tissue. J Control Release. Sep. 25, 2011;154(3):249-57.
Ambrosini et al., Astrocytes produce dendritic cell-attracting chemokines in vitro and in multiple sclerosis lesions. J Neuropathol Exp Neurol. Aug. 2005;64(8):706-15.
Barbucci et al., Hyaluronic acid hydrogel in the treatment of osteoarthritis. Biomaterials. Dec. 2002;23(23):4503-13.
Bartholomew et al., Mesenchymal stem cells suppress lymphocyte proliferation in vitro and prolong skin graft survival in vivo. Exp Hematol. Jan. 2002;30(1):42-8.
Baskin et al., Copper-free click chemistry for dynamic in vivo imaging. Proc Natl Acad Sci U S A. Oct. 23, 2007;104(43):16793-7.
Bojarova et al., Sugared biomaterial binding lectins: achievements and perspectives. Biomater Sci. Jul. 19, 2016;4(8):1142-60.
Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.
Bucki et al., Combined antibacterial and anti-inflammatory activity of a cationic disubstituted dexamethasone-spermine conjugate. Antimicrob Agents Chemother. Jun. 2010;54(6):2525-33.
Callahan et al., At the bedside: CTLA-4- and PD-1-blocking antibodies in cancer immunotherapy. J Leukoc Biol. Jul. 2013;94(1):41-53.
care.diabetesjournals.org, Standards of Medical Care in Diabetes. Diabetes Care. Jan. 2013;36(Suppl 1):S1-S2.
Champion et al., Shape induced inhibition of phagocytosis of polymer particles. Pharm Res. Jan. 2009;26(1):244-9.
Chapman, Endosomal proteases in antigen presentation. CurrOpin Immunol. Feb. 2006;18(1):78-84.
Chen et al., Programmed cell death of dendritic cells in immune regulation. Immunol Rev. Jul. 2010;236:11-27.
ClinicalTrials.Gov, NCT00729664, Multiple Ascending Dose (MDX1105-01) (Anti-PDL1). 4 pages, Sep. 3, 2015.
ClinicalTrials.Gov, NCT00730639, A Phase 1 Study of Nivolumab (BMS-936558) in Subjects with Advanced or Recurrent Malignancies (MDX1106-03). 5 pages, Mar. 24, 2016.
ClinicalTrials.Gov, NCT01352884, Study to Assess the Safety, and Pharmacokinetics of AMP-224 in Patients with Advanced Cancer. 3 pages, Sep. 2, 2016.
ClinicalTrials.Gov, NCT01391143, Safety Study of MGA271 in Refractory Cancer. 4 pages, Sep. 28, 2016.
Coutinho et al., The anti-inflammatory and immunosuppressive effects of glucocorticoids, recent developments and mechanistic insights. Mol Cell Endocrinol. Mar. 15, 2011;335(1):2-13.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.
Dainiak et al., Gelatin-fibrinogen cryogel dermal matrices for wound repair: preparation, optimisation and in vitro study. Biomaterials. Jan. 2010;31(1):67-76.
Deshmane et al., Monocyte chemoattractant protein-1 (MCP-1): an overview. J Interferon Cytokine Res. Jun. 2009;29(6):313-26.
Dong et al., Antitumor effect of secreted Flt3-ligand can act at distant tumor sites in a murine model of head and neck cancer. Cancer Gene Ther. Feb. 2003;10(2):96-104.
Duraiswamy et al., Dual blockade of PD-1 and CTLA-4 combined with tumor vaccine effectively restores T-cell rejection function in tumors-response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
El-Behi et al., The encephalitogenicity of T(H)17 cells is dependent on IL-1- and IL-23-induced production of the cytokine GM-CSF. Nat Immunol. Jun. 2011;12(6):568-75.
Ford et al., Specificity, magnitude, and kinetics of MOG-specific CD8+ T cell responses during experimental autoimmune encephalomyelitis. Eur J Immunol. Jan. 2005;35(1):76-85.
Furqan et al., STAT inhibitors for cancer therapy. J Hematol Oncol. Dec. 5, 2013;6:90. 11 pages.
Ganguly et al., The role of dendritic cells in autoimmunity. Nat Rev Immunol. Aug. 2013;13(8):566-77.
GenBank Accession No. NM_001025081.1, Jan. 19, 2019.
GenBank Accession No. NP_001020252.1, Jan. 19, 2019.
Getts et al., Current landscape for T-cell targeting in autoimmunity and transplantation. Immunotherapy. Jul. 2011;3(7):853-70.
Goddard et al., Polymer surface modification for the attachment of bioactive compounds. Progress in Polymer Science. Jul. 2007;32(7):698-725.
Gomez-Cambronero, Rapamycin inhibits GM-CSF-induced neutrophil migration. FEBS Lett. Aug. 28, 2003;550(1-3):94-100.
Gutsmiedl et al., Copper-free "click" modification of DNA via nitrile oxide-norbornene 1,3-dipolar cycloaddition. Org Lett. Jun. 4, 2009;11 (11):2405-8.
Haase et al., CD40 is necessary for activation of naive T cells by a dendritic cell line in vivo but not in vitro. Scand J Immunol. Mar. 2004;59(3):237-45.
Hansell et al., Additive-free clicking for polymer functionalization and coupling by tetrazine-norbornene chemistry. J Am Chem Soc. Sep. 7, 2011;133(35):13828-31.
Hodi et al., Improved survival with ipilimumab in patients with metastatic melanoma. N Engl J Med. Aug. 19, 2010;363(8):711-23.
Howard et al., Polymer micelles with hydrazone-ester dual linkers for tunable release of dexamethasone. Pharm Res. Oct. 2011;28(10):2435-46.
Hu et al., Tolerogenic dendritic cells and their potential applications. Immunology. Mar. 2011;132(3):307-14.
Ichida et al., A small-molecule inhibitor of tgf-Beta signaling replaces sox2 in reprogramming by inducing nanog. Cell Stem Cell. Nov. 6, 2009;5(5):491-503.
Iellem et al., Unigue chemotactic response profile and specific expression of chemokine receptors CCR4 and CCR8 by CD4(+)CD25(+) regulatory T cells. J Exp Med. Sep. 17, 2001;194(6):847-53.
Irintchev et al., Formation of Skeletal Muscle After Subcutaneous Implantation of Cultured Myoblasts. Bio/Technology. p. 366, Abstract 153.06, Jun. 1995.
Irvine et al., Engineering synthetic vaccines using cues from natural immunity. Nat Mater. Nov. 2013;12(11):978-90.
Jager et al., Effector and regulatory T-cell subsets in autoimmunity and tissue inflammation. Scand J Immunol. Sep. 2010;72(3):173-84.
Jewett et al., Rapid Cu-free click chemistry with readily synthesized biarylazacyclooctynones. J Am Chem Soc. Mar. 24, 2010;132(11):3688-90.

(56) References Cited

OTHER PUBLICATIONS

Jiang et al., Click hydrogels, microgels and nanogels: emerging platforms for drug delivery and tissue engineering. Biomaterials. Jun. 2014;35(18):4969-85.
Jones et al., Preparation of 6 alpha- and 6 beta-carboxymethyl steroid conjugates and their use in radioimmunoassay for progesterone. Steroids. Mar. 1974;23(3):323-36.
Jorgensen et al., Treatment of an immortalized APC cell line with both cytokines and LPS ensures effective T-cell activation in vitro. Scand J Immunol. Nov. 2002;56(5):492-503.
Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.
Khomyakova et al., DNA or RNA oligonucleotide 2'-hydrazides for chemoselective click-type ligation with carbonyl compounds. Nucleosides Nucleotides Nucleic Acids. Jul.-Aug. 2011 30(7-8):577-84.
Kim et al., Injectable, spontaneously assembling, inorganic scaffolds modulate immune cells in vivo and increase vaccine efficacy. Nat Biotechnol. Jan. 2015;33(1):64-72.
Kim et al., Synthesis and characterization of dexamethasone-conjugated linear polyethylenimine as a gene carrier. Journal of Cellular Biochemistry. Jun. 1, 2010; 110(3):743-751.
Knight et al., Synthesis and evaluation of an 18F-labelled norbornene derivative for copper-free click chemistry reactions. Org Biomol Chern. Jun. 21, 2013;11(23):3817-25.
Koehler et al., A Diels-Alder modulated approach to control and sustain the release of dexamethasone and induce osteogenic differentiation of human mesenchymal stem cells. Biomaterials. May 2013;34(16):4150-4158.
Koo et al., Bioorthogonal copper-free click chemistry in vivo for tumor-targeted delivery of nanoparticles. Angew Chern Int Ed Engl. Nov. 19, 2012;51(47):11836-40.
Kratz, Albumin as a drug carrier: design of prodrugs, drug conjugates and nanoparticles. J Control Release. Dec. 18, 2008;132(3):171-83.
Kruisbeek et al., Proliferative assays for T cell function. Curr Protoc Immunol. May 2004;Chapter 3:Unit 3.12. 20 pages.
Kyi et al., Checkpoint blocking antibodies in cancer immunotherapy. FEBS Lett. Jan. 21, 2014;588(2):368-76.
Latz et al., TLR9 signals after translocating from the ER to CpG DNA in the lysosome. Nat Immunol. Feb. 2004;5(2):190-8.
Lee et al., Controlling Mechanical and Swelling Properties of Alginate Hydrogels Independently by Cross-Linker Type and Cross-Linking Density. Macromolecules. Apr. 2000;33(11):4291-4294.
Li et al., pH sensitive Laponite/alginate hybrid hydrogels: swelling behaviour and release Mechanism. Soft Matter. 2011;7:6231-6238.
Li et al., Recent advances of biomaterials in biotherapy. Regen Biomater. Jun. 2016;3(2):99-105.
Liederer et al., Enzymes involved in the bioconversion of ester-based prodrugs. J Pharm Sci. Jun. 2006;95(6):1177-95.
Liu et al., Selective inhibition of IDO1 effectively regulates mediators of antitumor immunity. Blood. Apr. 29, 2010;115(17):3520-30.
Liu et al., Syntheses of click PEG-dexamethasone conjugates for the treatment of rheumatoid arthritis. Biomacromolecules. Oct. 11, 2010;11 (10):2621-8.
Lutterotti et al., Antigen-specific tolerance by autologous myelin peptide-coupled cells: a phase 1 trial in multiple sclerosis. Sci Transl Med. Jun. 5, 2013;5(188):188ra75.
Maldonado et al., How tolerogenic dendritic cells induce regulatory T cells. Adv Immunol. 2010;108:111-65.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McQualter et al., Granulocyte macrophage colony-stimulating factor: a new putative therapeutic target in multiple sclerosis. J Exp Med. Oct. 1, 2001;194(7):873-82.

Mehta et al., Engineering New Approaches to Cancer Vaccines. Cancer Immunol Res. Aug. 2015;3(8):836-43.
Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
MGI, Mouse Facts. Retrieved online at: http://www.informatics.jax.org/mgihome/other/mouse_facts1.shtml. 2 pages. Jul. 31, 2018.
Neves et al., Imaging cell surface glycosylation in vivo using "double click" chemistry. Bioconjug Chern. Jun. 19, 2013;24(6):934-41.
Ning et al., Protein modification by strain-promoted alkyne-nitrone cycloaddition. Angew Chern Int Ed Engl. Apr. 12, 2010;49(17):3065-8.
Nogueira De Francischi et al., Inhibition by rapamycin of leukocyte migration and bronchial hyperreactivity induced by injection of Sephadex beads to guinea-pigs. Br J Pharmacol. Dec. 1993;110(4):1381-6.
Nuttelman et al., Dexamethasone-functionalized gels induce osteogenic differentiation of encapsulated hMSCs. J Biomed Mater Res A. Jan. 2006;76(1):183-95.
Oneto et al., Implantable biomaterial based on click chemistry for targeting small molecules. Acta Biomaterialia. 2014;10:5099-5105.
Pajonk et al., From sol-gel to aerogels and cryogels. J Non Cryst Solids. May 1990;121(1-3):66-67.
Patterson et al., Differential binding of chemokines to macrophages and neutrophils in the human inflamed synovium. Arthritis Res. 2002;4(3):209-14.
Flatten et al., Cancer Immunotherapy by Targeting IDO1/TDO and Their Downstream Effectors. Front Immunol. Jan. 12, 2015;5:673. 7 pages.
Prnewswire, GlaxoSmithKline and Amplimmune Form Global Strategic Collaboration. Alliance to Focus on AMP-224 for Cancer and Other Diseases. 3 pages, Aug. 4, 2010.
Quintana et al., Autoantibody patterns in diabetes-prone NOD mice and in standard C57BU6 mice. J Autoimmun. Nov. 2001;17(3):191-7.
Rautio et al., Prodrugs: design and clinical applications. Nat Rev Drug Discov. Mar. 2008;7(3):255-70.
Research Results of National Institute of Advanced Industrial Science and Technology, retrieved online at: http://www.aist.go.jp/aist_j/press_release/pr2006/pr20060719.html. 4 pages, (2006).
Ribas et al., Phase III randomized clinical trial comparing tremelimumab with standard-of-care chemotherapy in patients with advanced melanoma. J Clin Oncol. Feb. 10, 2013;31(5):616-22.
Rosenberg et al., Impact of cytokine administration on the generation of antitumor reactivity in patients with metastatic melanoma receiving a peptide vaccine. J Immunol. Aug. 1, 1999;163(3):1690-5.
Rossin et al., Diels-Alder reaction for tumor pretargeting: in vivo chemistry can boost tumor radiation dose compared with directly labeled antibody. J Nucl Med. Nov. 2013;54(11):1989-95.
Rossin et al., In vivo chemistry for pretargeted tumor imaging in live mice. Angew Chern Int Ed Engl. Apr. 26, 2010;49(19):3375-8.
Santini et al., A controlled-release microchip. Nature. Jan. 28, 1999;397(6717):335-8.
Saxon et al., Cell surface engineering by a modified Staudinger reaction. Science. Mar. 17, 2000;287(5460):2007-10.
Serafini et al., High-dose granulocyte-macrophage colony-stimulating factor-producing vaccines impair the immune response through the recruitment of myeloid suppressor cells. Cancer Res. Sep. 1, 2004;64(17):6337-43.
Shapiro et al., Sizing it up: cellular MRI using micron-sized iron oxide particles. Magn Reson Med. Feb. 2005;53(2):329-38.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Sletten et al., A bioorthogonal quadricyclane ligation. J Am Chern Soc. Nov. 9, 2011;133(44):17570-3.

(56) References Cited

OTHER PUBLICATIONS

Sletten et al., A hydrophilic azacyclooctyne for Cu-free click chemistry. Org Lett. Jul. 17, 2008;10(14):3097-9.
Sonawane et al., Chloride accumulation and swelling in endosomes enhances DNA transfer by polyamine-DNA polyplexes. J Biol Chern. Nov. 7, 2003;278(45):44826-31.
Stockmann et al., Exploring isonitrile-based click chemistry for ligation with biomolecules. Organic & Biomolecular Chemistry. 2011;9:7300-7302.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007 ;67(5):2351-9.
Tang et al., Combining radiation and immunotherapy: a new systemic therapy for solid tumors? Cancer Immunol Res. Sep. 2014;2(9):831-8.
Thelin et al., In Vivo Enrichment of Diabetogenic T Cells. Diabetes. Aug. 2017;66(8):2220-2229.
Thornton et al., Shape retaining injectable hydrogels for minimally invasive bulking. J Urol. Aug. 2004;172(2):763-8.
Tripathi et al., Elastic and macroporous agarose-gelatin cryogels with isotropic and anisotropic porosity for tissue engineering. J Biomed Mater Res A. Sep. 1, 2009;90(3):680-94.
Udono, Cancer immunotherapy with blocking of immune checkpoint. Journal of Okayama Medical Association. Apr. 2013;125:13-18.
Uni Prof KB/Swiss-Prot Accession No. Q61885.1, Feb. 13, 2019.
Van Berkel et al., Metal-free triazole formation as a tool for bioconjugation. Chembiochem. Sep. 3, 2007;8(13):1504-8.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Von Mehren et al., The influence of granulocyte macrophage colony-stimulating factor and prior chemotherapy on the immunological response to a vaccine (ALVAC-CEA B7.1) in patients with metastatic carcinoma. Clin Cancer Res. May 2001;7(5):1181-91.
Webber et al., Controlled release of dexamethasone from peptide nanofiber gels to modulate inflammatory response. Biomaterials. Oct. 2012;33(28):6823-32.
Weeks et al., The effects of chemokine, adhesion and extracellular matrix molecules on binding of mesenchymal stromal cells to poly(l-lactic acid). Cytotherapy. Oct. 2012;14(9):1080-8.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Wu et al., Intraperitoneal administration of poly(l:C) with polyethylenimine leads to significant antitumor immunity against murine ovarian tumors. Cancer Immunol Immunother. Aug. 2011;60(8):1085-96.
Xiong et al., Transcription Factor STAT3 as a Novel Molecular Target for Cancer Prevention. Cancers (Basel). Apr. 16, 2014;6(2):926-57.
Zhang et al., Generation of a syngeneic mouse model to study the effects of vascular endothelial growth factor in ovarian carcinoma. Am J Pathol. Dec. 2002;161(6):2295-309.
Zhao et al., A cell-permeable Stat3 SH2 domain mimetic inhibits Stat3 activation and induces antitumor cell effects in vitro. J Biol Chern. Nov. 12, 2010;285(46):35855-65.
Zhou et al., Instability of the transcription factor Foxp3 leads to the generation of pathogenic memory T cells in vivo. Nat Immunol. Sep. 2009;10(9):1000-7.
Zhou et al., Peptide-labeled quantum dots for imaging GPCRs in whole cells and as single molecules. Bioconjug Chern. Mar.-Apr. 2007;18(2):323-32.
Zizzari et al., The Macrophage Galactose-Type C-Type Lectin (MGL) Modulates Regulatory T Cell Functions. PLoS One. Jul. 6, 2015;10(7):e0132617. 12 pages.
Japanese Office Action for Application No. 2016-565339, dated Jan. 8, 2019. 9 pages.
U.S. Appl. No. 14/185,494, filed Feb. 20, 2014, U.S. Pat. No. 9,381,235, Issued.
U.S. Appl. No. 16/121m988, filed Sep. 5, 2018, Pending.
U.S. Appl. No. 14/223,759. fo;ed Mar. 24, 2014. U.S. Pat. No. 9,132,210, Issued.
U.S. Appl. No. 16/170,313, filed Oct. 25, 2018, Pending.
U.S. Appl. No. 15/303,985, filed Oct. 13, 2016, 2017-0042995, Published.
U.S. Appl. No. 12/867,426, filed Jan. 13, 2012, 2012-0100182. Allowed.
U.S. Appl. No. 15/135,255, filed Apr. 21, 2016, 2016-0220667, Allowed.
U.S. Appl. No. 15/345,131, filed Nov. 7, 2016, 2017-0182138, Published.
Singh et al.. Hydrogels and scaffolds for immunomodulation. Adv Mater. Oct. 2014;26(38):6530-41.
Springer et al., The lymphocyte function-associated LFA-1, CD2, and LFA-3 molecules: cell adhesion receptors of the immune system. Annu Rev Immunol. 1987;5:223-52.
Steenblock et al., A comprehensive platform for ex vivo T-cell expansion based on biodegradable polymeric artificial antigen-presenting cells Mol Ther. Apr. 2008;16(4):765-72.
Steenblock et al.. An artificial antigen-presenting cell with paracrine delivery of IL-2 impacts the magnitude and direction of the T cell response. J Biol Chern Oct. 7, 2011;286(40):34883-92.
Sunshine et al.. Particle shape dependence of CD8+ T cell activation by artificial antigen presenting cells. Biomaterials. Jan. 2014;35(1):269-277.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 Car-T cells of defined CD4+:CD8+ composition in adult B cell ALL patients. J Clin Invest. Jun. 1, 2016;126(6):2123-38.
Wang et al.. Mouse CD229 Ligation Co-stimulates T Cell Activation. The Journal of Immunology. May 2012;188(suppl 1):176.7.
Wegmann et al., Polyethyleneimine is a potent mucosal adjuvant for viral glycoprotein antigens. Nat Biotechnol. Sep. 2012;30(9):883-8.
Yee et al., Melanocyte destruction after antigen-specific immunotherapy of melanoma: direct evidence of t cell-mediated vitiligo. J Exp Med Dec. 4, 2000;192(11): 1637-44.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
U.S. Appl. No. 15/434,781, filed Feb. 16, 2017, 2017-0246281, Published.
U.S. Appl. No. 13/386,950, filed Jan. 25, 2012, U.S. Pat. No. 8,728,456, Issued.
U.S. Appl. No. 13/386,950, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Published.
U.S. Appl. No. 15/564,905, filed Oct. 6, 2017, 2018-0164298, Published.
U.S. Appl. No. 16/316,778, filed Jan. 10, 2019, 2019-0292517, Published.

(56) References Cited

OTHER PUBLICATIONS

U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, 2019-0125849, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Published.
U.S. Appl. No. 16/033,025, filed Jul. 11, 2018, 2019-0076373, Published.
U.S. Appl. No. 14/394,552, filed Oct. 15, 2014, U.S. Pat. No. 9,937,249, Issued.
U.S. Appl. No. 15/935,392, filed Mar. 26, 2018, 2018-0344821, Published.
U.S. Appl. No. 14/394,552, filed Oct. 13, 2016, 2017-0042995, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, 2018-0289789, Published.
U.S. Appl. No. 15/563,878, filed Oct. 2, 2017, 2018-0117171, Published.
U.S. Appl. No. 15/546,852, filed Jul. 27, 2017, 2018-0021253, Published.
U.S. Appl. No. 16/075,937, filed Aug. 6, 2018, 2019-0060525, Published.
Anderson et al. Crosslinking CD3 with CD2 using sepharose-immobilized antibodies enhances T lymphocyte proliferation. Cell Immunol. Sep. 1988;115(2):246-56.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120 (1):205-17.
Bierer et al., T cell receptors: adhesion and signaling. Adv Cancer Res. 1991;56:49-76.
Bjork et al., Tuning the shape of mesoporous silica particles by alterations in parameter space: from rods to platelets. Langmuir. Nov. 5, 2013;29(44):13551-61.
Brodie et al., In vivo migration and function of transferred HIV-1-specific cytotoxic T cells. Nat Med. Jan. 1999;5(1):34-41.
Damle et al., Stimulation via the CD3 and CD28 molecules induces responsiveness to IL-4 in CD4+CD29+CD45R-memory T lymphocytes. J Immunol. Sep. 1, 19895;143(6):1761-7.
Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma Clin Cancer Res. Dec. 15, 2010;16(24):6122-31.
Fadel et al., A carbon nanotube-polymer composite for T-cell therapy. Nat NanotechnoL Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Carlie et al., T cells coactivated with immobilized anti-CD3 and anti-CD28 as potential immunotherapy for cancer. J Immunother. Jul. 1999;22(4):336-45.
Gimmi et al., B-cell surface antigen B7 provides a costimulatory signal that induces T cells to proliferate and secrete nterleukin 2. Proc Natl Acad Sci U S A. Aug. 1, 1991;88(15):6575-9.
Harding et al., CD28-mediated signalling co-stimulates murine T cells and prevents induction of anergy in T-cell clones. Nature. Apr. 16, 1992;356(6370):607-9.
Hasan et al.. Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al.. Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
June et al., Adoptive cellular therapy: a race to the finish line. Sci Transl Med. Mar. 25, 2015;7(280):280ps7.
June et al., The B7 and CD28 receptor families. Immunol Today. Jul. 1994; 15(7):321-31.
Kupferschmidt et al., Mesoporous silica particles potentiate antigen-specific T-cell responses. Nanomedicine (Lond). 2014;9(12):1835-46.
Lee et al., The immunological synapse balances T cell receptor signaling and degradation. Science. Nov. 14, 2003;302(5648):1218-22.
Levine et al., Effects of CD28 costimulation on long-term proliferation of CD4+ T cells in the absence of exogenous feeder cells. J Immunol. Dec. 15, 1997;159(12):5921-30.
Li et al., Mesoporous silica nanoparticles in biomedical applications. Chem Soc Rev. Apr. 7, 2012;41(7):2590-605.
Li et al., The effect of surface modification of mesoporous silica micro-rod scaffold on immune cell activation and nfiltration. Biomaterials. Mar. 2016;83:249-56.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Mahony et al., Mesoporous silica nanoparticles act as a self-adjuvant for ovalbumin model antigen in mice. Small. Sep. 23, 2013;9(18):3138-46.
Mandal et al., Polymer-based synthetic dendritic cells for tailoring robust and multifunctional T cell responses. ACS Chem Biol. Feb. 20, 2015;10(2):485-92.

(56) References Cited

OTHER PUBLICATIONS

Mangsbo et al., Enhanced tumor eradication by combining CTLA-4 or PD-1 blockade with CpG therapy. J Immunother. Apr. 2010;33(3):225-35.

Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.

McKay et al.. Click chemistry in complex mixtures: bioorthogonal bioconjugation. Chem Biol. Sep. 18, 2014;21(9):1075-101.

Melief et al., T-cell immunotherapy of tumors by adoptive transfer of cytotoxic T lymphocytes and by vaccination with minimal essential epitopes. Immunol Rev. Jun. 1995;145:167-77.

Meng et al.. Use of a lipid-coated mesoporous silica nanoparticle platform for synergistic gemcitabine and paclitaxel delivery to human pancreatic cancer in mice. ACS Nano 2015,9(4):3540-57.

Meyer et al.. Biodegradable nanoellipsoidal artificial antigen presenting cells for antigen specific T-cell activation. Small. Apr. 2015; 11(13):1519-25.

NCBI, MeSH. Nivolumab. Retrieved online at: https://fwww.ncbi.nlm.nih/gov/mesh/?term=nivolumab. 3 pages, (2010).

NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).

Perica et al.. Enrichment and Expansion with Nanoscale Artificial Antigen Presenting Cells for Adoptive Immunotherapy. ACS Nano Jul. 28, 2015;9(7):6861-71.

Oin et al., CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared To Those Containing CD28. Blood. 2013;122:1431.

Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.

Riddell et al., Principles for adoptive T cell therapy of human viral diseases. Annu Rev Immunol. 1995;13:545-86.

Riddell et al., Restoration of viral immunity in immunodeficient humans by the adoptive transfer of T cell clones. Science Jul. 10, 1992;257(5067):238-41.

Riddell et al., The use of anti-CD3 and anti-CD28 monoclonal antibodies to clone and expand human antigen-specific T cells. J Immunol Methods Apr. 17, 1990;128(2):189-201.

Rosenberg et al., Adoptive cell transfer as personalized immunotherapy for human cancer. Science. Apr. 3, 2015;348(6230):62-8.

Rosenberg et al., Durable complete responses in heavily pretreated patients with metastatic melanoma using T-cell transfer immunotherapy Clin Cancer Res. Jul. 1, 2011;17(13):4550-7.

Rubbi et al., Evidence of surface antigen detachment during incubation of cells with immunomagnetic beads. J mmunol Methods. Dec. 3, 1993;166(2):233-41.

Schwartz, A cell culture model for T lymphocyte clonal anergy. Science. Jun. 15, 1990;248(4961):1349-56.

Sheppard et al., Polyethyleneimine is a potent systemic adjuvant for glycoprotein antigens. Int Immunol. Oct. 2014;26(10):531-8.

Shibuya et al., Anti-CD3/anti-CD28 bead stimulation overcomes CD3 unresponsiveness in patients with head and neck squamous cell carcinoma Arch Otolaryngol Head Neck Surg. Apr. 2000;126(4):473-9.

Andersson et al., HSP70 promoter-driven activation of gene expression for immunotherapy using gold nanorods and near infrared light. Vaccines (Basel). Mar. 25, 2014;2(2):216-27.

Bhardwaj et al., TLR Agonists: Are They Good Adjuvants? Cancer J. 2010;16(4):382-391.

Casanova et al., Human Mannose-binding Lectin in Immunity: Friend, Foe, or Both?. J Exp Med. 2004;199(10):1295-1299.

Chao et al., Morphological control on SBA-15 mesoporous silicas via a slow self-assembling rate. J Mater Sci. 2009;44:6453-62.

Che et al., Synthesis and characterization of chiral mesoporous silica. Nature. May 20, 2004;429(6989):281-4.

Chen et al., Enhanced humoral and cell-mediated immune responses generated by cationic polymer-coated PLA microspheres with adsorbed HBsAg. Mol Pharm. Jun. 2, 2014;11(6):1772-84.

Chen et al.. Morphological control of mesoporous silica SBA-15 synthesized at low temperature without additives. J Porous Mater. 2011;18:211-6.

Chen et al., Quantitative proteomic profiling of pancreatic cancer juice. Proteomics. Jul. 2006;6(13):3871-9.

Cheung et al., Engineered Materials for Cancer Immunotherapy. Nano Today. Aug. 1, 2015;10(4):511-531.

Cheung et al.. Scaffolds that mimic antigen-presenting cells enable ex vivo expansion of primary T cells. Nat Biotechnol. Feb. 2018;36(2):160-169.

Choi et al., Facile synthesis of high quality mesoporous SBA-15 with enhanced control of the porous network connectivity and wall thickness. Chern Commun (Camb) Jun. 21, 2003;(12):1340-1.

Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.

Del Chiaro et al., Early detection and prevention of pancreatic cancer: is it really possible today? World J Gastroenterol. Sep. 14, 2014;20(34):12118-31.

Dengler et al., Mesoporous silica-supported lipid bilayers (protocells) for DNA cargo delivery to the spinal cord. J Control Release. Jun. 10, 2013;168(2):209-24.

Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.

Eggermont et al., Towards efficient cancer immunotherapy: advances in developing artificial antigen-presenting cells. Trends Biotechnol. Sep. 2014;32(9):456-65.

Gao et al., Immune cell recruitment and cell-based system for cancer therapy. Pharm Res. Apr. 2008;25(4):752-68.

Grabowska et al., Systemic in vivo delivery of siRNA to tumours using combination of polyethyleneimine and Yansferrin-polyethyleneimine conjugates. Biomater Sci. Nov. 2015;3(11):1439-48.

Han et al.. Synthesis of rod-like mesoporous silica using mixed surfactants of cetyltrimethylammonium bromide and cetyltrimethylammonium chloride as templates. Materials Letters 2003;57:4520-4.

Jiang, Application of polymers in nucleic acid delivery. Thesis in partial fulfillment of the requirements for the Doctor oi Philosophy degree in Pharmacy in the Graduate College of The University of Iowa 138 pages, Dec. 2011.

Johansson, Controlling the Pore Size and Morphology of Mesoporous Silica. Linkoping Studies in Science and Technology Licentiate Thesis No. 1451, 53 pages, (2010).

John et al., Passive and active mechanisms trap activated CD8+ T cells in the liver. J Immunol. May 1, 2004; 172(9):5222-9.

Kosuge et al., Morphological Control of Rod- and Fiberlike SBA-15 Type Mesoporous Silica Using Water-Soluble Sodium Silicate Chem Mater. 2004;16:899-905.

Lacy et al., Cytokine release from innate immune cells: association with diverse membrane trafficking pathways. Blood 2011;118(1):9-18.

Liu et al., Fecal markers, intestinal inflammation and inflammatory enteritis. Clinical Journal of Digestive Disease. 2003;15(6):275-7.

Liu et al., Porous nanoparticle supported lipid bilayers (protocells) as delivery vehicles. J Am Chern Soc. Feb. 4, 2009;131(4):1354-5.

Millar et al., Prediction of local recurrence, distant metastases, and death after breast-conserving therapy in early-stage invasive breast cancer using a five-biomarker panel. J Clin Oncol Oct. 1, 2009;27(28):4701-8.

Milone et al., Powered and controlled T-cell production. Nat Biomed Eng. Mar. 2018;2(3):148-150.

(56) References Cited

OTHER PUBLICATIONS

Mu et al.. Identification and characterization of a mannose-binding lectin from Nile tilapia (Oreochromis niloticus). Fish Shellfish Immunol 2017;67:244-253.

Qiao et al.. Synthesis and Bio-adsorptive Properties of Large-Pore Periodic Mesoporous Organosilica Rods. Chem Mater. 2005;17:6172-6.

Stanley et al., Transjugular intrahepatic portosystemic shunt as a treatment for protein-losing enteropathy caused by portal hypertension. Gastroenterology. Dec. 1996;111(6):1679-82.

Stephen et al.. Biopolymer implants enhance the efficacy of adoptive T-cell therapy. Nat Biotechnol. Jan. 2015;33(1):97-101.

Sunshine et al.. Nanoengineering approaches to the design of arlificial antigen-presenting cells. Nanomedicine. 2013;8(7):1173-89.

Takamura et al., Regulatory role of lymphoid chemokine CCL19 and CCL21 in the control of allergic rhinitis. J Immunol. 2007;179(9):5897-5906.

Thielemann et al., Pore structure and surface area of silica SBA-15: influence of washing and scale-up. Beilstein J Nanotechnol. 2011;2:110-8.

Yu, Designed synthesis of mono-dispersed silica-based nanostructures and their applications in drug/gene delivery. A thesis submitted for the degree of Doctor of Philosophy at The University of Queensland in 2014, 196 pages.

\* cited by examiner

**Elastic Modulus
Day 7**

**Fracture Toughness
Day 7** in vitro void formation

Ki-67 Expression (green)

in vitro cell release

DNA Synthesis

Porogen degree of oxidation

Extent of porogen crosslinking

Standard Pore-Forming Saline
Hydrogel Hydrogel

Microcomputed Tomography (week 4)

60 kPa

10 RGD / alginate polymer

Proliferation (Ki-67; green) Day 50

Cell Deployment and proliferation *in vivo*

**Strategy to create injectable, cell encapsulating hydrogels that form pores *in situ***

Porogen Fabrication and Characterization

Modifying Porogen Chemistry to control chemokine-mediated cell recruitment

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: adhesive peptide amino acid motif

<400> SEQUENCE: 1

Pro His Ser Arg Asn
1               5

<210> SEQ ID NO 2
<211> LENGTH: 4
<212> TYPE: PRT
<213> ORGANISM: Artificial Sequence
<220> FEATURE:
<223> OTHER INFORMATION: adhesive peptide amino acid motif

<400> SEQUENCE: 2

Asp Gly Glu Ala
1
```

INJECTABLE, PORE-FORMING HYDROGELS FOR MATERIALS-BASED CELL THERAPIES

RELATED APPLICATIONS

This application is a national stage application, filed under 35 U.S.C. § 371, of International Application No. PCT/US2011/055174, filed Oct. 6, 2011, which claims the benefit of priority under 35 U.S.C. § 119(e) to U.S. Provisional Application No. 61/390,594, filed on Oct. 6, 2010, which is incorporated herein by reference in their entireties.

STATEMENT AS TO FEDERALLY SPONSORED RESEARCH

This invention was made with Government support under NIH R37DE013033 awarded by the National Institutes of Health and MRSEC DMR-0820484 awarded by the National Science Foundation. The Government has certain rights in the invention.

INCORPORATION-BY-REFERENCE OF SEQUENCE LISTING

The contents of the text file named "29297-082N01US_ST25.txt", which was created on Jul. 10, 2013 and is 1 KB in size, is hereby incorporated by reference in their entirety.

FIELD OF THE INVENTION

This invention relates to biocompatible hydrogel compositions.

BACKGROUND OF THE INVENTION

Over the recent decades, biocompatible polymers have been used to form scaffolds that act as carriers for cell transplantation, or to recruit host cell populations into the device.

SUMMARY OF THE INVENTION

The invention provides compositions and methods to form porous hydrogels. For example, pores are formed in situ within hydrogels following hydrogel injection into a subject. Pores that are formed in situ via degradation of sacrificial porogens within the surrounding hydrogel (bulk hydrogel) facilitate recruitment or release of cells. For example, the resulting pore is within 5% of the size of the initial porogen.

Disclosed herein is a material that is not initially porous, but which becomes macroporous over time resident in the body of a recipient animal such as a mammalian subject. These compositions are associated with significant advantages over earlier scaffold compositions. The hydrogels described herein are well-suited to initially protect transplanted cells from host inflammatory responses, and then release transplanted cells after inflammation has subsided (e.g., after 12 hours, or 1, 3, 5, 7, or 10 days or more post-transplantation, i.e. resident in the body of the recipient). The hydrogels described herein also double as a surgical bulking agent, further minimizing inflammation in the host, and then later releasing cells.

Accordingly, the invention provides a composition comprising a first hydrogel and a second hydrogel, wherein the first hydrogel degrades at least 10% faster (e.g., at least 15%, at least 20%, at least 25%, at least 30%, at least 35%, at least 40%, at least 45%, or at least 50% faster) than the second hydrogel and wherein either the first hydrogel or the second hydrogel (or both) comprises an isolated cell. Preferably, the first hydrogel comprises a porogen that degrades leaving a pore in its place. For example, the first hydrogel is a porogen and the resulting pore after degradation insitu is within 25% of the size of the initial porogen, e.g., within 20%, within 15%, or within 10% of the size of the initial porogen. Preferably, the resulting pore is within 5% of the size of the initial porogen. The first hydrogel degrades more rapidly than the second hydrogel, because the first hydrogel is more soluble in water (comprises a lower solubility index). Alternatively, the first hydrogel degrades more rapidly because it is cross-linked to protease-mediated degradation motifs as described in U.S. Ser. No. 10/980,989 to Zilla, incorporated herein by reference).

The molecular mass of the polymers used to form the first hydrogel composition (a porogen) are approximately 50 kilodaltons (kDa), and the molecular mass of the polymers used to form the second hydrogel composition (bulk) comprises approximately 250 kDa. A shorter polymer (e.g. that of a porogen) degrades more quickly compared to that of a longer polymer (e.g., that of the bulk composition). Alternatively, a composition is modified to render it more hydrolytically degradable by virtue of the presence of sugar groups (e.g., approximately 3-10% sugar of an alginate composition). In another example, the porogen hydrogel is more enzymatically degradable compared to the bulk hydrogel. The composite (first and second hydrogel) composition is permeable to bodily fluids, e.g., such as enzyme which gain access to the composition to degrade the porogen hydrogel. In some cases, the second hydrogel is cross-linked around the first hydrogel, i.e., the porogens (first hydrogel) are completely physically entrapped in the bulk (second) hydrogel.

Cells or bioactive factors (e.g., growth factors such as granulocyte/macrophage colony stimulating factor (GM-CSF), vascular endothelial growth factor (VEGF), condensed oligonucleotides, e.g., CpG, or plasmid DNA) are optionally encapsulated either into the porogen phase, bulk hydrogel phase, or into both phases. The porogens degrade in situ over a time-course pre-determined by the user. Upon degradation of the porogens, cells are released from or may migrate into the material. However, because they initially lack pores, pore-forming hydrogels are useful to provide mechanical support immediately after formation. Suitable bioactive factors include vascular endothelial growth factor (e.g., VEGFA; GenBank Accession Number: (aa) AAA35789.1 (GI:181971), (na) NM_001171630.1 (GI:284172472), incorporated herein by reference), acidic fibroblast growth factor (aFGF, Genbank Accession Number: (aa) AAB29057.2 (GI:13236891), (na) NM_000800.3 (GI:222144219), incorporated herein by reference), basic fibroblast growth factor (bFGF; GenBank Accession Number: (aa) AAB21432.2 (GI:8250666), (na) A32848.1 (GI:23957592), incorporated herein by reference), placenta growth factor (PlGF or PLGF; GenBank Accession Number: (aa) AAH07789.1 (GI:14043631), (na) NM_002632.4 (GI:56676307), incorporated herein by reference), leptin (Genbank Accession Number: (aa) CBI71013.1 (GI:285310289), (na) NM_000230.2 (GI:169790920), incorporated herein by reference), hematopoietic growth factor (e.g., HGF, Genbank Accession Number: (aa) AAA64297.1 (GI:337938), (na) NM_000601.4 (GI:58533168), incorporated herein by reference), VEGF receptor-1 (VEGFR-1, Genbank Accession Number: (aa) NP_002010.2 (GI:156104876), incorporated herein by reference), VEGFR-2 (Genbank Accession Number: (aa) AAC16450.1 (GI:3132833), (na) EU826563.1 (GI:194318421), incorporated herein by reference), transforming growth factor-β (TGF-β, Genbank Accession Number: (aa) AAA36738.1 (GI:339564), (na) NM_000660.4 (GI:260655621), incorporated herein by reference), bone morphogenetic protein (e.g., BMP-4, Genbank Accession Number: (aa) NP_570912.2 (GI:157276597), (na) NM_001202.3 (GI:157276592), incorporated herein by reference), insulin-like growth factor (IGF-1, Genbank Accession Number: (aa) CAA01954.1 (GI:1247519), (na) NM_001111283.1 (GI:163659898), incorporated herein by reference), fibroblast growth factor-2 (FGF-2), platelet-derived growth factor (PDGF; GenBank Accession Number: (aa) AAA60552.1 (GI:338209), (na) NM_033023.4 (GI:197333759), incorporated herein by reference), epidermal growth factor (EGF, Genbank Accession Number: (aa) AAH93731.1 (GI:62740195), incorporated herein by reference), transforming growth factor-α (TGF-α, Genbank Accession Number: (na) NM_003236.2 (GI:153791671), incorporated herein by reference), nerve growth factor (NGF, Genbank Accession Number: (aa) AAH32517.2 (GI:34192369), (na) NM_002506.2 (GI:70995318), incorporated herein by reference), brain-derived neurotrophic factor (BDNF, Genbank Accession Number: (aa) CAA62632.1 (GI:987872), (na) NM_170731.4 (GI:219842281), incorporated herein by reference), neurotrophin-3 (NT-3, Genbank Accession Number: (aa) NP_001096124.1 (GI:156630995), (na) NM_001102654.1 (GI:156630994), incorporated herein by reference), ciliary neurotrophic factor (CNTF, Genbank Accession Number: (aa) AAB31818.1 (GI:633830), (na) NM_000614.3 (GI:209574322), incorporated herein by reference), and glial cell line-derived neurotrophic factor (GDNF, Genbank Accession Number: (aa) CAG46721.1 (GI:49456801), (na) NM_000514.3 (GI:299473777), incorporated herein by reference). Other suitable factors include anti-VEGF antibody, anti-aFGF antibody, anti-bFGF antibody, anti-PlGF antibody, anti-leptin antibody, anti-HGF antibody, anti-VEGFR-1 antibody, anti-VEGFR-2 antibody, batimastat (BB-94), marimastat (BB-2516), thalidomide, O-(chloroacetylcarbamoyl)-fumagillol (TNP-470), carboxyamidotriazole (CAI), mitoxantrone, doxorubicin, SU5416, anti-TGF-β antibody, anti-BMP antibody, anti-IGF-1 antibody, anti-FGF-2 antibody, anti-PDGF antibody, anti-EGF antibody, anti-TGF-α antibody, and anti-VEGF antibody. Other bioactive factors suitable for encapsulation either into the porogen phase, bulk hydrogel phase, or into both phases include FMS-like tyrosine kinase 3 ligand (Flt3 ligand; Genbank Accession Number: (aa) AAI44040 (GI:219519004), (na) NM_004119 (GI:GI:121114303), incorporated herein by reference), anti-flt3 ligand, hepatocyte growth factor (Genbank Accession Number: (aa) AAB20169 (GI:237997), incorporated herein by reference), and stromal derived factor 1 (SDF-1).

Alternatively, an adenovirus is optionally encapsulated either into the porogen phase, bulk hydrogel phase, or into both phases. For example, the adenovirus encodes runt-related transcription factor (e.g., Runx2; Genbank Accession Number: (aa) CAI13532 (GI:55959066), (na) NM_001024630 (GI:226442782), incorporated herein by reference), a key transcription factor associated with osteoblast differentiation. In another aspect, the adenovirus encodes MyoD (Genbank Accession Number: (aa) CAA40000 (GI:34862), (na) NM_002478 (GI:77695919), incorporated herein by reference), a protein with a key role in regulating muscle differentiation. Alternatively, the adenovirus encodes bone morphogenetic protein, e.g., BMP-2 (Genbank Accession Number: (aa) AF040249_1 (GI:6649952), (na) NM_001200 (GI:80861484), incorporated herein by reference) or BMP-4 (Genbank Accession Number: (aa) NP_570912.2 (GI:157276597), (na) NM_001202.3 (GI:157276592), incorporated herein by reference). BMP-2 is involved in, inter alia, bone repair, while BMP-4 is involved in the repair of cardiac tissue. In one aspect, an adenovirus that encodes Runx and an adenovirus that encodes BMP-2 are encapsulated into the hydrogel.

Cells suitable for being encapsulated either into the porogen phase, bulk hydrogel phase, or into both phases include mesenchymal stem cells, myoblasts, vascular progenitor cells (e.g., an outgrowth endothelial cell), differentiated cells derived from embryonic stem cells or induced pluripotent stem cells, induced pluripotent cells, or cells that were directly reprogrammed from a fibroblast to a differentiated state.

In some examples, the porogen composition comprises cells, and in other examples, the bulk composition comprises cells. If cells are present in the composition (e.g., having been seeded during fabrication), the cells are deployed out of the composition after administration into a mammalian subject. Alternatively, the composition does not comprise cells; however, upon administration into tissues of a mammalian subject (e.g., implantation into a human patient), cells are recruited into the composition. The mammal can be any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human. Alternatively, the subject can be a non-mammalian animal such as xenopus, salamander, or newt.

The invention provides methods of deploying cells from a scaffold into tissues of a mammalian subject, comprising administering to a subject a composition comprising a first hydrogel and a second hydrogel, wherein the first hydrogel degrades at least 10% faster than the second hydrogel, and wherein the composition lacks pores at the time of administration, and wherein the composition comprises pores following residence in said subject, and wherein the first hydrogel or the second hydrogel comprises an isolated cell.

A methods of recruiting cells into a scaffold in vivo is carried out by administering to a subject a composition comprising a first hydrogel and a second hydrogel, wherein the first hydrogel degrades at least 10% faster than the second hydrogel and wherein the composition lacks pores at the time of administration, but comprises pores following residence in the subject. For example, pores are created due to the relative degradability or solubility of a first hydrogel composition compared to a second hydrogel composition, e.g., a porogen composition compared to a bulk composition.

Porosity influences recruitment and/or egress of the cells from the composition. Pores are nanoporous, microporous, or macroporous. For example, the diameter of nanopores is less than about 10 nm. Micropores are in the range of about 100 nm to about 20 μm in diameter. Macropores are greater than about 20 μm (e.g., greater than about 100 μm or greater than about 400 μm). Exemplary macropore sizes include 50 μm, 100 μm, 150 μm, 200 μm, 250 μm, 300 μm, 350 μm, 400 μm, 450 μm, 500 μm, 550 μm, and 600 μm. Macropores are those of a size that permit a eukaryotic cell to traverse into or out of the composition. In one example, a macroporous composition has pores of about 400 μm to 500 μm in diameter. The preferred pore size depends on the application. For example, for cell deployment and cell release, the preferred pore diameter is greater than 50 µm.

The size of the porogen is related to the size of the overall composite material. For example, for the material to stay intact, the porogen diameter is <10% of the smallest dimension of the overall composite. The density of porogens is between 10-80 percent of the overall volume of the composite composition. For example, the density of porogen is between 15% and 75%, between 20% and 70%, between 25% and 65%, between 30% and 60%, or between 35% and 55% of the overall volume. Preferably, the density of porogens is at least 50% of the overall volume to achieve optimal cell recruitment to the hydrogel or cell release from the hydrogel.

The hydrogel has an elastic modulus of between about 10 to about 1,000,000 Pascals (e.g., from about 10 to about 100,000 Pa, from about 10 to about 150,000 Pa, from about 10 to about 200,000 Pa, from about 10 to about 300,000 Pa, from about 10 to about 400,000 Pa, from about 10 to about 500,000 Pa, from about 10 to about 600,000 Pa, from about 10 to about 700,000 Pa, from about 10 to about 800,000 Pa, or from about 10 to about 900,000 Pa). Preferably, the slowly-degrading hydrogel comprises an elastic modulus of about 20 kilo Pa to 60 kPa, e.g., 25 kPa to 55 kPa, 30 kPa to 50 kPa, or 35 kPa to 45 kPa. The rapidly-degrading hydrogel comprises an elastic modulus of at least 40 kPa initially in order to maintain integrity during encapsulation prior to degradation.

Preferably, the slowly-degrading hydrogel (i.e., the second hydrogel or "bulk") comprises high molecular weight peptides with an amino acid sequence of RGD which mimic cell adhesion proteins. Alternatively, the slowly-degrading hydrogel comprises a different adhesive peptide amino acid motif such as PHSRN (SEQ ID NO: 1) or DGEA (SEQ ID NO: 2). For example, the slowly-degrading hydrogels are preferably modified with 2-10 RGD peptides/polymer (e.g., alginate polymer).

By "hydrogel" is meant a composition comprising polymer chains that are hydrophilic. Exemplary hydrogels are comprised of materials that are compatible with cell encapsulation such as alginate, polyethylene glycol (PEG), PEG-acrylate, agarose, and synthetic protein (e.g., collagen or engineered proteins (i.e., self-assembly peptide-based hydrogels). For example, a commercially available hydrogel includes BD™ PuraMatrix™. BD™ PuraMatrix™ Peptide Hydrogel is a synthetic matrix that is used to create defined three dimensional (3D) micro-environments for cell culture.

For example, the hydrogel is a biocompatible polymer matrix that is biodegradable in whole or in part. Examples of materials which can form hydrogels include alginates and alginate derivatives, polylactic acid, polyglycolic acid, poly (lactic-co-glycolic acid) (PLGA) polymers, gelatin, collagen, agarose, natural and synthetic polysaccharides, polyamino acids such as polypeptides particularly poly (lysine), polyesters such as polyhydroxybutyrate and poly-epsilon.-caprolactone, polyanhydrides; polyphosphazines, poly(vinyl alcohols), poly(alkylene oxides) particularly poly (ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone), and copolymers of the above, including graft copolymers. Synthetic polymers and naturally-occurring polymers such as, but not limited to, collagen, fibrin, hyaluronic acid, agarose, and laminin-rich gels may also be used.

A preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g., $Ca^{+2}$, $Mg^{+2}$, $Ba^{+2}$) and form stable hydrogels when exposed to these molecules.

The compositions described herein are suitable for clinical use, e.g., bone repair, regeneration, or formation; muscle repair, regeneration, or formation; and dermal repair, regeneration, or formation. For example, the compositions are applied to bone fractures alone or together with a bone adhesive (cement) or glue or to diseased or injured muscle tissue. The hydrogels (seeded with cells or without cells) are injected at the site of disease, injury, or fracture (in the case of bone or cartilage). For example, the hydrogels are injected into or onto bone. Exemplary bioactive factors for use in promoting bone or cartilage repair, regeneration, or formation include BMP-2, BMP-4, or RunX.

In some cases, the composition recruits cells to promote bone or cartilage repair, regeneration, or formation. Alternatively, the first hydrogel or the second hydrogel comprises an isolated bone cell selected from the group consisting of an osteoblast, an osteocyte, an osteoclast, and an osteoprogenitor. Alternatively, the first hydrogel or the second hydrogel comprises an isolated cartilage cell, wherein the isolated cartilage cell comprises a chondroblast. The isolated bone cell or an isolated cartilage cell is an autologous cell or an allogeneic cell.

For muscle applications, e.g., muscle tears, muscle strains, or muscle pulls, the hydrogels (seeded with or without cells) are injected at the site of injury. Suitable compositions for muscle applications include a composition comprising a first hydrogel and a second hydrogel, wherein the first hydrogel degrades at least 10% faster than the second hydrogel, and wherein the first hydrogel or the second hydrogel comprises a bioactive factor for use in muscle repair, regeneration, or formation. For example, the bioactive factor comprises MyoD.

In some cases, the composition recruits cells to promote muscle or cartilage repair, regeneration, or formation. Alternatively, the first hydrogel or the second hydrogel comprises an isolated muscle cell selected from the group consisting of a skeletal muscle cell, a cardiac muscle cell, a smooth muscle cell, and a myo-progenitor cell. The isolated muscle cell is an autologous cell or an allogeneic cell.

For dermal applications, e.g., burns, abrasions, lacerations, or disease, the hydrogels (seeded with cells or without cells) are applied directly to the site as poultice or wound dressing. Preferably, the majority of porogens (e.g., more than 50%, more than 60%, more than 70%, more than 80%, or more than 90%) within the bulk hydrogels are directed toward the skin surface and into the skin tissue when applied directly to the site (e.g., the burn). In this manner, the bioactive factors or cells are released into the surface of the skin or lower layers of the skin, and do not migrate away from the skin or target tissue. An exemplary bioactive factor for use in skin repair, regeneration, or formation is FGF.

In some cases, the composition recruits cells to promote skin or cartilage repair, regeneration, or formation. Alternatively, the first hydrogel or the second hydrogel comprises an isolated skin cell selected from the group consisting of a fibroblast, a dermal cell, an epidermal cell, or a dermal progenitor cell. The isolated skin cell is an autologous cell or an allogeneic cell.

Bioactive factors such as polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

An "isolated nucleic acid" is a nucleic acid, the structure of which is not identical to that of any naturally occurring nucleic acid, or to that of any fragment of a naturally occurring genomic nucleic acid spanning more than three separate genes. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybridgene, i.e., a gene encoding a fusion protein. Isolated nucleic acid molecules according to the present invention further include molecules produced synthetically, as well as any nucleic acids that have been altered chemically and/or that have modified backbones.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 2 is a series of photographs, line graphs, and schematics illustrating mesenchymal stem cell deployment in-vitro. Specifically, FIG. 2 demonstrates stem cell release from pore-forming hydrogels in vitro, which also shows that release can be tuned by varying the composition of porogens and the compartmentalization of cells within porogens versus bulk.

FIG. 3 is a series of photographs and line graphs showing the results of controlling mesenchymal stem cell deployment, engraftment and proliferation in vivo. Specifically, FIG. 3 demonstrates stem cell release from pore-forming hydrogels in vivo within the subcutaneous space of nude mice.

FIG. 4A-FIG. 4C are fluorescent micrographs of GFP-expressing myoblasts and outgrowth endothelial cells (OECs) adherent to tissue culture plastic after 4 days of culture within pore-forming hydrogels in which the chemistry used to form porogens was varied and the different cell types were initially placed into distinct compartments: (FIG. 4A): myoblasts in bulk component, OECs in porogen component; (FIG. 4B): myoblasts in bead component, OECs in porogen component; (FIG. 4C): both myoblasts and OECs in bulk component. FIG. 4D is a representative micrograph of a plastic substrate on which equal numbers of GFP-myoblasts and OECs were seeded. Myoblasts outgrew OECs. Cells were stained with Ethidium Homodimer (red), so that GFP-myoblasts appear yellow and OECs appear red. Images taken at 10× magnification.

FIG. 5 shows the controlling chemokine-mediated cell recruitment by pore-forming hydrogels in vivo. Alginate was first oxidized and then reduced with sodium borohydride to make alcohol groups that replace what were originally sugars. FIG. 5A and FIG. 5B are fluorescent micrographs of dendritic cell recruitment into (FIG. 5A) standard, injectable alginate gel, and (FIG. 5B) pore-forming hydrogel. Both sets of hydrogels were loaded with 2 pg of granulocyte-macrophage colony stimulating factor. FIGS. 5C and 5D are fluorescent micrographs of dendritic cell recruitment into pore-forming hydrogels fabricated with (FIG. 5C) oxidized or (FIG. 5D) reduced porogens. No chemokine was added. For histology, dendritic cells are stained for CD11c (green) and NIHC-II (red), with Hoescht nuclear counterstain (blue). In FIG. 5C and FIG. 5D, only nuclear staining (white) was performed. This figure shows the difference in host cell recruitment by materials with porogens formed from the oxidized alginate vs. reduced alginate.Scale bars: 100 pm.

FIG. 6 is a series of line graphs, bar charts, and photographs demonstrating the control of stem cell proliferation within pore-forming hydrogels, deployment from hydrogels, and ability to regenerate bone by varying bulk phase composition. FIG. 6E is a line graph showing the quantification of the relative radiant efficiency (proportional to cell density) of mCherry-MSC injected in pore-forming hydrogels in which the bulk phase was modified with either 2 (♦), or 10 (■) RGD peptides per alginate polymer. Alternatively, cells were injected in a standard hydrogel with 2 RGD peptides/alginate polymer (▲). FIG. 6F shows the quantification of the percentage of healing (new bone formation due to human MSC transplanted into Nude Rat cranial defects) as a function of the method of MSC delivery. Error bars are SEM, n=4-6.

FIG. 7 is a series of line graphs and bar frequency charts showing the mechanical properties and in-vitro degradation of hydrogels formed from binary alginates.

DETAILED DESCRIPTION OF THE INVENTION

Figure 1A:
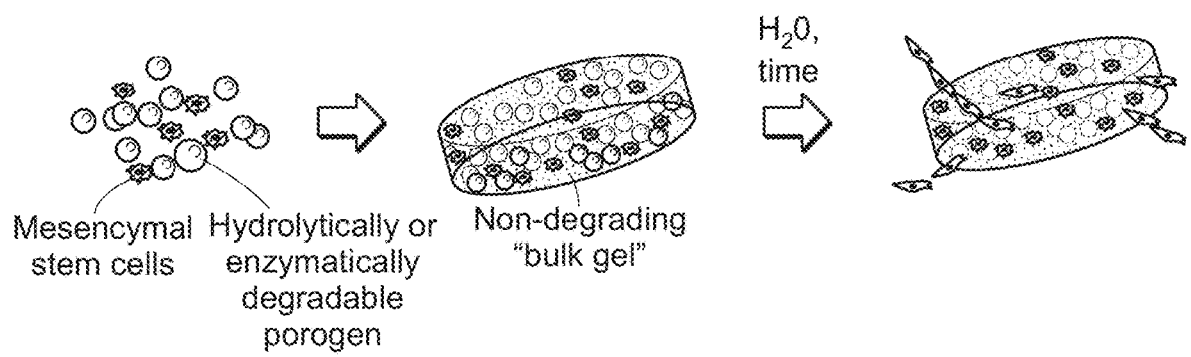
FIG. 1A is a schematic illustrating the formation of hydrogels. Left: micro-beads comprised of rapidly degradable hydrogels (red spheres) and mesenchymal stem cells (MSCs; green). Middle: micro-beads and MSCs are mixed with a second hydrogel forming polymer material ("bulk gel;" gray), which is crosslinked around the beads. Right: after degradation of the micro-beads in situ, an intact hydrogel network remains with a network of pores through which MSCs are released.
Figure 1B:
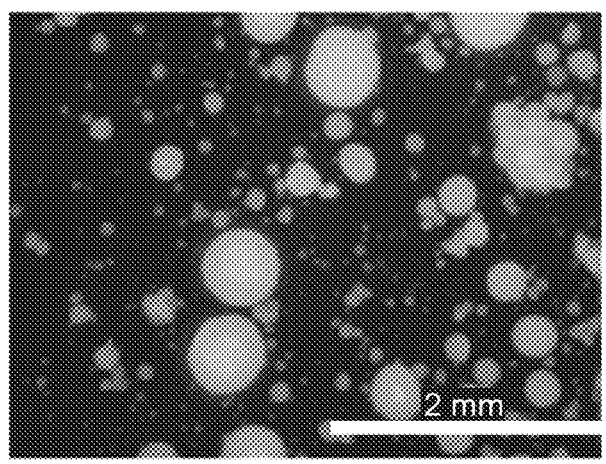
FIG. 1B is a fluorescence micrograph of fluorescein (green) labeled porogens immediately after fabrication.
Figure 1C:
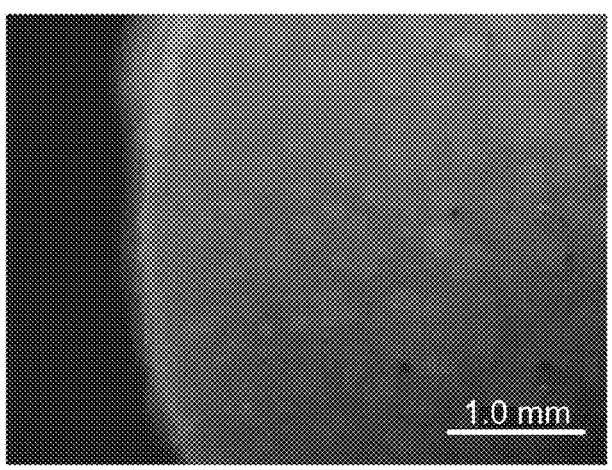
FIG. 1C is a fluorescence micrograph of fluorescein (green) labeled porogens after encapsulation into an alginate hydrogel network.
Figure 1D:
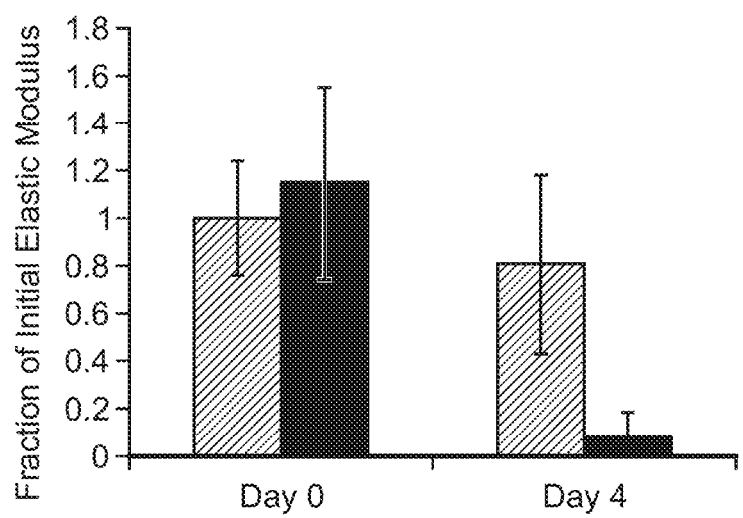
FIG. 1D is a bar graph illustrating elastic modulus measurements of either standard hydrogels (blue bars) or pore-forming hydrogels (red bars). At day 0, there is no statistically significant difference in the overall rigidity of pore-forming composites and standard hydrogels because pores have not formed; however, after 4 days, the modulus of the composite drops substantially because of pore formation.

Over the recent decades, biocompatible polymers have been used to form scaffolds that act as carriers for cell transplantation, or to recruit host cell populations into the device. Generally, sponges such as poly(lactide-co-glycolide) (PLGA), or synthetic hydrogels such as alginate are used. However, both sets of materials have disadvantages. For example, sponges typically adsorb serum proteins, so it is difficult to control presentation of adhesive proteins or peptides (for example, RGD) from the material. Sponge materials also typically are not amenable to injection, and require an invasive surgery for implantation, and also expose transplanted or host cells to a host environment that may initially be hostile (for example, neutrophils present during inflammation may attack stem cells). On the other hand, synthetic hydrogels are typically injectable, allowing minimally-invasive delivery, and do not interact with proteins. However, prior to the invention described herein, the pore size in hydrogels was typically much smaller than the diameter of a eukaryote cell, making it difficult to expand a transplanted cell population, release transplanted cells to allow them to repair damaged tissues, or recruit host cells into the device.

The present invention comprises a method to form pores in situ within hydrogels following hydrogel injection. Pores form in situ via degradation of sacrificial porogens encapsulated within the surrounding hydrogel. The kinetics and onset of pore formation are controlled by manipulating material used to form porogens, and cells are encapsulated either into the porogens themselves or the hydrogel surrounding them. Examples demonstrate in vitro deployment, proliferation, and differentiation of stem cells, as well as in vivo stem cell deployment and chemokine-mediated cell recruitment. The system mediates controlled deployment of cells out of, or local recruitment of cells into, a polymer matrix via formation of pores within this matrix. The size, distribution, and formation kinetics of the pores are predetermined by the user, while the integrity of the matrix surrounding pores, along with cells or biological factors inside this matrix, are unchanged.

Accordingly, described herein is the use of insoluble cues such as hydrogel adhesion ligand presentation and/or elastic modulus (i.e., stiffness) to generate materials which are 1) injectable; 2) allow the user to control cell fate using insoluble cues; and 3) form pores over time to deploy or recruit cells. Specifically, the methods described herein create pore-forming hydrogels, using a process that allows cells to be encapsulated into either the pore-forming phase (hereafter referred to as "porogen") or the non- or slowly-degrading phase (hereafter referred to as "bulk").

The invention provides methods for a generalized approach to create pore-forming hydrogels that allow cell encapsulation, and a means to control the kinetics of cell deployment out of, or recruitment into, the hydrogel. Hydrogel micro-bead "porogens" are formed, and are next encapsulated into a second, "bulk" hydrogel. The composition of polymers used to form porogen and bulk hydrogels may be varied; however, the porogen must degrade more rapidly (e.g., 10%, 20%, 50%, 2×, 5×, 10×, 20× or faster) than the bulk hydrogel. Cells or bioactive factors (e.g., growth factors such as granulocyte/macrophage colony stimulating factor (GM-CSF), vascular endothelial growth factor (VEGF), condensed oligonucleotides, e.g., CpG, or plasmid DNA) are optionally encapsulated either into the porogen phase, bulk hydrogel phase, or into both phases. The porogens degrade in situ over a time-course pre-determined by the user, at which point cells are released, or may migrate into the material. However, because they initially lack pores, pore-forming hydrogels are useful to provide mechanical support immediately after formation (FIG. 1).

Figure 5:
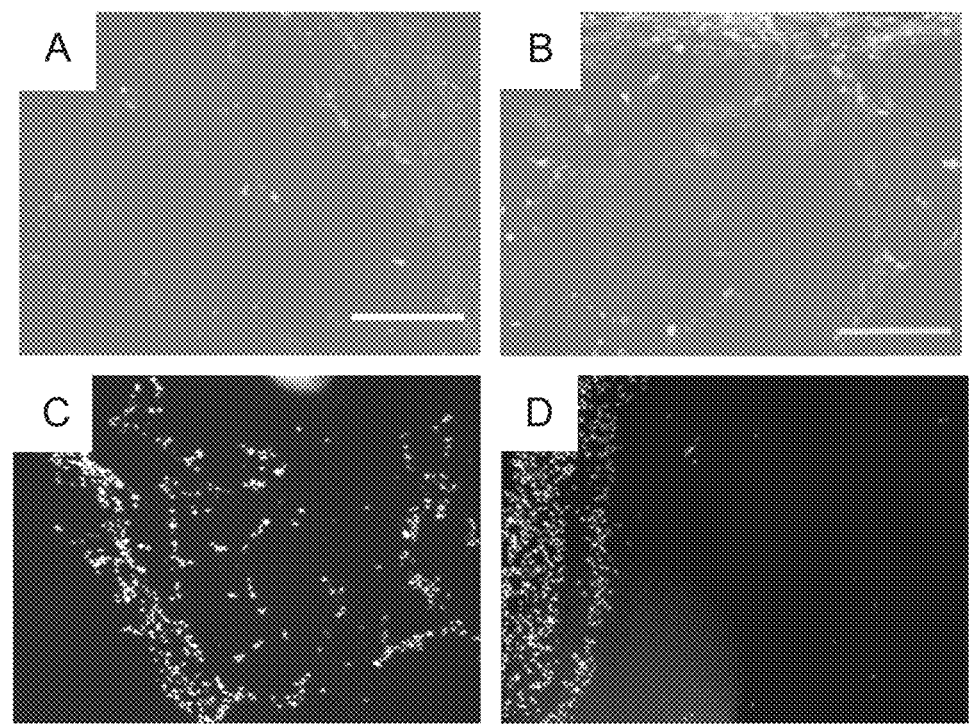
FIG. 5 is a series of photomicrographs depicting using pore-forming hydrogels for chemokine-mediated cell recruitment. Specifically.

Cellular release or recruitment is manipulated by controlling the kinetics of porogen degradation. For example, the alginate polymers are oxidized to produce alginate dialdehyde, and the total number of cells released increases as the extent of oxidation increases (FIG. 2, FIG. 3). Alternatively, conditions used to crosslink the porogens are altered to manipulate the time at which significant porogen degradation and cell release begin to occur (FIG. 2). Porogen chemistry can further be varied to facilitate, or inhibit, interaction with host proteins (FIG. 5).

Cell release and cell fate are controlled by manipulating the biophysical and biochemical properties (e.g. elastic modulus and density of integrin-binding adhesion peptides such as RGD) of the bulk hydrogel. For example, pore formation, bulk hydrogel RGD density and bulk hydrogel elasticity all affect cell proliferation within these materials (FIG. 2, FIG. 6). The orthogonal processing of porogens and bulk separate from one another enhances the ability to tune the system to manipulate cell release and cell fate. For example, stem cell lineage commitment is modulated by varying elastic modulus or RGD density, independent of the kinetics of pore formation. In contrast, other techniques used to form macro-porous materials (e.g. solvent-based extraction of porogens) are not compatible with cell encapsulation, and typically affect the physical properties of both the porogen and bulk phases. The physical and biochemical properties rapidly degrading bulk hydrogel materials change continuously over the course of degradation. These parameters are harnessed to design the bulk phase to regulate cell fate.

Hydrogel Compositions

Hydrogels comprise a network of polymer chains that are hydrophilic. Hydrogel (also called aquagel) is sometimes found as a colloidal gel in which water is the dispersion medium. Hydrogels are highly absorbent (they can contain over 99.9% water) natural or synthetic polymers. Hydrogels also possess a degree of flexibility very similar to natural tissue, due to their significant water content. Hydrogel is comprised of cross-linked polymers. Exemplary hydrogels are comprised materials that are compatible with cell encapsulation such as alginate, polyethylene glycol (PEG), PEG-acrylate, agarose, and synthetic protein (e.g., collagen or engineered proteins (i.e., self-assembly peptide-based hydrogels). For example, a commercially available hydrogel includes BD™ PuraMatrix™ Peptide Hydrogel, which is a synthetic matrix that is used to create defined three dimensional (3D) micro-environments for cell culture.

For example, the hydrogel is a biocompatible polymer matrix that is biodegradable in whole or in part. Examples of materials which can form hydrogels include alginates and alginate derivatives, polylactic acid, polyglycolic acid, poly (lactic-co-glycolic acid) (PLGA) polymers, gelatin, collagen, agarose, natural and synthetic polysaccharides, polyamino acids such as polypeptides particularly poly (lysine), polyesters such as polyhydroxybutyrate and poly-epsilon.-caprolactone, polyanhydrides; polyphosphazines, poly(vinyl alcohols), poly(alkylene oxides) particularly poly (ethylene oxides), poly(allylamines)(PAM), poly(acrylates), modified styrene polymers such as poly(4-aminomethylstyrene), pluronic polyols, polyoxamers, poly(uronic acids), poly(vinylpyrrolidone), and copolymers of the above, including graft copolymers. Synthetic polymers and naturally-occurring polymers such as, but not limited to, collagen, fibrin, hyaluronic acid, agarose, and laminin-rich gels may also be used.

A preferred material for the hydrogel is alginate or modified alginate material. Alginate molecules are comprised of (1-4)-linked β-D-mannuronic acid (M units) and α L-guluronic acid (G units) monomers, which can vary in proportion and sequential distribution along the polymer chain. Alginate polysaccharides are polyelectrolyte systems which have a strong affinity for divalent cations (e.g., $Ca^{+2}$, $Mg^{+2}$, $Ba^{+2}$) and form stable hydrogels when exposed to these molecules.

Synthetic hydrogels are typically injectable, allow for minimally-invasive delivery, and do not interact with proteins. Hence, the presentation of adhesion proteins or peptides is precisely controlled. Moreover, synthetic hydrogels typically have a pore mesh size that is much smaller than cells (<10 nm, whereas cells are >10 um), which prevents host cells from attacking transplanted cells. However, this small pore size also prevents transplanted cells from proliferating extensively within the material, and also precludes their eventually being released to affect various functions (for example, regeneration of functional tissue or destruction of diseased tissue).

Several techniques have been introduced to combine desirable features of hydrogels and sponges—for example, rigid microspheres have been encapsulated into hydrogels, and then extracted with solvents (e.g. acetone) to leave behind a macroporous hydrogel, and freeze-drying has been applied to generate macroporous hydrogels. Hydrogels can be modified to rapidly degrade in vivo to release host cells. However, prior to the invention described herein, none of the approaches allowed for the combination of a non-degrading (or slowly degrading) material component with cell encapsulation. The mechanical properties and biochemical composition of hydrogel materials strongly affect cell fate, and degradation in-and-of itself may intrinsically regulate cell fate.

Pore-Forming Compositions

Hydrogel micro-beads ("porogens") are formed. Next, porogens are encapsulated into a "bulk" hydrogel that is either non-degradable or which degrades at a slow rate compared to the porogens. Cells are optionally encapsulated either into the porogen or bulk compartment. Immediately after hydrogel formation, or injection into the desired site in vivo, the composite material lacks pores, and serves as a surgical bulking agent. Subsequently, porogen degradation causes pores to form in situ, and encapsulated cells deploy away from the composite material and into surrounding tissues or remote tissues, e.g., lymph nodes, in the body. The size and distribution of pores are controlled during porogen formation, and mixing with the polymers which form the bulk hydrogel.

Alternatively, the hydrogel is injected without encapsulated cells, and pore formation is used as a means of recruiting host cells, in combination or independent of chemokines released from either the bulk or porogen component. The porogens are comprised of any biocompatible polymer, as long as they degrade more rapidly than the material used to form the "bulk" hydrogel, and are initially mechanically stable enough to withstand being mixed with the polymer which forms the bulk hydrogel phase. The "bulk" is comprised of any hydrogel-forming polymer.

Alginate Compositions

The polymers utilized in the compositions and methods are naturally-occurring or synthetically made. In one example, both the porogens and bulk hydrogels are formed from alginate. "Alginate" as that term is used here, refers to any number of derivatives of alginic acid (e.g., calcium, sodium or potassium salts, or propylene glycol alginate). See, e.g., PCT/US97/16890, hereby incorporated by reference.

The alginate polymers suitable for porogen formation have a Dalton molecular weight from 5,000 to 500,000 Da. The polymers are optionally further modified (e.g., by oxidation with sodium periodate, (Bouhadir et al., 2001, Biotech. Prog. 17:945-950, hereby incorporated by reference), to facilitate rapid degradation. In the examples described below, the polymers were crosslinked by extrusion through a nebulizer with co-axial airflow into a bath of divalent cation (for example, Ca2+ or Ba2+) to form hydrogel micro-beads. The higher the airflow rate, the lower the porogen diameter.

The concentration of divalent ions used to form porogens may vary from 5 to 500 mM, and the concentration of polymer from 1% to 5% by weight. However, any method which produces porogens that are significantly smaller than the bulk phase is suitable. Porogen chemistry can further be manipulated to produce porogens that have a some interaction with host proteins and cells (e.g., alginates oxidized to an extent of >5% of sugar resides interact significantly with host cells, FIG. 5), or to inhibit this interaction (e.g., oxidized alginates that are reduced with NaBH4 exhibit minimal interaction with protein or with host cells, FIG. 5).

The alginate polymers suitable for formation of the bulk hydrogel have a Dalton molecular weight from 5,000 to 500,000 Da. The polymers may be further modified (for example, by oxidation with sodium periodate), to facilitate degradation, as long as the bulk hydrogel degrades more slowly than the porogen. The polymers may also be modified to present biological cues to control cell responses (e.g., integrin binding adhesion peptides such as RGD). Either the porogens or the bulk hydrogel may also encapsulate bioactive factors such as oligonucleotides, growth factors or drugs to further control cell responses. The concentration of divalent ions used to form the bulk hydrogel may vary from 5 to 500 mM, and the concentration of polymer from 1% to 5% by weight. The elastic modulus of the bulk polymer is tailored, e.g., to control the fate of encapsulated cells.

Example 1

Forming Pores In Situ within Hydrogels

The formation of pores in situ within hydrogels as demonstrated via imaging and mechanical properties testing is shown in FIG. 1. As shown in FIG. 1A, micro-beads comprised of rapidly degradable hydrogels (red spheres) were mixed with a second hydrogel forming polymer material, which is crosslinked around the beads. After degradation of the micro-beads in situ, an intact hydrogel network (pink) remained with a network of pores. The elastic modulus measurements of either standard hydrogels (left bars) or pore-forming hydrogels (right bars) were determined (FIG. 1D). At day 0, there was no statistically significant difference in the overall rigidity of pore-forming composites and standard hydrogels because pores have not formed; however, after 4 days, the modulus of the composite drops substantially because of pore formation.

Additional methods relevant to generating the hydrogels described herein are as follows. Bouhadir et al. Polymer 1999; 40: 3575-84 (incorporated herein by reference) describes the oxidation of alginate with sodium periodate, and characterizes the reaction. Bouhadir et al. Biotechnol. Prog. 2001; 17: 945-50 (incorporated herein by reference) describes oxidation of high molecular weight alginate to form alginate dialdehyde (alginate dialdehyde is high $M_w$ alginate in which a certain percent, (e.g., 5%), of sugars in alginate are oxidized to form aldehydes), and application to make hydrogels degrade rapidly. Kong et al. Polymer 2002; 43: 6239-46 (incorporated herein by reference) describes the use of gamma-irradiation to reduce the weight-averaged molecular weight ($M_w$) of guluronic acid (GA) rich alginates without substantially reducing GA content (e.g., the gamma irradiation selectively attacks mannuronic acid, MA blocks of alginate). Alginate is comprised of GA blocks and MA blocks, and it is the GA blocks that give alginate its rigidity (elastic modulus). Kong et al. Polymer 2002; 43: 6239-46 (incorporated herein by reference) shows that binary combinations of high $M_w$, GA rich alginate with irradiated, low $M_w$, high GA alginate crosslinks with calcium to form rigid hydrogels, but which degrade more rapidly and also have lower solution viscosity than hydrogels made from the same overall weight concentration of only high $M_w$, GA rich alginate. Alsberg et al. J Dent Res 2003; 82(11): 903-8 (incorporated herein by reference) describes degradation profiles of hydrogels made from irradiated, low $M_w$, GA-rich alginate, with application in bone tissue engineering. Kong et al. Adv. Mater 2004; 16(21): 1917-21 (incorporated herein by reference) describes control of hydrogel degradation profile by combining gamma irradiation procedure with oxidation reaction, and application to cartilage engineering.

Techniques to control degradation of hydrogen biomaterials are well known in the art. For example, Lutolf M P et al. Nat Biotechnol. 2003; 21: 513-8 (incorporated herein by reference) describes poly(ethylene glycol) based materials engineered to degrade via mammalian enzymes (MMPs). Bryant S J et al. Biomaterials 2007; 28(19): 2978-86 (U.S. Pat. No. 7,192,693 B2; incorporated herein by reference) describes a method to produce hydrogels with macro-scale pores. A pore template (e.g., poly-methylmethacrylate beads) is encapsulated within a bulk hydrogel, and then acetone and methanol are used to extract the porogen while leaving the bulk hydrogel intact. Silva et al. Proc. Natl. Acad. Sci USA 2008; 105(38): 14347-52 (incorporated herein by reference; US 2008/0044900) describes deployment of endothelial progenitor cells from alginate sponges. The sponges are made by forming alginate hydrogels and then freeze-drying them (ice crystals form the pores). These materials improve the therapeutic effect of the cells (compared to cells delivered alone), but these materials must be implanted surgically (i.e., non-injectable), are not amenable to cell encapsulation (cells will die when freeze dried), and this strategy makes it difficult to control cell fate by controlling elastic modulus. Ali et al. Nat Mater 2009 (incorporated herein by reference) describes the use of porous scaffolds to recruit dendritic cells and program them to elicit anti-tumor responses. Huebsch et al. Nat Mater 2010; 9: 518-26 (incorporated herein by reference) describes the use of hydrogel elastic modulus to control the differentiation of encapsulated mesenchymal stem cells.

Described herein is the use of insoluble cues such as hydrogel adhesion ligand presentation and/or elastic modulus (i.e., stiffness) to generate materials which are 1) injectable; 2) allow the user to control cell fate using insoluble cues; and 3) form pores over time to deploy or recruit cells. Specifically, the methods described herein create pore-forming hydrogels, using a process that allows cells to be encapsulated into either the pore-forming phase (hereafter referred to as "porogen") or the non- or slowly-degrading phase (hereafter referred to as "bulk"). In the methods described herein, the porogen degrades by hydrolysis rather than by solvents, which means that cells are encapsulated either into the porogen or the bulk gel around them, and there is very little chance that proteins or other bioactive compounds encapsulated into the gel would be denatured.

Figure 1E:
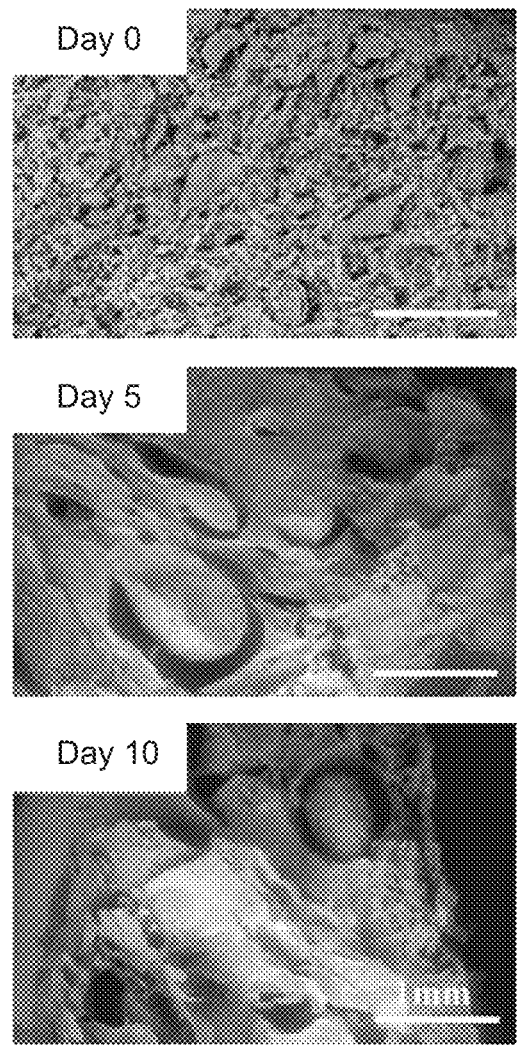
FIG. 1E is a series of scanning electron micrographs depicting pore-forming hydrogels immediately after formation (Day 0) showing a grossly intact network, 5 days after fabrication, or 10 days after fabrication, at which time significant pore formation was observed.
Figure 1F:
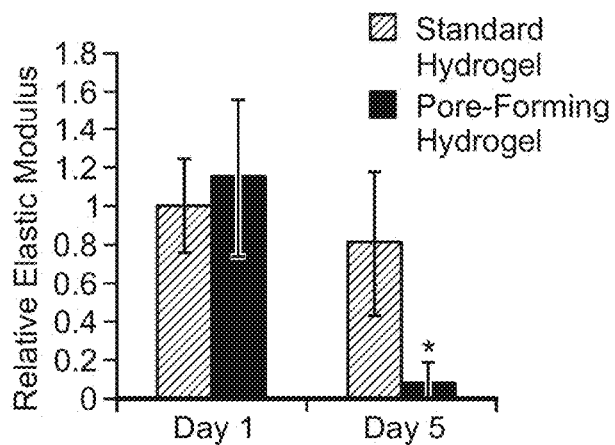
FIG. 1F and FIG. 1G verify that the elastic modulus of the composite material (50% porogen volume fraction) is not substantially different from the elastic modulus of a standard hydrogel (no porogens), but that as voids form, the modulus of the composite drops substantially. The decrease in composite elastic modulus at one week corresponds to the density of voids, and at low porogen density, there is a linear relationship between the density of voids and decrease in composite elastic modulus. Figures H and I illustrate that the fracture toughness of the composite material (25% porogen volume fraction) is initially similar to the fracture toughness of a standard hydrogel with no porogen, but shortly decreases to a fraction of the initial value. As with elastic modulus, the decrease in fracture toughness scales with the density of porogen, though in a non-linear manner. Scale bars: (B, C, and E): 1 mm.
Figure 1G:
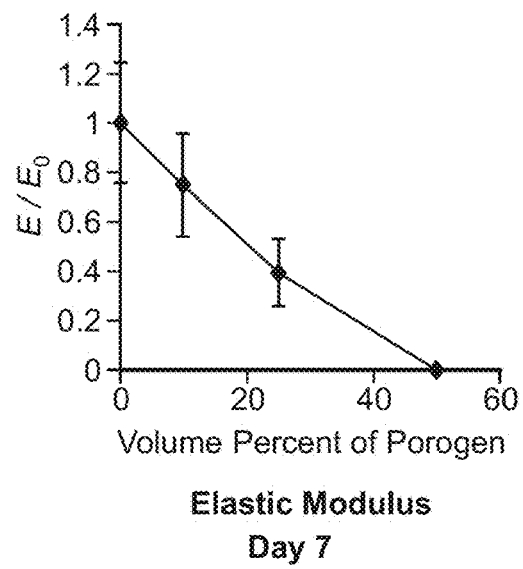
Figure 1H:
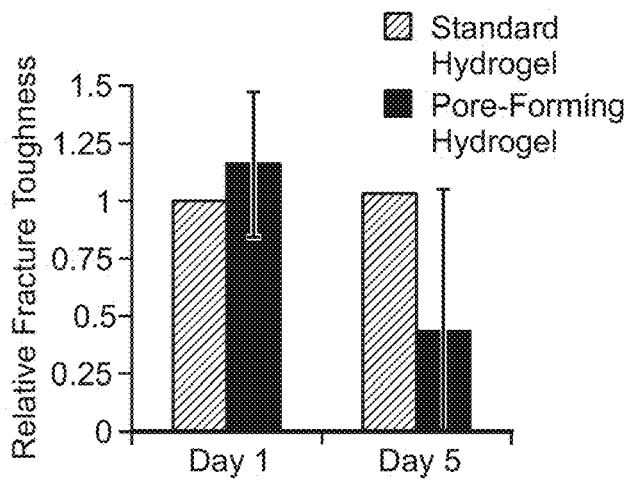
FIG. 1 is a series of schematics, photographs, bar graphs, and line graphs showing the formation of pores in situ within hydrogels as demonstrated via imaging and mechanical properties testing.
Figure 1I:
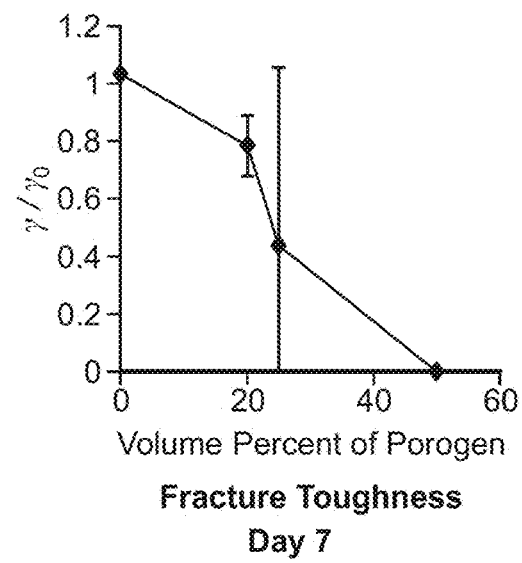

As described in detail below, porogens stayed intact during encapsulation, but rapidly degraded to yield voids that were visible by scanning electron microscopy, and resulted in loss of elastic modulus and fracture toughness of the composite materials. Specifically, scanning electron micrographs (SEM) showed that pore-forming hydrogels immediately after formation (Day 0) possessed a grossly intact network; however, by 10 days after fabrication, significant pore formation was observed (FIG. 1E). The elastic modulus of the composite material (50% porogen volume fraction) was not substantially different from the elastic modulus of a standard hydrogel (no porogens); however, as voids form, the modulus of the composite drops substantially (FIG. 1F and FIG. 1G). The decrease in composite elastic modulus at one week corresponds to the density of voids, and at low porogen density, there is a linear relationship between the density of voids and decrease in composite elastic modulus. The fracture toughness of the composite material (25% porogen volume fraction) was initially similar to the fracture toughness of a standard hydrogel with no porogen, but it decreases to a fraction of the initial value (Figures H and I). As with elastic modulus, the decrease in fracture toughness scales with the density of porogen, though in a non-linear manner. These results demonstrate that porogens stay intact during encapsulation and degrade in situ to form voids.

Example 2

In Vitro and In Vivo Release of Cells

Pore-forming hydrogels were formed by encapsulating degradable alginate porogens, along with bone marrow stromal stem cells (D1) into high molecular weight bulk alginate gel. Porogens were formed with a binary mixture of 20 mg/mL of alginate dialdehyde (theoretical oxidation of 7.5% of alginate sugar residues in high Mw, high guluronic acid content alginate) and 7.5 mg/mL high Mw, high guluronic acid (GA) content alginate. This polymer mixture was extruded through a glass nebulizer with co-axial nitrogen airflow into a bath of 0.1M $CaCl_2$ and 0.1M HEPES to crosslink polymers. Porogens were washed extensively with serum free cell culture medium. The bulk hydrogel was formed by 20 mg/mL high Mw, high GA-content alginate modified with 2 RGD peptides per alginate polymer. D1 cells and porogens were mixed into the bulk hydrogel material using syringes and then the composite was crosslinked with Calcium Sulfate. The number of D1 cells released from this system over time in vitro is shown in FIG. 2. The kinetics of release could be modified by 1) controlling the concentration of $CaCl_2$ used to form porogens, by 2) varying the composition (degree of oxidation) of porogens, and by 3) varying the compartmentalization of cells (either within porogens or within bulk gel).

Specifically, mesenchymal stem cell deployment in-vitro is illustrated in FIG. 2. Stem cells were released from pore-forming hydrogels in vitro, and this release can be tuned by varying the composition of porogens and the compartmentalization of cells within porogens versus bulk. The effects of porogen density (0-80 volume percent) on cellularity and efflux from pore-forming hydrogels are shown in FIG. 2C. Specifically, fluorescence micrographs of pore-forming hydrogels were stained for live mesenchymal stem cells (MSC) (Calcein-AM, green) or dead cells (Ethidium Homodimer, red) after 4-10 days in vitro. The spherical cell morphology denotes cells confined in a nanoporous material, and is present at short time frames in both materials, but only in standard hydrogels over longer time frames. The cumulative number of MSC released after 12 days as a function of porogen volume density is shown in FIG. 2D.

Figure 2A:
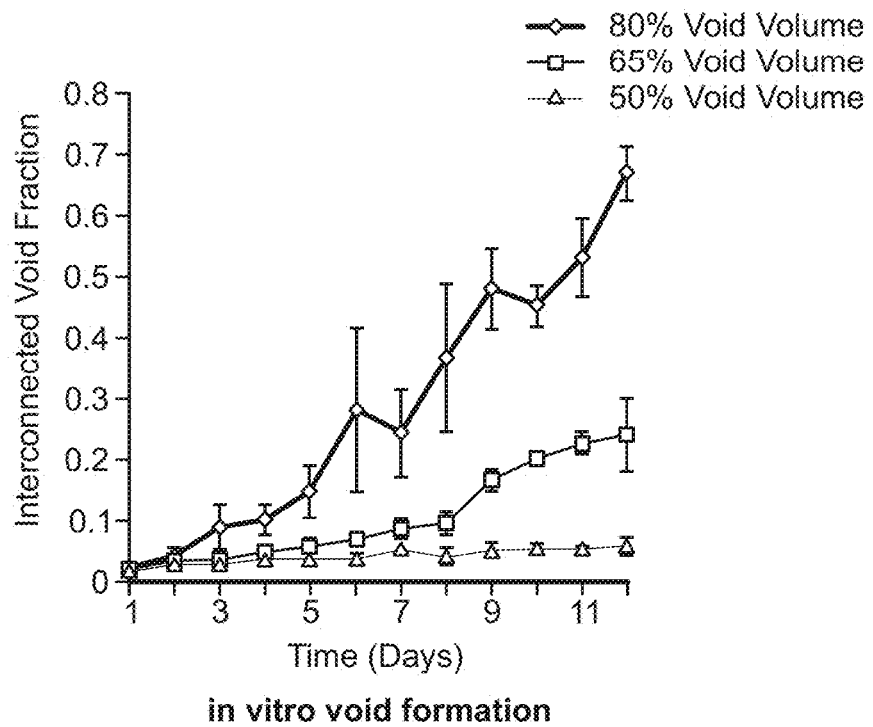
FIG. 2A is a line graph showing the kinetics of interconnected void formation assessed with a capillary assay (error bars are standard error of the mean, n=3-4). Interconnected voids formed over the first 7 days unless a very high fraction of porogens (above the percolation limit; 80%) were present. No substantial interconnected void formation was observed with a sub-percolation porogen density.
Figure 2B:
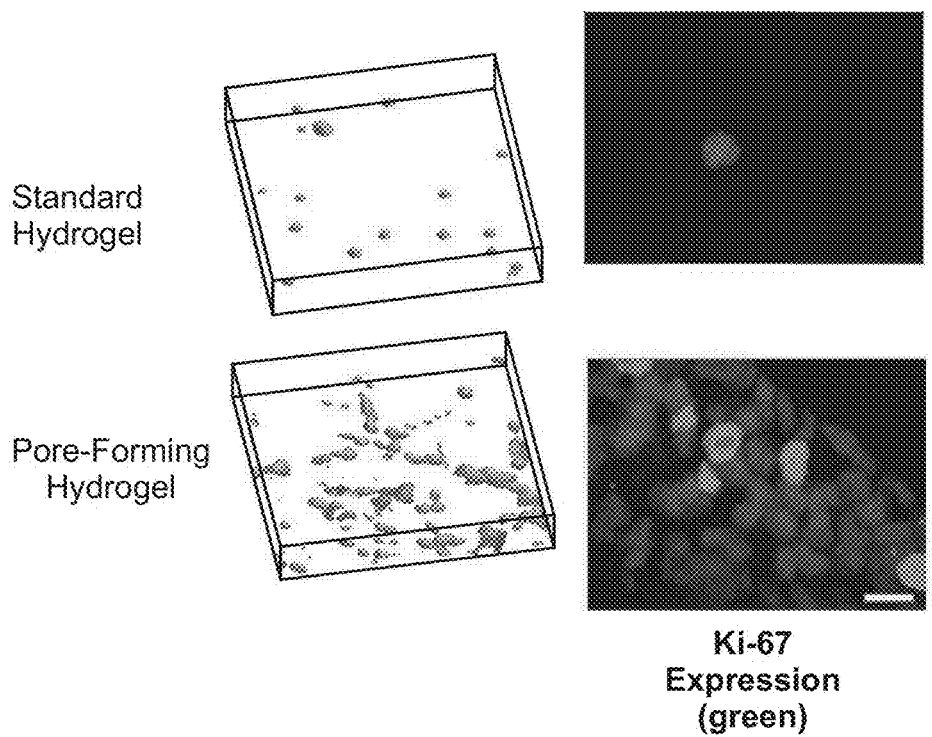
FIG. 2B is a series of schematics and photographs showing 3-dimensional reconstructions of Calcein-AM stained cells distributed throughout pore-forming hydrogels. The substantial changes in cell morphology depict the cells' ability to migrate and proliferate within pore-forming hydrogels, whereas cells remained sparse and rounded within standard hydrogels. Ki-67 immunofluorescence (green) indicates increased proliferation, while nuclear counterstain (Hoescht, blue) higher cellularity, within pore-forming hydrogels compared to standard hydrogels.
Figure 2C:
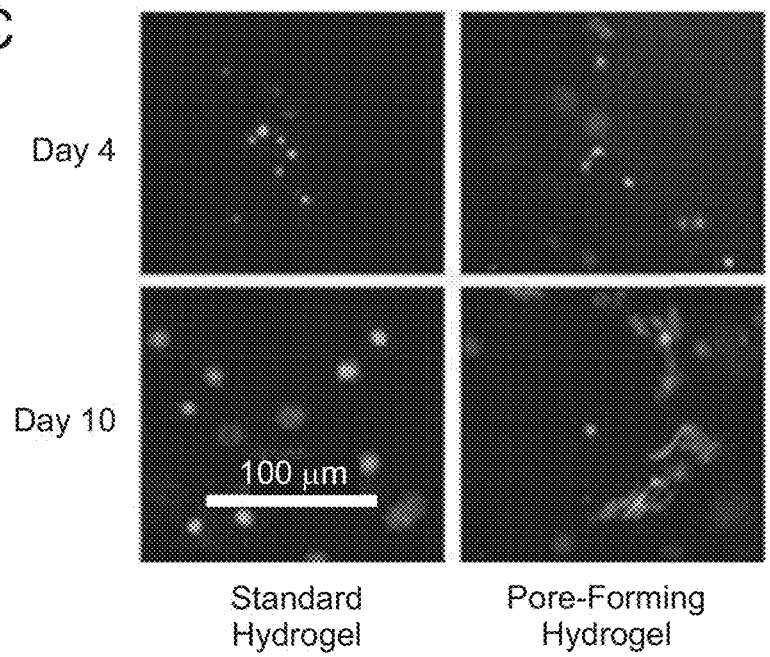
FIG. 2C is a set of fluorescence micrographs showing the effects of void formation on cellularity and cell morphology within pore forming hydrogels. Specifically, fluorescence micrographs of pore-forming hydrogels were stained for live mesenchymal stem cells (MSC) (Calcein-AM, green) or dead cells (Ethidium Homodimer, red) after 4-10 days in vitro. The spherical cell morphology denotes cells confined in a nanoporous material, and is present at short time frames in both materials, but only in standard hydrogels over longer time frames.
Figure 2D:
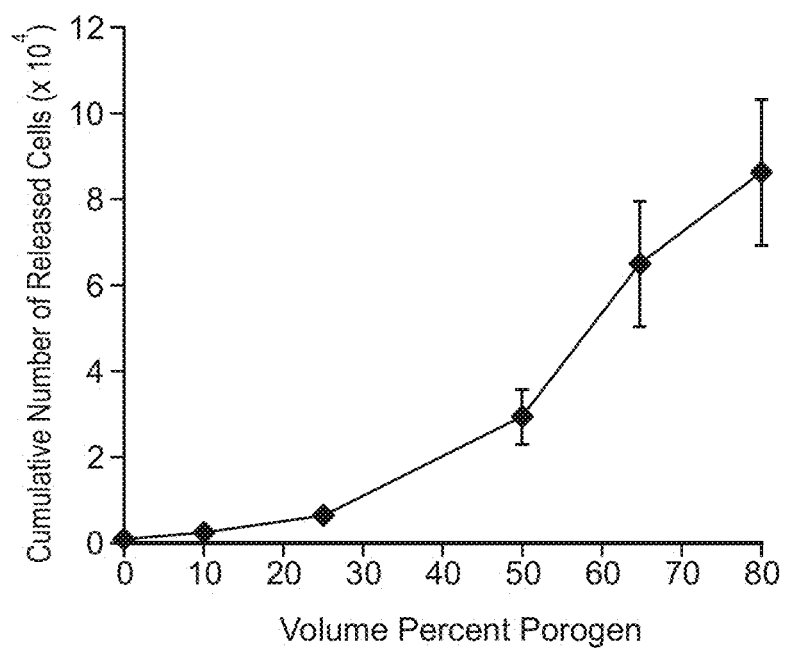
FIG. 2D is a line graph showing the cumulative number of MSC released after 12 days as a function of porogen volume density.

As shown in FIG. 2D, the size of the porogen is related to the size of the overall composite material. Specifically, for the material to stay intact, the porogen diameter is <10% of the smallest dimension of the overall composite. The density of porogens is between 10-80 percent of the overall volume for both cell recruitment and cell release, e.g., between 15% and 75%, between 20% and 70%, between 25% and 65%, between 30% and 60%, or between 35% and 55% of the overall volume. Preferably, the density of porogens is at least 50% of the overall volume.

Figure 2E:
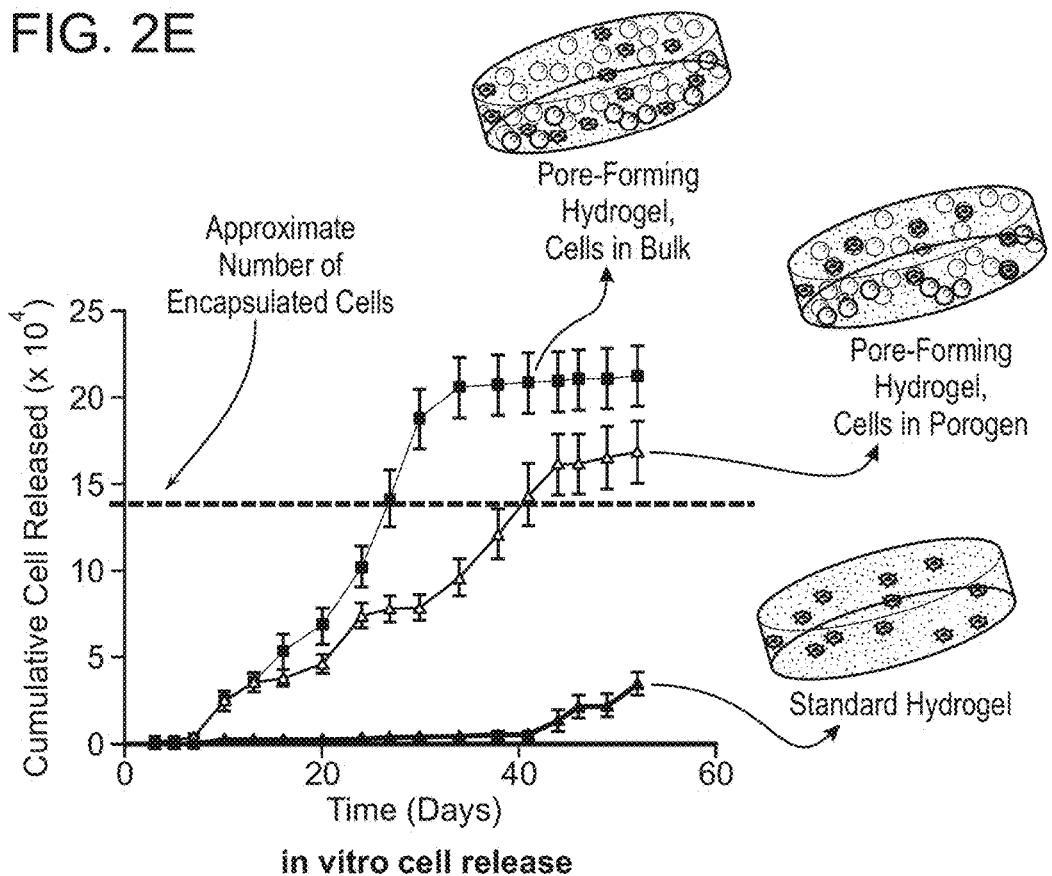
FIG. 2E is a line graph and schematic illustrating the kinetics of deployment for MSC encapsulated either into the bulk phase, the porogen phase of pore-forming scaffolds, or into standard hydrogels. Porogens were prepared with 7.5% oxidized alginate and crosslinked in 100 mM $CaCl_2$.
Figure 2F:
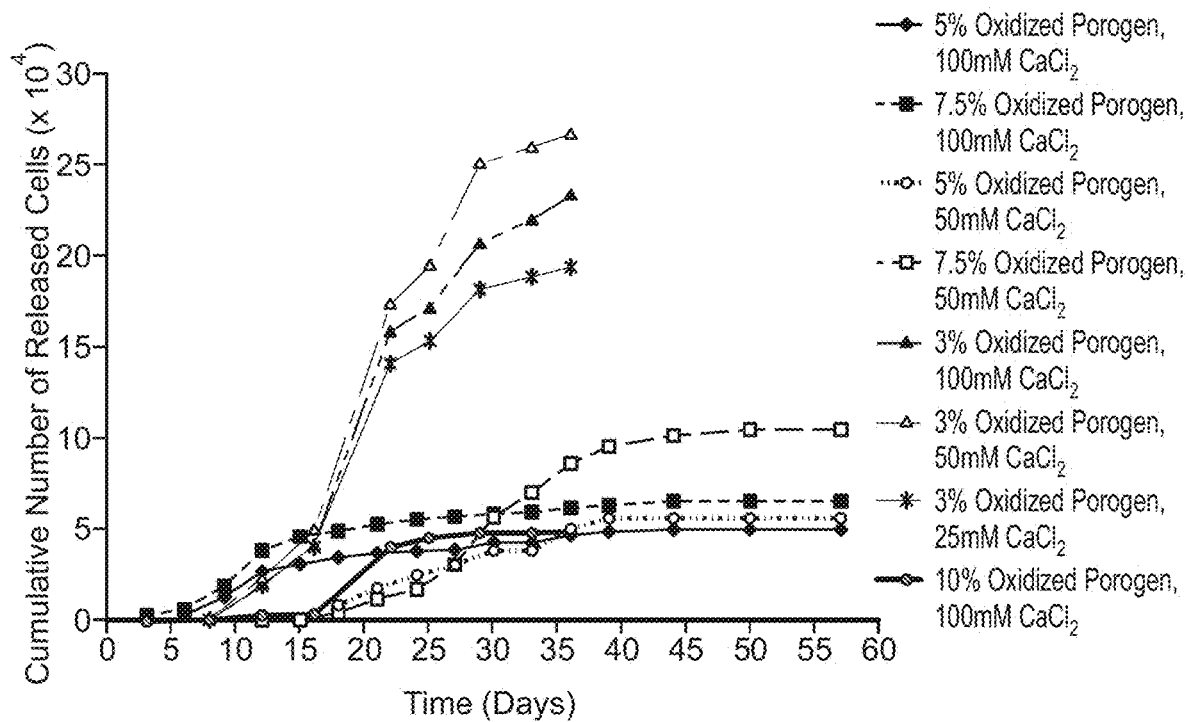
FIG. 2F is a line graph showing the kinetics of MSC deployment from the porogen phase of pore-forming hydrogels as a function of porogen fabrication conditions for D1 cells encapsulated into porogens.

Physical and in vitro studies were performed to determine the kinetics of interconnected void formation, and the corresponding kinetics of mesenchymal stem cell release (FIG. 2A and FIG. 2E, respectively. A clonally derived, commercially available mouse mesenchymal stem cell line (D1) was used for these in vitro studies. A capillary assay was used to assess void formation. Briefly, the density of interconnected voids was measured by first weighing buffer-saturated composite pore-forming gels, and then re-weighing gels after wicking away water by gently touching the surface of the gel with a paper towel. The void fraction was calculated based on the relative change in mass. For in vitro cell release assays, the bulk component of pore-forming hydrogels was modified with 2 RGD peptides/alginate polymer, and had an elastic modulus of 60 kPa. Interconnected voids formed over the first 7 days unless a very high fraction of porogens (above the percolation limit; 80%) were present. No substantial interconnected void formation was observed with a sub-percolation porogen density. The kinetics of MSC deployment from the porogen phase of pore-forming hydrogels as a function of porogen fabrication conditions for D1 cells encapsulated into porogens is illustrated in FIG. 2F.

Figure 2G:
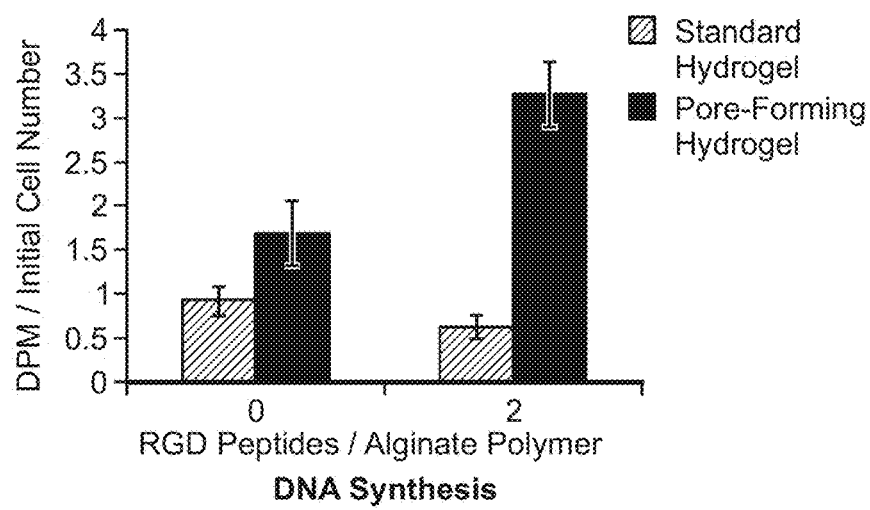
FIG. 2G is a bar graph showing that quantitative analysis of $^3$H-thymidine incorporation indicates enhanced cell proliferation, in an RGD-dependent manner.

Release studies were subsequently performed with a mouse MSC line. Cell release was observed in proportion to overall pore density and gradual change in cell morphology, reflecting a loss of micron-scale confinement. Experiments were performed to determine the effects of pore formation on cellularity and cell proliferation within hydrogels. Cellularity was determined qualitatively using Calcein-AM staining, while proliferation was determined qualitatively by immunostaining for Ki-67 expression or quantitatively by measuring $^3$H-thymidine incorporation. Three-dimensional reconstructions of Calcein-AM stained cells distributed throughout pore-forming hydrogels are presented in FIG. 2B. The substantial changes in cell morphology depict the cells' ability to migrate and proliferate within pore-forming hydrogels, whereas cells remained sparse and rounded within standard hydrogels. Ki-67 immunofluorescence indicated higher cellularity, and increased proliferation, within pore-forming hydrogels compared to standard hydrogels. Quantitative analysis of $^3$H-thymidine incorporation indicated enhanced cell proliferation in an RGD-dependent manner (FIG. 2G).

Figure 2H:
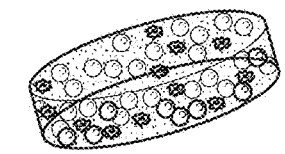
FIG. 2H is a series of line graphs showing the effects of the degree of alginate oxidation degree on cell release. At a constant level of calcium to crosslink porogens (100 mM), increasing the degree of oxidation from 3-7.5% substantially increased the overall number of release cells, whereas lowered the degree of oxidation slightly delayed cell release. At a constant degree of porogen degree of oxidation (7.5%), increasing the concentration of calcium used to crosslink porogens from 25-100 mM lowered the overall number of released cells and slightly delayed the onset of cell release. Scale bars: (A): 100 μm.
Figure 2H:
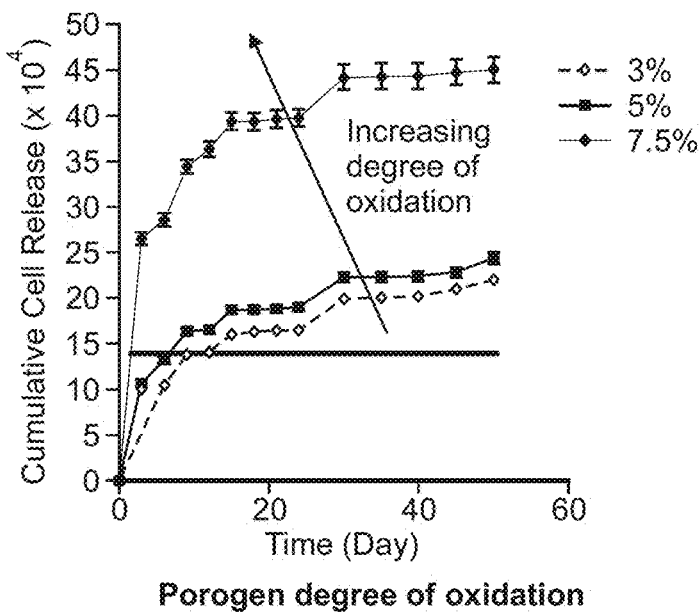
Figure 2H:
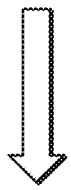
Figure 2H:
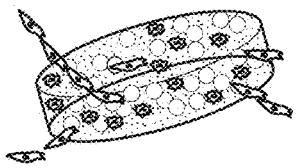
Figure 2H:
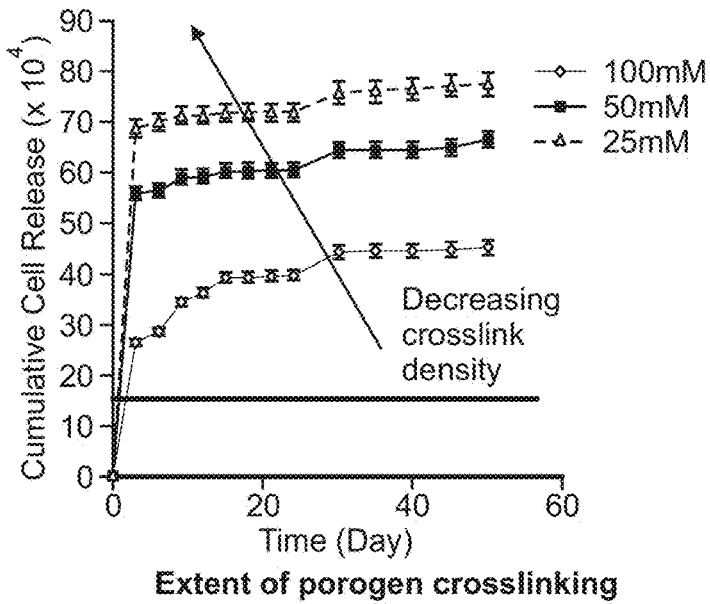

Studies were performed to determine whether varying the chemical composition or cross-linking conditions used to form porogens would modulate the kinetics of cell release (Bouhadir K H, Lee K Y, Alsberg E, Damm K L, Anderson K W, Mooney D J. Degradation of Partially Oxidized Alginate and Its Potential Application for Tissue Engineering. *Biotechnol. Prog.* 2001; 17: 945-50). FIG. 2H shows that cell release kinetics were controlled by the compartmentalization of cells either into porogens or the bulk gel surrounding them, and that porogens that were crosslinked with a lower concentration of calcium degraded more slowly, releasing cells at a later time point. The lower concentration of calcium used to fabricate porogens led to more homogeneous cross-linking.

Pore-forming hydrogels were formed with a constant bulk component (2 RGD/polymer, 60 kPa), and constant porogen density (50%), but varying porogen composition. The chemical composition of porogens was manipulated by varying the theoretical degree of oxidation of the alginate polymers. Oxidation degree was controlled by varying the ratio of sodium periodate to alginate during the oxidation reaction (Bouhadir 2001). Binary mixtures of 20 mg/mL oxidized alginate with 5 mg/mL unmodified, high $M_w$ alginate, were used to form porogens. Porogens were formed by crosslinking in a bath of 25-100 mM $CaCl_2$. The effects of the degree of alginate oxidation degree on cell release are shown in FIG. 2H. At a constant level of calcium to crosslink porogens (100 mM), increasing the degree of oxidation from 3-7.5% substantially increased the overall number of release cells, whereas lowering the degree of oxidation slightly delayed cell release. At a constant degree of porogen degree of oxidation (7.5%), increasing the concentration of calcium used to crosslink porogens from 25-100 mM lowered the overall number of released cells and slightly delayed the onset of cell release.

Example 3

Controlling Mesenchymal Stem Cell Deployment, Engraftment, and Proliferation in Vivo Finally, in vivo studies were performed to determine if pore-forming hydrogels could be used to manipulate the release kinetics of MSC in vivo. For this, mouse MSC expressing mCherry were transplanted subcutaneously into Nude mice. Cell engraftment, proliferation and deployment were observed with non-invasive fluorescence imaging. This showed that not only did pore-forming gels delay engraftment compared to cells delivered in saline, but that these materials ultimately led to more proliferation. The hydrogels provide a micro-environment ammenable to proliferation after pores have formed. Finally, as these materials were useful to promote MSC release and expansion in vivo, human MSC were administered to regenerate cranial defects on nude rats. This led to improved regeneration of mineralized bone, even at an early time-point.

Specifically, for in vivo studies, D1 cells were modified to constitutively express a detectable marker, e.g., mCherry or green fluorescent protein (GFP), and were encapsulated either into standard bulk gels with no porogens, pore-forming hydrogels, or mixed with saline. Next, cells were injected into the backs of Nude mice through 18-gauge needles. Cell release and proliferation over time were monitored via mCherry fluorescence observed on an IVIS system (Caliper Life Sciences). These data revealed significantly more cell release and proliferation from pore-forming hydrogels than from standard gels (FIG. 3). Moreover, although cells did proliferate if delivered by simple saline injection, deployment from pore-forming hydrogels 1) altered the kinetics of local cell delivery and proliferation, and 2) eventually led to a substantially higher number of delivered cells (FIG. 3).

Figure 3A:
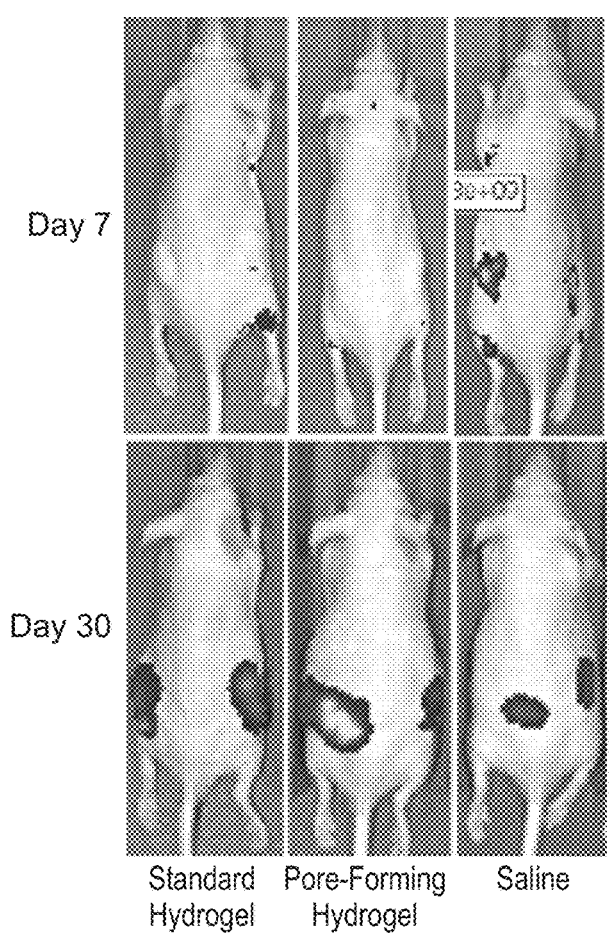
FIG. 3A is a photograph showing representative images of Nude mice into which 2×10$^6$ mCherry-expressing MSC were deployed, either 7 or 30 days after injection in standard hydrogels (left), pore-forming hydrogels in which porogens were crosslinked with either 100 mM $CaCl_2$ (center), or saline (right). The bulk component of hydrogels was modified with 2 RGD/polymer chain. Initially, more cells engrafted in the saline only condition, but at later time-points, there were fewer cells in this condition and substantially more cells eventually engrafting when released from pore-forming hydrogels.
Figure 3B:
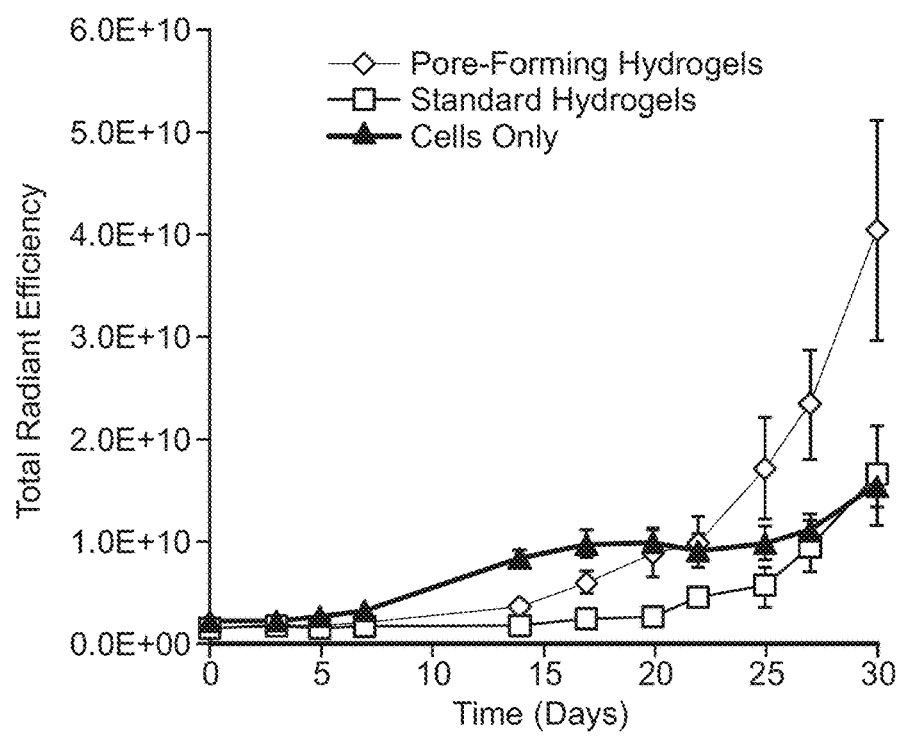
FIG. 3B is a line graph showing the quantification of the relative radiant efficiency (proportional to cell density) of mCherry-MSC injected in pore-forming hydrogels, standard hydrogels, or saline.
Figure 3C:
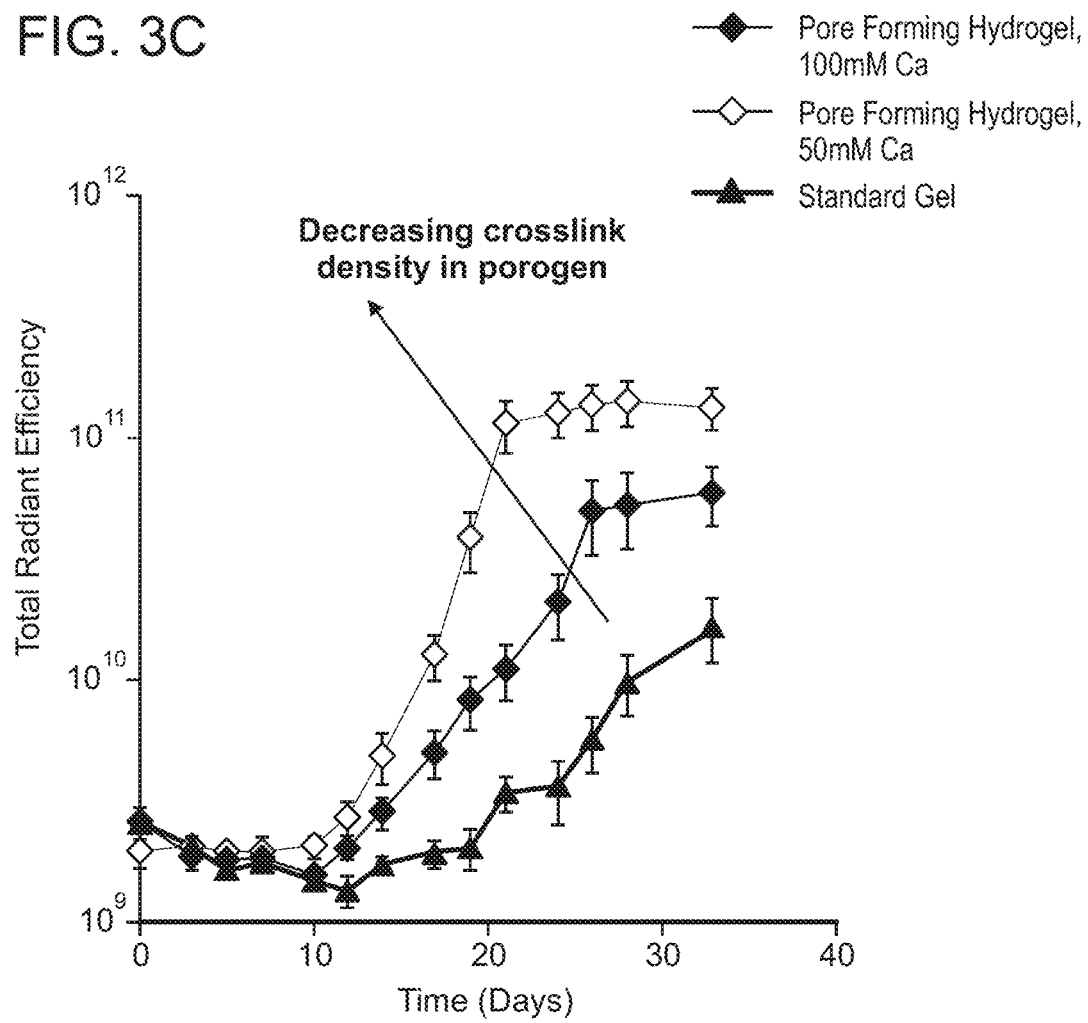
FIG. 3C is a line graph showing that decreasing the density of calcium used to crosslink porogens substantially decreased the overall density of released cells, and slightly delayed the kinetics of deployment (error bars are SEM, n=4-6).
Figure 3D:
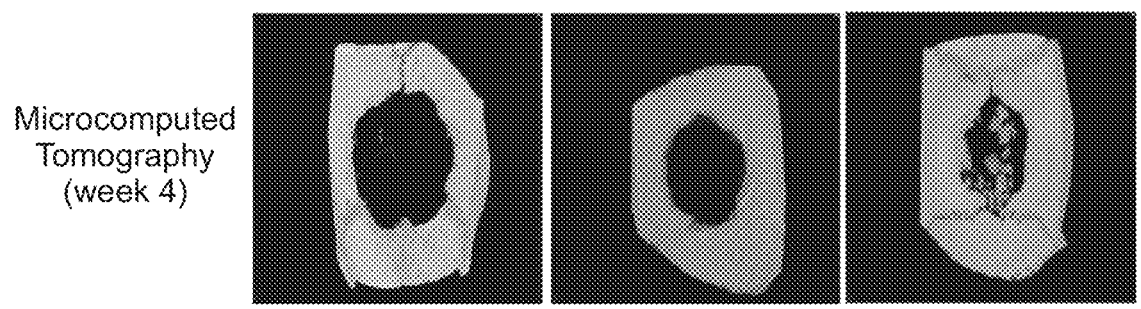
FIG. 3D is a series of photographs showing the ability of pore-forming hydrogels to enhance human mesenchymal stem cell mediated bone regeneration using a Nude Rat cranial defect model. Critically-sized defects were formed in the crania of Nude Rats (Charles River). Immediately after defect formation, commercially available human mesenchymal stem cells (Lonza) were transplanted into the defect space, either within saline ("Cells Only"), a standard hydrogel (2 RGD/alginate polymer, 60 kPa), or a Pore-Forming Hydrogel. Representative cross-sections of micro-computed tomographic analysis of new bone formation within cranial defects 4 weeks after implantation. Substantially more new bone forms within defects in which cells were delivered via pore-forming hydrogels.

Specifically, experiments were performed to determine the ability to manipulate the kinetics of cell release in vivo by varying the composition of porogens. As shown in FIG. 3, stem cells were released from pore-forming hydrogels in vivo within the subcutaneous space of nude mice. $2 \times 10^6$ mCherry-expressing MSC were deployed into Nude mice, either 7 or 30 days after injection in standard hydrogels (left), pore-forming hydrogels in which porogens were crosslinked with either 100 mM or 50 MM $CaCl_2$ (center), or saline (right). The bulk component of hydrogels was modified with 2 RGD/polymer chain. Initially, more cells engrafted in the saline only condition, but at later time-points, there were fewer cells in this condition and substantially more cells eventually engrafting when released from pore-forming hydrogels. The quantification of the relative radiant efficiency (proportional to cell density) of mCherry-MSC injected in pore-forming hydrogels, standard hydrogels, or saline is shown in FIG. 3B. Decreasing the density of calcium used to crosslink porogens substantially decreased the overall density of released cells, and slightly delayed the kinetics of deployment (FIG. 3C; error bars are SEM, n=4-6). The ability of pore-forming hydrogels to enhance human mesenchymal stem cell mediated bone regeneration was demonstrated in a Nude Rat cranial defect model (FIG. 3D). Critically-sized defects were formed in the crania of Nude Rats (Charles River). Immediately after defect formation, commercially available human mesenchymal stem cells (Lonza) were transplanted into the defect space, either within saline ("Cells Only"), a standard hydrogel (2 RGD/alginate polymer, 60 kPa), or a Pore-Forming Hydrogel. The top row of FIG. 3D shows representative cross-sections of micro-computed tomographic analysis of new bone formation within cranial defects 4 weeks after implantation. Substantially more new bone forms within defects in which cells were delivered via pore-forming hydrogels. Doxycycline incorporation (green) into newly-forming bone at 12 weeks after implantation demonstrates that pore-forming hydrogels lead to positive doxycycline staining within the tissue rather than false-positive staining of the subcutaneous tissues.

Example 4

In Vitro Release of Two Different Cell Populations at Distinct Times

Figure 4:
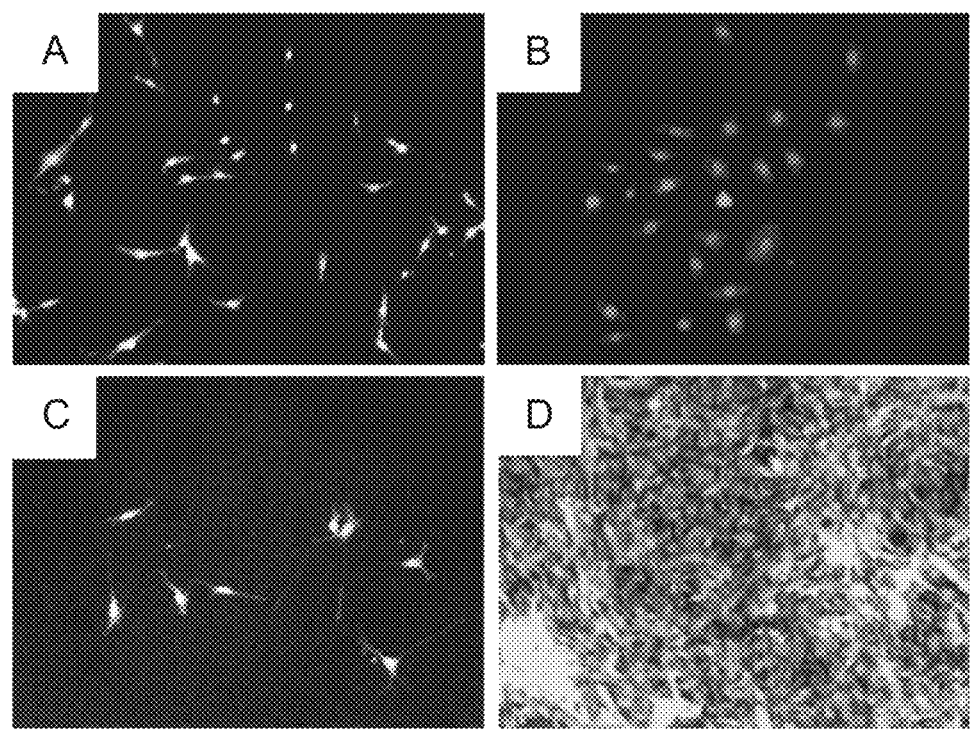
FIG. 4 is a series of photomicrographs depicting the use of pore-forming hydrogels to release distinct populations at different times.

Pore-forming hydrogels were formed as described in Examples 1 and 2. Equal numbers (approximately 106 cells/mL of composite pore-forming hydrogel) GFP-expressing myoblasts and outgrowth endothelial cells (OECs, vascular progenitor cells) were encapsulated into different compartments of the material. After 5 days of culture in vitro, cells that were released and adherent to tissue culture plastic were stained with Ethidium Homodimer (EtD-1; red). As shown in FIG. 4, the cell type encapsulated into the bulk gel deployed more rapidly. This pattern of deployment occurred even for OECs, which migrate more slowly and proliferate less extensively than GFP-myoblasts (based on analysis of substrates onto which equal numbers of both cell types were added; FIG. 4d).

Specifically, the use of pore-forming hydrogels to release distinct populations at different times is shown in FIG. 4. Fluorescent micrographs of GFP-expressing myoblasts and outgrowth endothelial cells (OECs) adherent to tissue culture plastic after 4 days of culture within pore-forming hydrogels in which the chemistry used to form porogens was varied and the different cell types were initially placed into distinct compartments are shown in FIGS. 4A-4C. FIG. 4A depicts myoblasts in bulk component, OECs in porogen component, while FIG. 4B depicts myoblasts in bead component, OECs in porogen component. FIG. 4C depicts both myoblasts and OECs in bulk component. Equal numbers of GFP-myoblasts and OECs were seeded onto a plastic substrate (FIG. 4D). Myoblasts outgrew OECs. Cells were stained with Ethidium Homodimer (red), so that GFP-myoblasts appear yellow and OECs appear red.

Example 5

Recruitment of Host Lymphocytes from Subcutaneous Tissues by Pore-Forming Hydrogels with Different Porogen Formulations Pore-forming hydrogels were formed as described in Examples 1 and 2. To form the porogen phase, 7.5 mg/mL of high Mw, GA-rich alginate polymer was combined with 20 mg/mL of either alginate dialdehyde (7.5% theoretical degree of oxidation) or alginate dialdehyde in which aldehyde groups were reduced to alcohol groups. Pore-forming hydrogels without encapsulated cells were next injected into the backs of C57/BL6 or Balb/c mice. After 14 days, recruitment of host dendritic cells was observed by histology.

As described in detail below, pore-forming hydrogels were utilized for chemokine-mediated cell recruitment. Alginate was first oxidized and then reduced with sodium borohydride to make alcohol groups that replace what were originally sugars. FIG. 5A and FIG. 5B show a comparison of dendritic cell (DC) recruitment by a standard, degradable alginate hydrogel versus a pore-forming alginate hydrogel. Both sets of hydrogels were loaded with 2 ug of granulocyte-macrophage colony stimulating factor. This indicates substantially more infiltration of cells from the tissue adjacent the hydrogel (highly cellular area near the edge of the image) into the pore-forming hydrogel. FIGS. 5C and 5D show a comparison of baseline DC invasion into pore-forming hydrogels in which porogens were formed from alginate dialdehyde (FIG. 5C) or from reduced alginate dialdehyde (FIG. 5D) without GM-CSF. Substantially less baseline cell infiltration occurred absent GM-CSF. For histology, dendritic cells are stained for CD11c (green) and NIHC-II (red), with Hoescht nuclear counterstain (blue). This figure shows the difference in host cell recruitment by materials with porogens formed from the oxidized alginate vs. reduced alginate.

Example 6

Control of Stem Cell Proliferation within Pore-Forming Hydrogels by Varying Bulk Phase Composition The purpose of this approach is to manipulate cell expansion and release using insoluble cues. Thus, it was determined whether the density of adhesion ligands and mechanical properties of the non-degrading hydrogel surrounding porogens would have effects on the cells. As shown in FIG. 6, the density of ligands significantly altered DNA synthesis, whereas altering elastic modulus altered both DNA synthesis and cell release over 1 week. Insoluble cues like adhesion ligand density had effects on cells over long time-frames, as shown by histology in FIG. 6D.

Figure 6A:
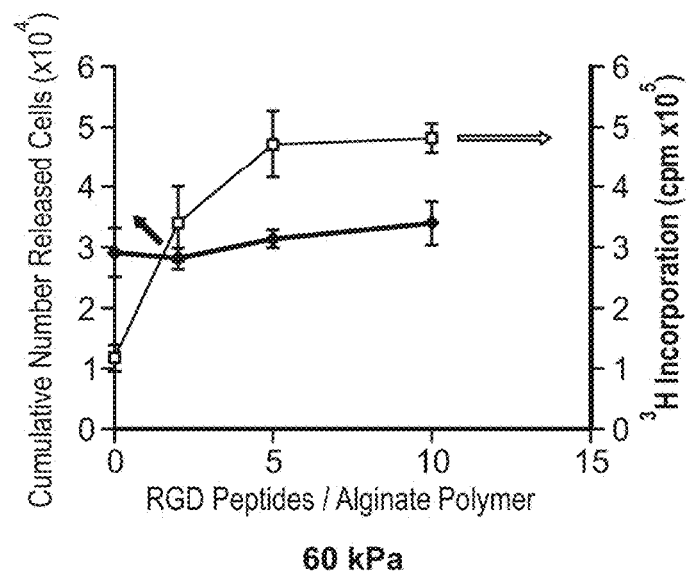
FIG. 6A and FIG. 6B are line graphs showing the analysis of 24 hr 3H-thymidine incorporation (proportional to DNA synthesis) by mesenchymal stem cells (D1; red curve) or cumulative MSC deployment (blue curves) from pore-forming hydrogels after 7 days of culture as a function of (FIG. 6A) density of RGD peptides in bulk gels with 60 kPa modulus, or (FIG. 6B) elastic modulus of bulk hydrogels presenting 10 RGD peptides/alginate polymer (data are mean+/−SEM, n=3-5). RGD density had significant effects of cell proliferation, whereas elastic modulus had effects on both proliferation and release (p<0.05, ANOVA).
Figure 6B:
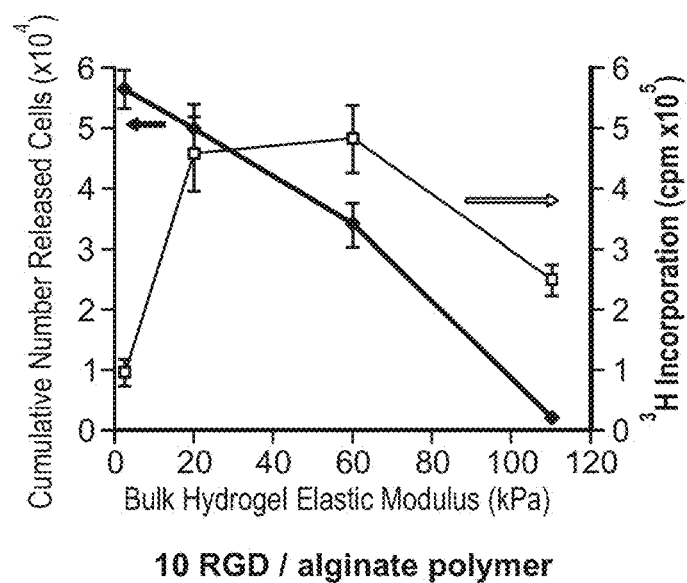
Figure 6C:
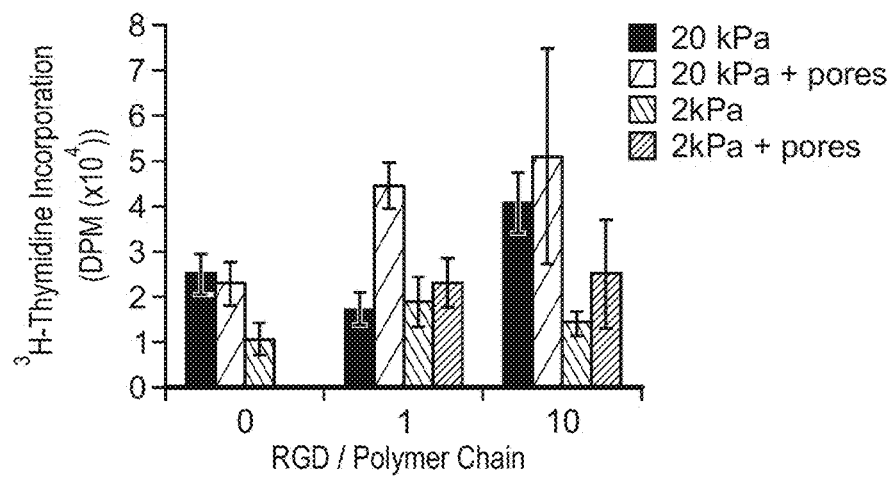
FIG. 6C is a bar graph showing the analysis of DNA synthesis as a function of pore formation.
Figure 6D:
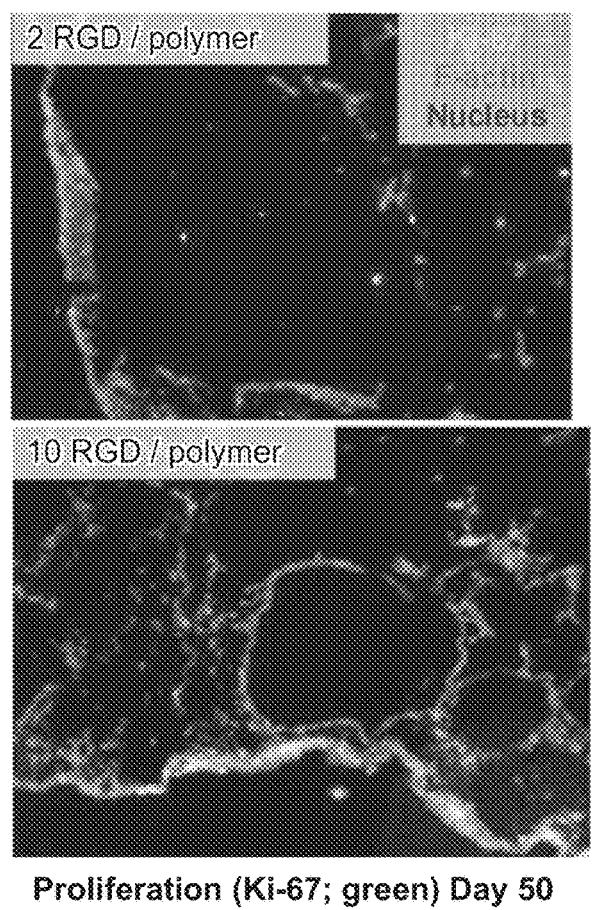
FIG. 6D is a series of photographs showing staining for Ki-67 (proliferation marker, green) in D1 cells in cryo sectioned pore-forming hydrogels after 50 days of culture.

Specifically, studies were performed to determine whether the composition of the bulk component of pore-forming hydrogels could modulate cell proliferation and engraftment in vivo. The analysis of 24 hr $^3$H-thymidine incorporation (proportional to DNA synthesis) by mesenchymal stem cells (D1; red curve) or cumulative MSC deployment (blue curves) from pore-forming hydrogels after 7 days of culture as a function of density of RGD peptides in bulk gels with 60 kPa modulus, or elastic modulus of bulk hydrogels presenting 10 RGD peptides/alginate polymer (data are mean+/−SEM, n=3-5) is shown in FIGS. 6A and 6B. RGD density had significant effects of cell proliferation, whereas elastic modulus had effects on both proliferation and release ($p<0.05$, ANOVA). The analysis of DNA synthesis as a function of pore formation is shown in FIG. 6C. Staining for Ki-67 (proliferation marker, green) in D1 cells in cryosectioned pore-forming hydrogels after 50 days of culture is shown in FIG. 6D.

Control of Deployed Stem Cell Fate Via Composition of the Bulk Hydrogel

Figure 6E:
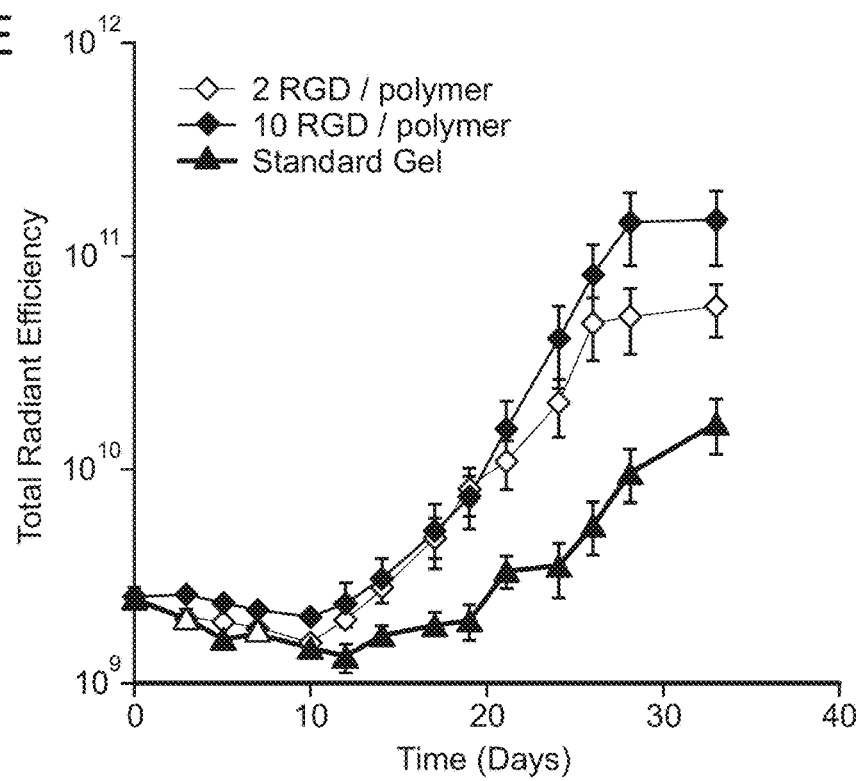
FIGS. 6E and 6F is a line graph showing the control of mesenchymal stem cell deployment, engraftment and proliferation in vivo.
Figure 6F:
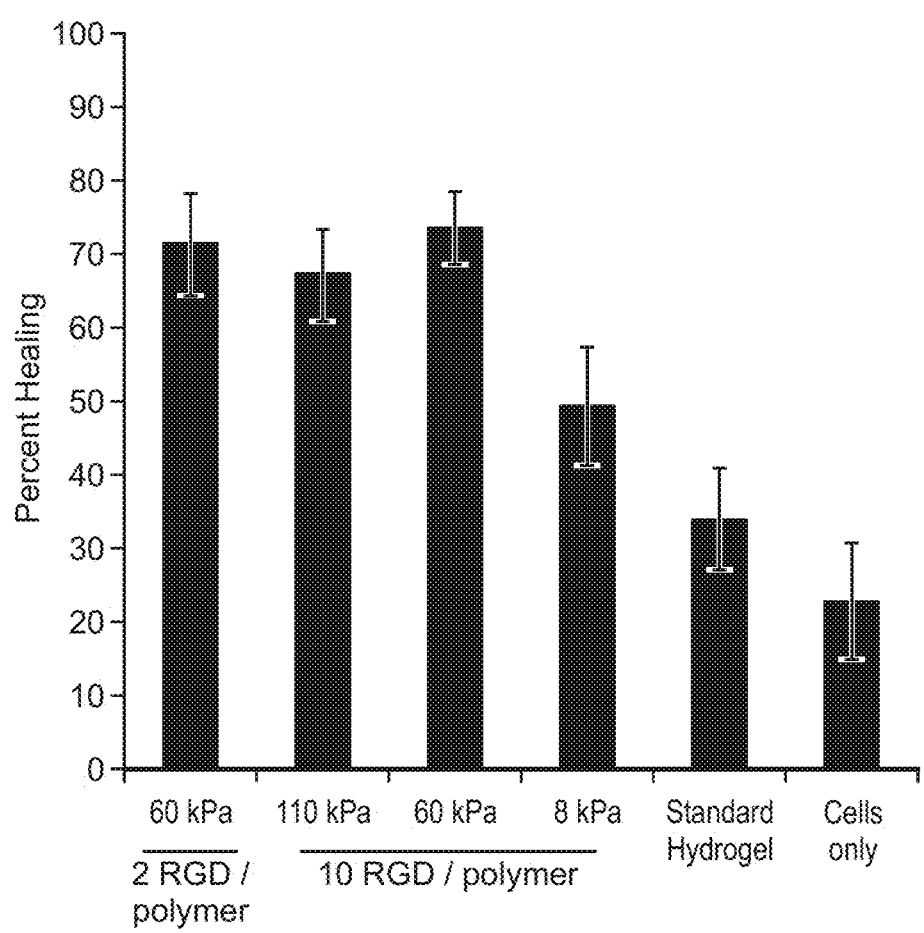

Pore forming hydrogels were formed as described in Example 1. By manipulating the composition (density of integrin-binding RGD peptides and elastic modulus) of the bulk hydrogel, it was possible to control mesenchymal stem cell (MSC) proliferation and release in vitro. In vivo, the overall density of mCherry-labeled mouse MSC deployed into the subcutaneous space could be increased by increasing the density of RGD peptides from 2 to 10 peptides per alginate polymer chain (FIG. 6E). For therapeutic studies, human MSC were deployed into Nude Rat cranial defects. After 4 weeks, rats were euthanized, and the degree of healing (due to new bone formation) was assessed by Hematoxylin/Eosin staining. Briefly, the area of newly formed bone within the defect was divided by the total area of the defect to generate the "Percent Healing" metric. Using this quantitative metric, it was found that delivering MSC in pore-forming hydrogels was substantially better than delivery via standard hydrogels or saline in terms of ability to induce new bone formation (FIG. 6F). Moreover, the elastic modulus of the bulk hydrogel component had a substantial effect on new bone formation at 4 weeks, as deployment from a pore-forming hydrogel with a 60 kPa, 10 RGD/alginate polymer bulk phase led to significantly more bone formation ($p<0.05$, 2-tailed t-test) than deployment from a pore-forming hydrogel with an 8 kPa, 10 RGD/alginate polymer bulk phase.

Thus, when mCherry-labeled D1 were deployed into the subcutaneous tissues of Nude mice via pore-forming hydrogels, increasing the RGD density of the bulk component from 2 to 10 RGD peptides/alginate polymer substantially increased the overall number of engrafted cells without significantly affecting cell deployment kinetics.

Though the example here demonstrated an effect of bulk hydrogel elasticity on cell-mediated tissue regeneration, as described herein, many other aspects of the bulk hydrogel phase—for example, the presentation of matrix-bound growth factors or peptide-mimics thereof—are engineered to influence cell-mediated tissue regeneration.

Example 7

Figure 7A:
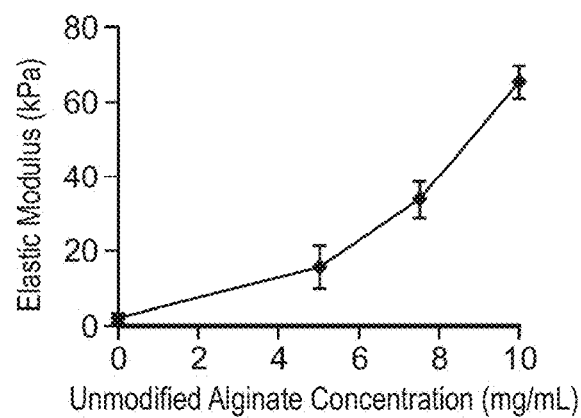
FIG. 7A and FIG. 7B show elastic moduli (FIG. 7A) and degradation (FIG. 7B) of bulk hydrogels formed by crosslinking binary combinations of oxidized alginate (5% theoretical degree of oxidation) at a constant density of 20 mg/mL with unmodified, high $M_w$ alginate. Degradation was assessed by comparing the dry mass after 4 days in-vitro to initial dry mass.
Figure 7B:
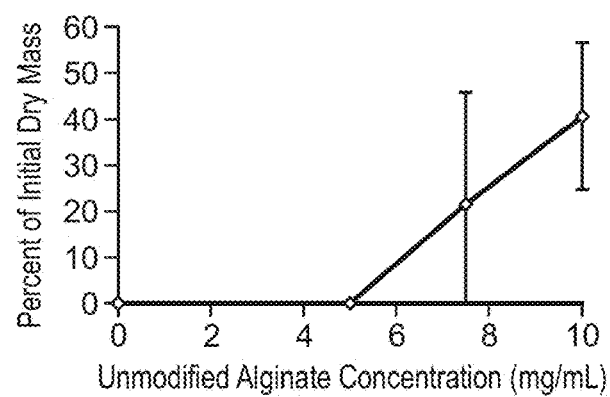
Figure 7C:
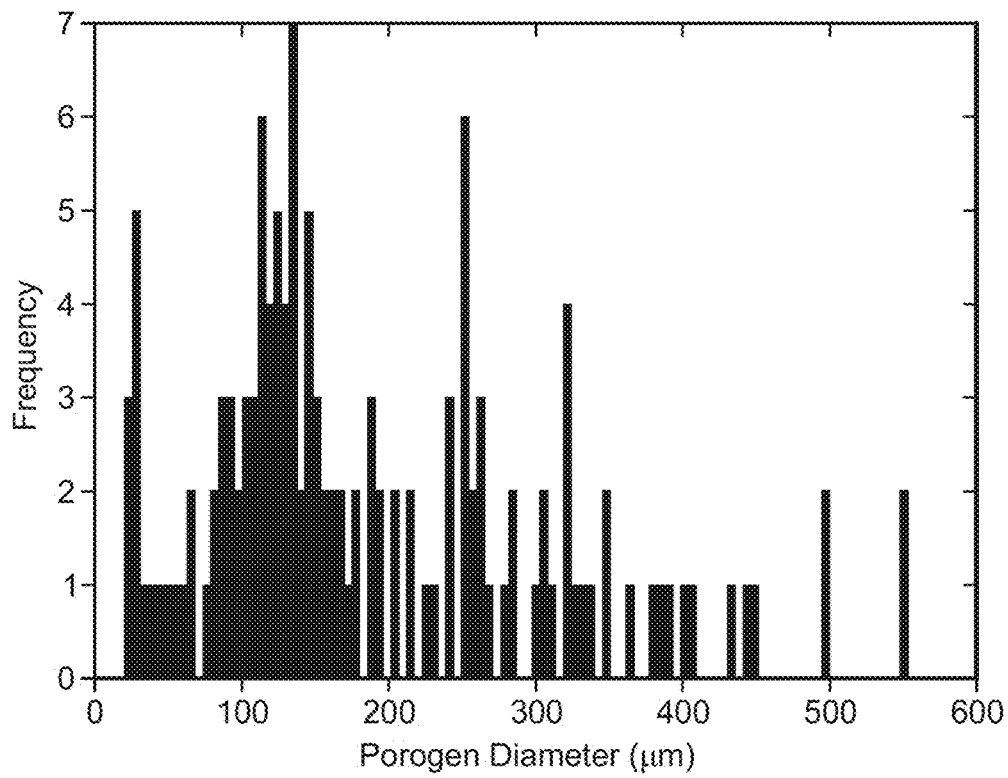
FIG. 7C is a histogram of diameters of porogens formed from binary mixtures of 20 mg/mL oxidized alginate with 7.5 mg/mL unmodified alginate. Porogen diameter was measured by processing fluorescent micrographs of porogens prepared from aminofluorescenin-labeled alginates. Error bars are SD, n=3-4.
Figure 8:
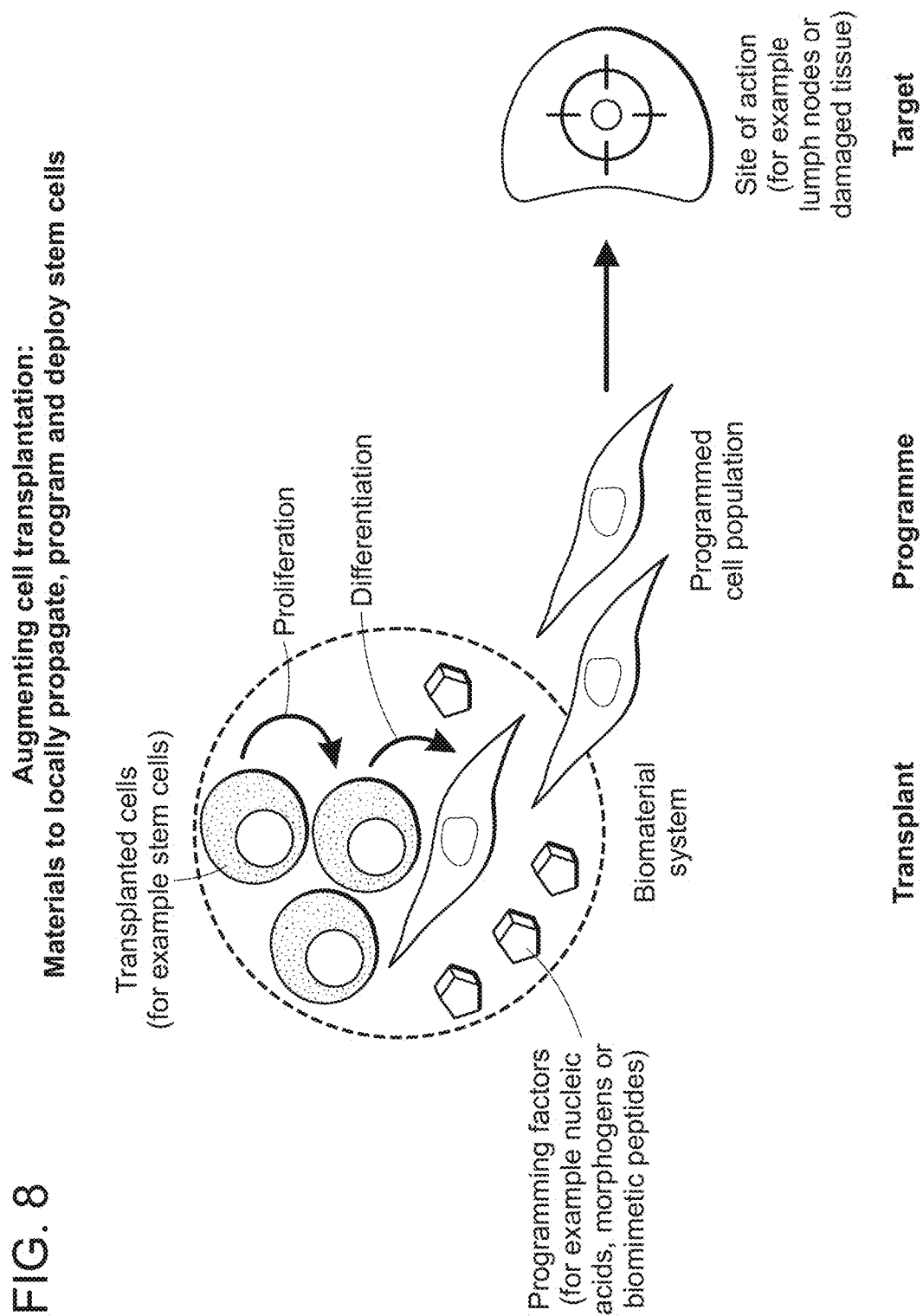
FIG. 8 is a schematic of an implantable biomaterial that mimics certain aspects of stem-cell niches in that it activates transplanted progenitor cells to proliferate and programs them to differentiate into cells that migrate into damaged tissues to participate in regeneration.
Figure 9:
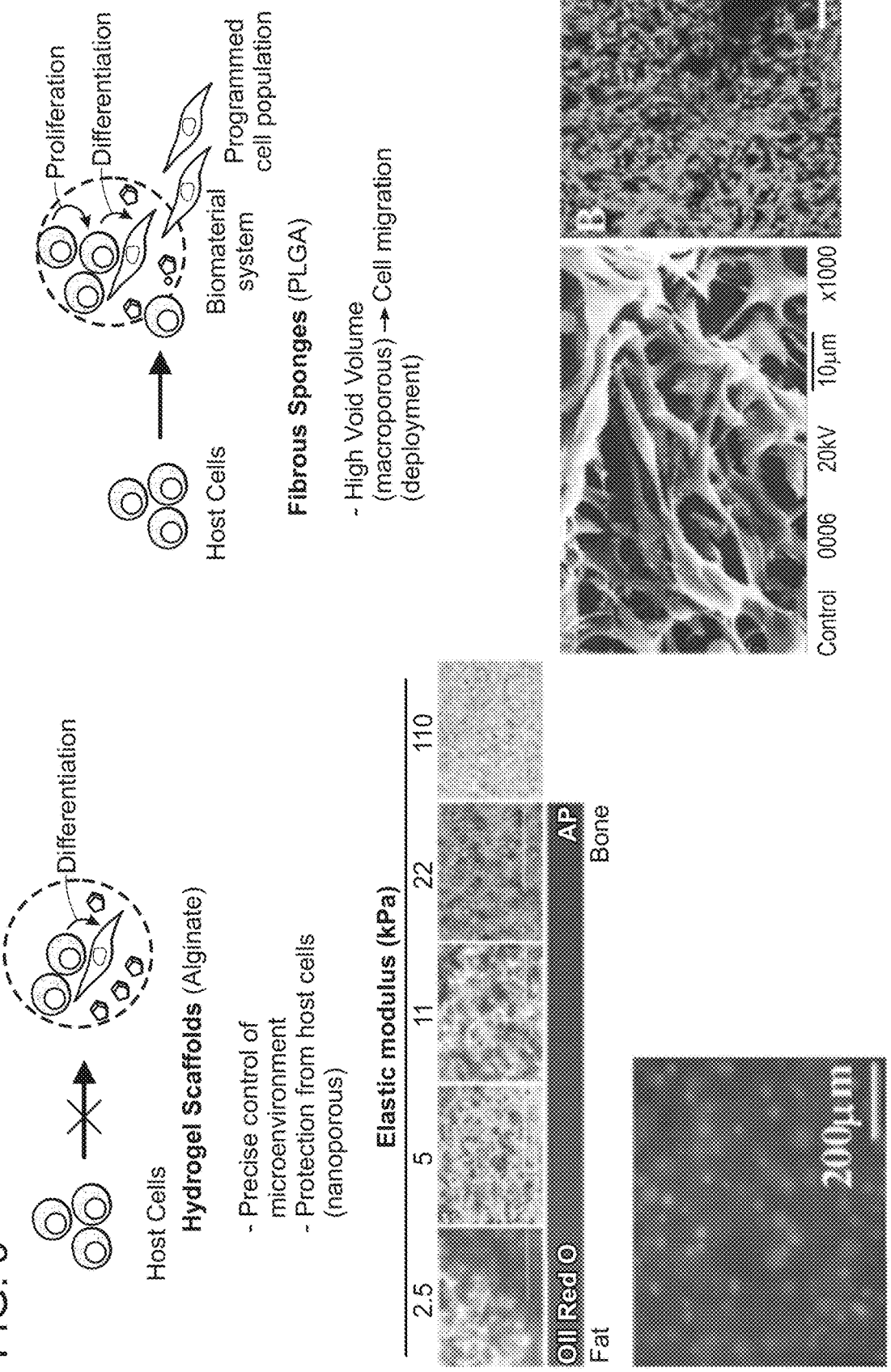
FIG. 9 is a schematic of a hydrogel scaffold (left, top), which controls transplanted cell fate through presentation of specific cues, but prevents transplanted cells from migrating out of, and host cells from migrating into, the material. Bottom: example data depicting the ability of a nanoporous hydrogel to control mesenchymal stem cell fate, in this case via elastic modulus. Right, top: schematic of a macroporous sponge which controls transplanted fate through presentation of specific cues, while also allowing host cells to migrate into, and transplanted cells to migrate out of the material.
Figure 10:
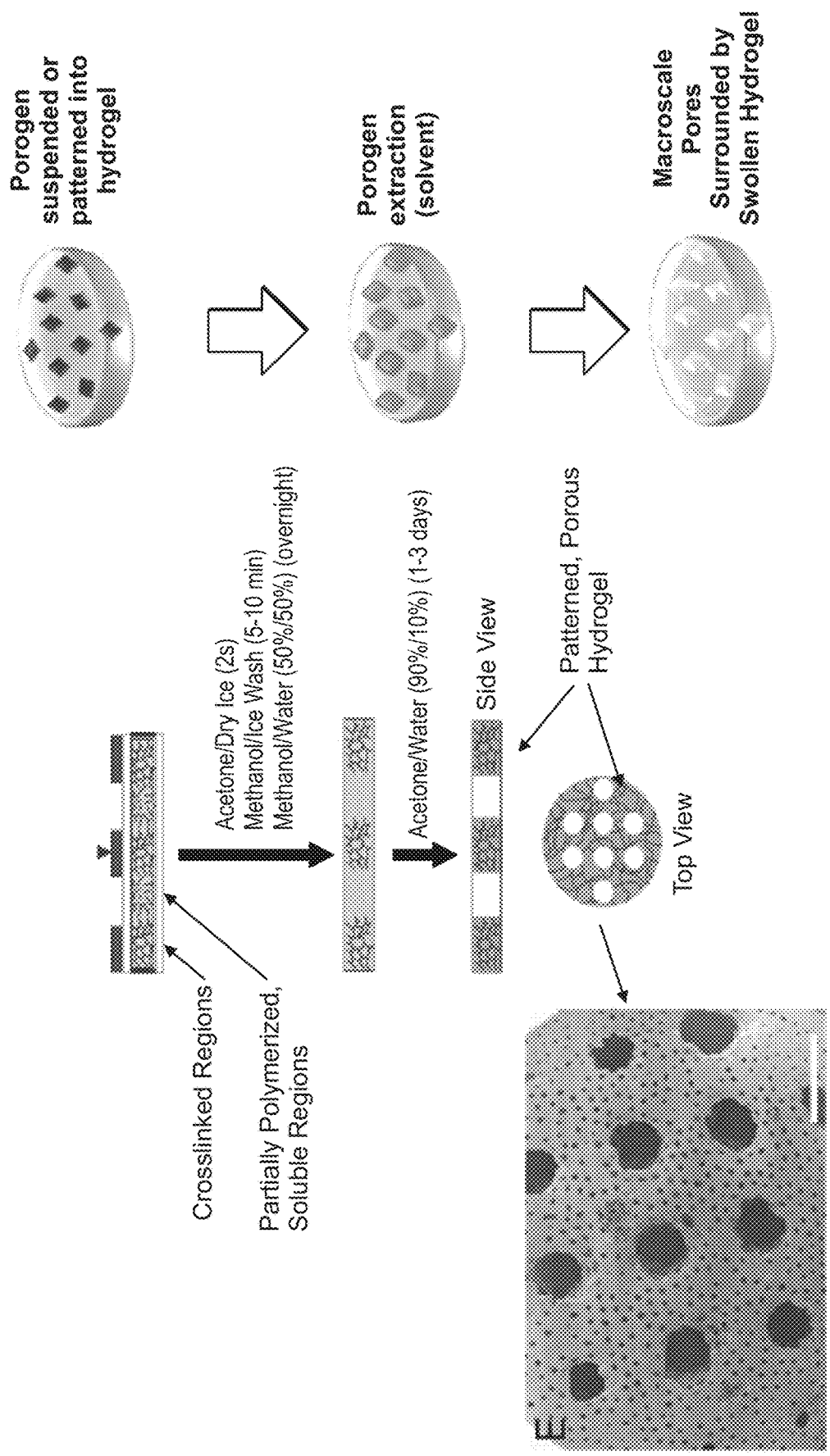
FIG. 10 is a series of images depicting an alternative strategy to produce macroporous hydrogels. As described in the schematics (center, right), porogens are embedded into a "bulk" hydrogel, or photolithographic techniques are applied, to provide non-crosslinked regions of the bulk hydrogel. After crosslinking the bulk hydrogel, the non-crosslinked portions of the hydrogel and porogens are removed using solvents such as acetone. Left: image of a macroporous hydrogel.
Figure 11:
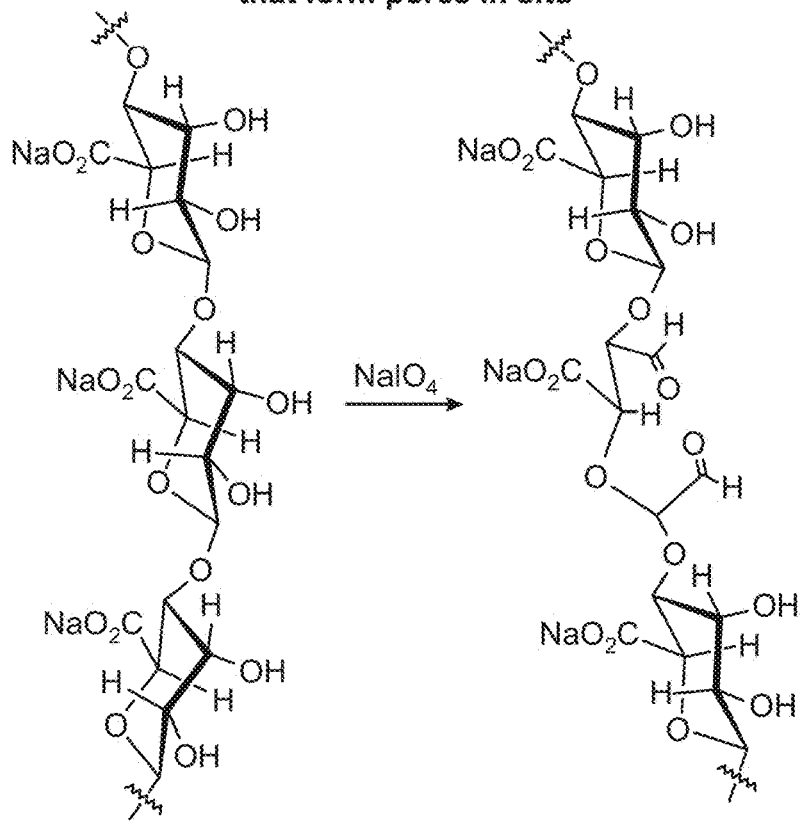
FIG. 11 is a schematic and a bar chart depicting a strategy to create rapidly degrading alginate-based hydrogel porogens. Top left: chemical reaction scheme to oxidize alginate to alginate dialdehyde with $NaIO_4$. Top right: schematic depicting the loss of crosslinkable, guluronic-acid rich portions of alginate (short, straight segments), and the overall decrease in polymer $M_w$ due to sodium periodate oxidation. Bottom: data depicting loss in dry mass over time from hydrogels made from 20 mg/mL non-modified alginate (squares), 20 mg/mL alginate dialdehyde (5% degree of oxidation; diamonds) or a binary mixture of 20 mg/mL alginate dialdehyde with 7.5 mg/mL unmodified alginate (triangles).
Figure 11:
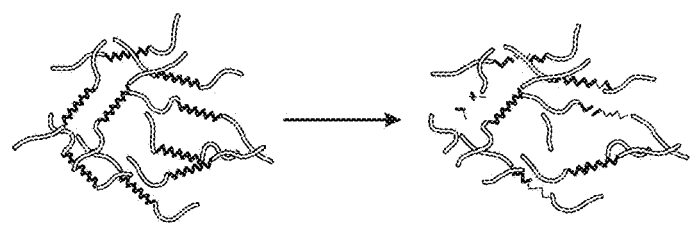
Figure 11:
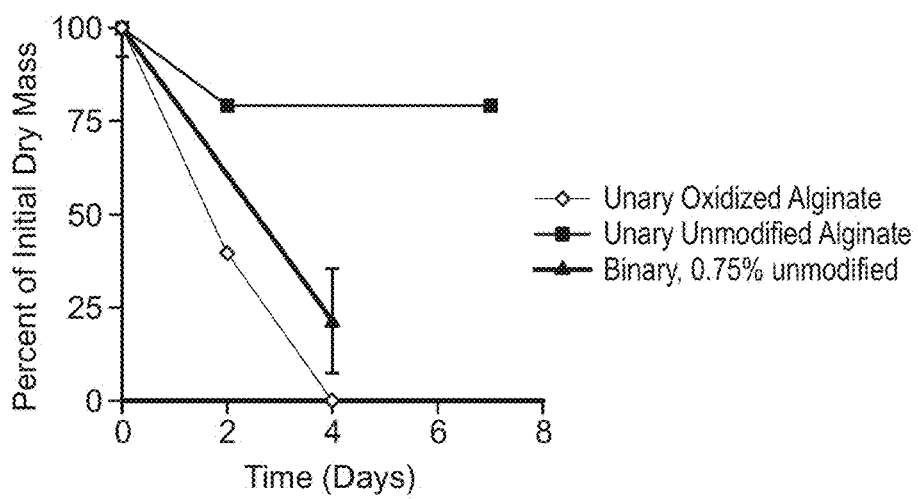
Figure 12:
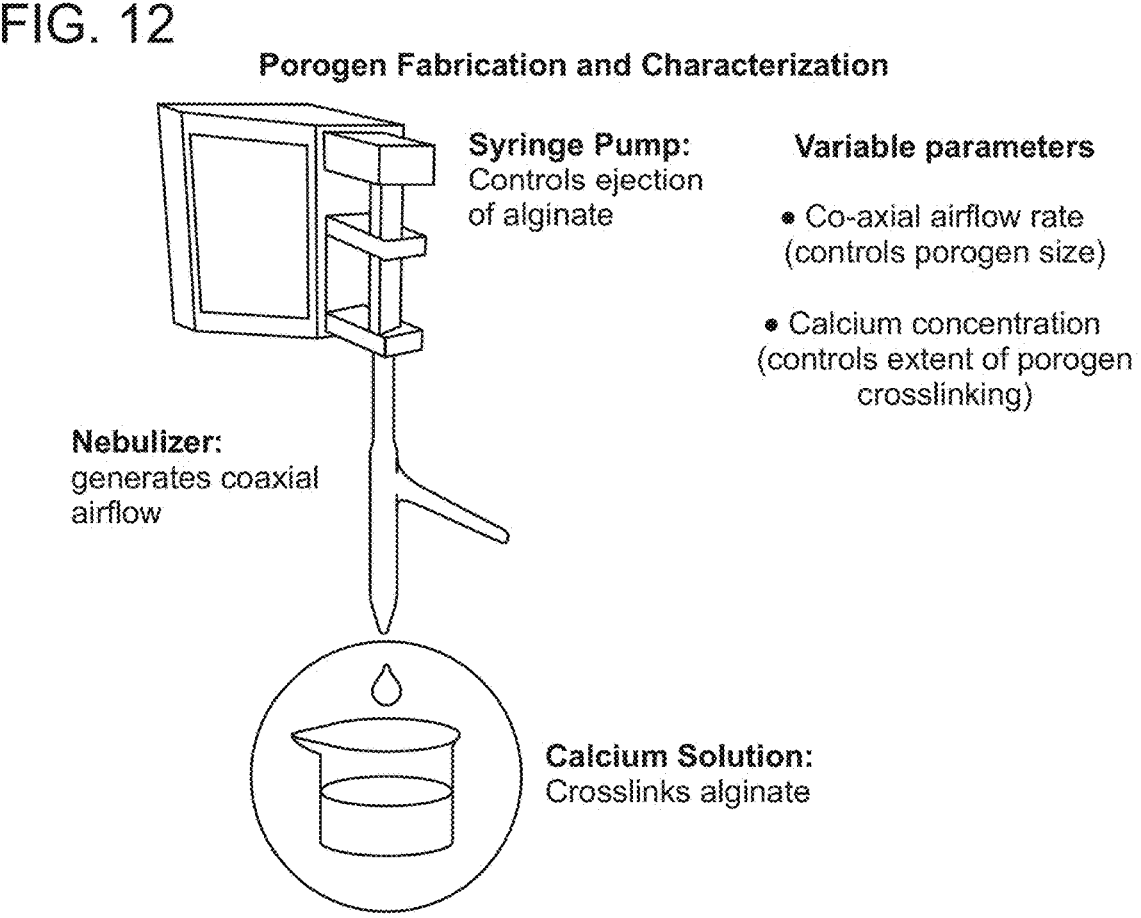
FIG. 12 is a schematic illustrating porogen fabrication and characterization.
Figure 13:
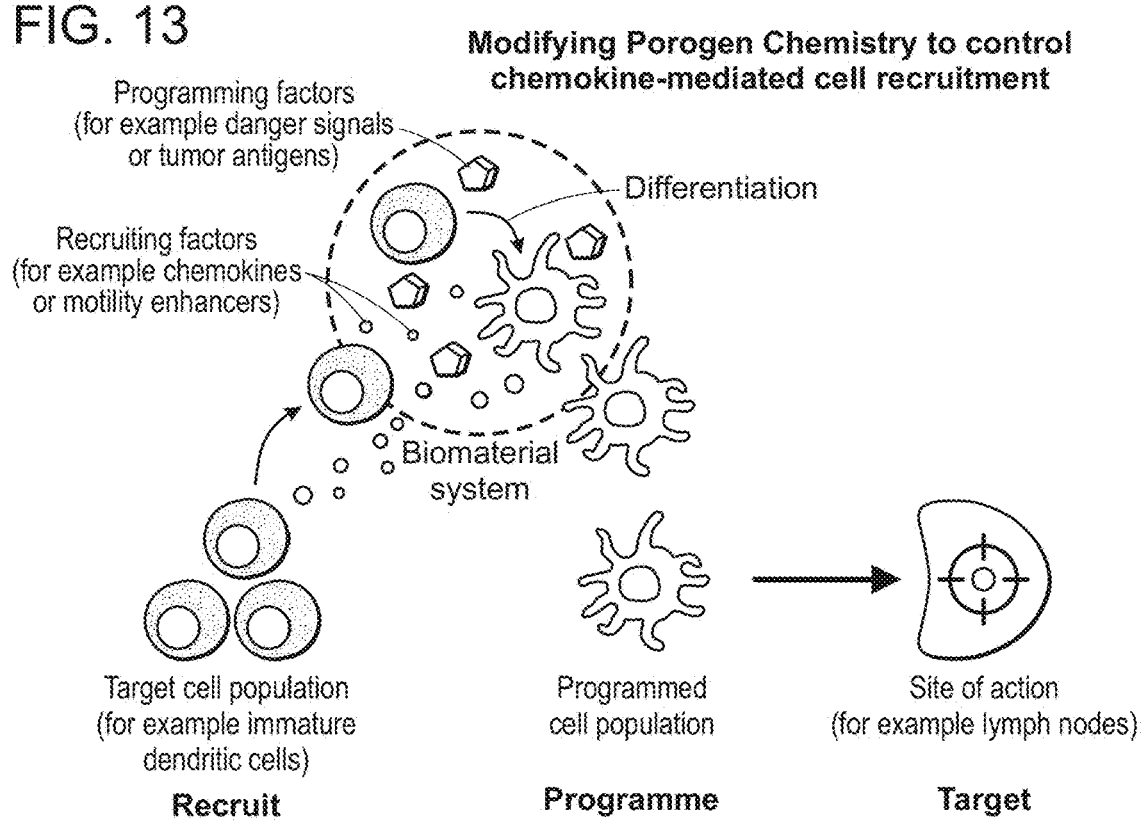
FIG. 13 is a schematic showing the control of host cell recruitment with pore forming hydrogels. Specifically, shown in this Figure is a schematic of an implantable biomaterial system that mimics the icroenvironment of an infection, allowing the recruitment, programming and subsequent targeting of activated antigen-presenting dendritic cells to the lymph nodes to participate in a potent antitumour response.
Figure 14:
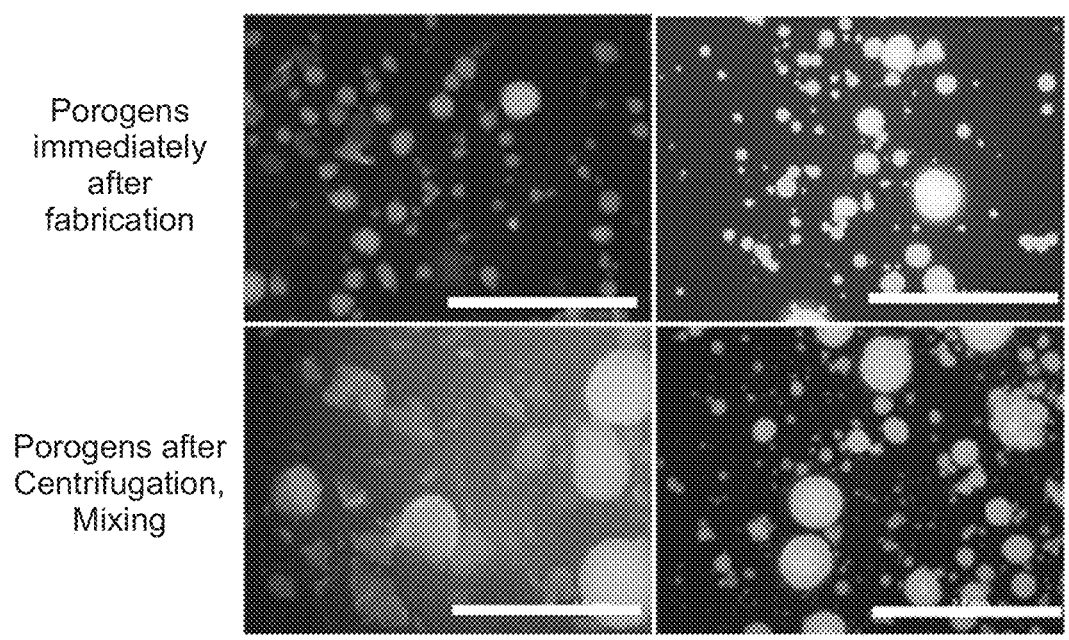
FIG. 14 is a series of photomicrographs showing how the polymers used to comprise the porogen phase affect the degradation and processing of porogens. Specifically, shown in this Figure are fluorescence micrographs of porogens formed using fluorescein-labeled alginate dialdehyde. Immediately after crosslinking in 100 mM $CaCl_2$ (top), porogens are grossly intact, whether made using 20 mg/mL alginate dialdehyde (top left) or a binary mixture of 20 mg/mL alginate dialdehyde with 7.5 mg/mL unmodified alginate. However, after processing steps used to purify porogens and remove excess $CaCl_2$, porogens made with purely alginate dialdehyde were damaged, resulting in substantial change in morphology and release of fluorescein-labeled polymers into solution to yield a substantial level of background fluorescein fluorescence (bottom left). In contrast, binary mixtures of 20 mg/mL alginate dialdehyde with 7.5 mg/mL unmodified alginate resulted in porogens that could withstand processing steps.

Mechanical Properties and In-Vitro Degradation of Hydrogels Formed from Binary Alginates Elastic moduli and degradation of bulk hydrogels formed by cross-linking binary combinations of oxidized alginate (5% theoretical degree of oxidation) at a constant density of 20 mg/mL with unmodified, high $M_w$ alginate are shown in FIG. 7A and FIG. 7B. Degradation was assessed by comparing the dry mass after 4 days in-vitro to initial dry mass. The diameters of porogens formed from binary mixtures of 20 mg/mL oxidized alginate with 7.5 mg/mL unmodified alginate is shown in FIG. 7C. Porogen diameter was measured by processing fluorescent micrographs of porogens prepared from aminofluorescenin-labeled alginates.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of recruiting cells into a scaffold in vivo, comprising
   a. injecting into a subject a composite scaffold composition, wherein the composite scaffold composition:
      (i) is a polymeric scaffold composition;
      (ii) lacks macropores having a diameter of at least 20 μm at the time of injection;
      (iii) comprises a crosslinked bulk hydrogel encapsulating sacrificial porogen hydrogel micro-beads having a diameter between about 20 μm and about 500 μm; and
      (iv) comprises sacrificial porogen hydrogel micro-beads at a density of between 50% to 80% of the overall volume of the composite polymeric composition, and that comprise oxidized alginate or a shorter polymer than said bulk hydrogel such that the sacrificial porogen hydrogel micro-beads degrade at least 10% faster than said bulk hydrogel in situ; and
   b. allowing the sacrificial porogen hydrogel micro-beads to degrade in situ to form a network of macropores having a diameter between about 20 μm and about 500 μm in their place, and an intact hydrogel network, thereby allowing the recruitment of cells into the scaffold in vivo.

2. The method of claim 1, wherein said composite scaffold composition further comprises a chemokine.

3. The method of claim 2, wherein said chemokine comprises granulocyte/macrophage colony stimulating factor (GM-CSF).

4. The method of claim 1, wherein said composite scaffold composition further comprises a programming factor.

5. The method of claim 4, wherein said programming factor comprises a condensed oligonucleotide.

6. The method of claim 5, wherein said condensed oligonucleotide comprises CpG or plasmid DNA.

7. The method of claim 1, wherein said composite scaffold composition further comprises a tumor antigen.

8. The method of claim 1, wherein said cells migrate into macropores of said composite scaffold composition.

9. The method of claim 8, wherein said cells comprise lymphocytes or antigen presenting cells.

10. The method of claim 9, wherein said antigen presenting cells comprise dendritic cells.

11. The method of claim 1, wherein said sacrificial porogen hydrogel micro-beads comprise oxidized alginate.

12. The method of claim 11, wherein said sacrificial porogen hydrogel micro-beads comprise 3-7.5% oxidized alginate.

13. The method of claim 1, wherein said sacrificial porogen hydrogel micro-beads comprise alginate dialdehyde.

14. The method of claim 1, wherein said sacrificial porogen hydrogel micro-beads comprise 20 mg/mL oxidized alginate and 7.5 mg/mL unmodified alginate.

15. The method of claim 1, wherein said composite scaffold composition further comprises a bioactive factor selected from the group consisting of vascular endothelial growth factor (VEGF), acidic fibroblast growth factor (aFGF), basic fibroblast growth factor (bFGF), placenta growth factor (PlGF), platelet derived growth factor (PDGF), leptin, hematopoietic growth factor (HGF), VEGF receptor-1 (VEGFR-1), VEGFR-2, a member of the bone morphogenetic protein (BMP) family, granulocyte/macrophage colony stimulating factor (GM-CSF), FMS-like tyrosine kinase 3 ligand (Flt3 ligand), hepatocyte growth factor, stromal derived factor 1 (SDF-1), insulin like growth factor (IGF), anti-VEGF antibody, anti-aFGF antibody, anti-bFGF antibody, anti-PlGF antibody, anti-leptin antibody, anti-HGF antibody, anti-VEGFR-1 antibody, antiVEGFR-2 antibody, anti-PDGF antibody, anti-BMP antibody, anti-Flt3 ligand, and anti-IGF antibody.

16. The method of claim 1, wherein said sacrificial porogen hydrogel micro-beads or said bulk hydrogel comprise an isolated cell.

17. The method of claim 16, wherein said isolated cell is a mesenchymal stem cell, a myoblast, a vascular progenitor cell, a differentiated cell derived from an embryonic stem cell or an induced pluripotent stem cell, an induced pluripotent cell, or a cell that was directly reprogrammed from a fibroblast to a differentiated state.

18. The method of claim 1, wherein said sacrificial porogen hydrogel micro-beads comprise an elastic modulus of between 20 kPa and 60 kPa.

19. The method of claim 1, wherein said bulk hydrogel comprises a peptide comprising an amino acid sequence of PHSRN (SEQ ID NO: 1), DGEA (SEQ ID NO: 2), or RGD.

20. The method of claim 1, wherein said bulk hydrogel comprises a density of RGD peptides from 2 to 10 peptides per alginate polymer chain.

21. The method of claim 1, wherein said bulk hydrogel comprises an initial elastic modulus of at least 40 kPa.

22. The method of claim 1, wherein said composite scaffold composition promotes bone or cartilage repair, regeneration, or formation.

23. The method of claim 22, wherein said composite scaffold composition further comprises a bioactive factor selected from the group consisting of BMP-2, BMP-4, and RunX.

24. The method of claim 22, wherein said sacrificial porogen hydrogel micro-beads or said bulk hydrogel comprise an isolated bone cell selected from the group consisting of an osteoblast, an osteocyte, an osteoclast, and an osteoprogenitor.

25. The method of claim 22, wherein said sacrificial porogen hydrogel micro-beads or said bulk hydrogel comprise an isolated cartilage cell, wherein said isolated cartilage cell comprises a chondroblast.

26. The method of claim 24, wherein said isolated bone cell is an autologous or allogenic cell.

27. The method of claim 1, wherein said composite scaffold composition promotes muscle repair, regeneration, or formation.

28. The method of claim 27, wherein said composite scaffold composition further comprises a bioactive factor, wherein said bioactive factor comprises MyoD.

29. The method of claim 27, wherein said sacrificial porogen hydrogel micro-beads or said bulk hydrogel comprise an isolated muscle cell selected from the group consisting of a skeletal muscle cell, a cardiac muscle cell, a smooth muscle cell, and a myoprogenitor cell.

30. The method of claim 29, wherein said isolated muscle cell is an autologous or allogenic cell.

31. The method of claim 1, wherein said composite scaffold composition promotes skin repair, regeneration, or formation.

32. The method of claim 31, wherein said composite scaffold composition further comprises a bioactive factor, wherein said bioactive factor comprises FGF.

33. The method of claim 31, wherein said sacrificial porogen hydrogel micro-beads or said bulk hydrogel comprise an isolated skin cell selected from the group consisting of a fibroblast, a dermal cell, an epidermal cell, and a dermal progenitor cell.

34. The method of claim 33, wherein said isolated skin cell is an autologous cell or an allogeneic cell.

35. The method of claim 1, wherein sacrificial porogen hydrogel micro-beads are present at a density of 60% of the overall volume of the composite scaffold composition.

36. The method of claim 11, wherein at least 5% of said alginate is oxidized.

37. The method of claim 11, wherein said bulk hydrogel comprises unmodified alginate.

38. The method of claim 1, wherein the sacrificial porogen hydrogel micro-beads comprise an oxidized alginate polymer having a molecular weight from 5,000 to 500,000 Daltons (Da).

39. The method of claim 1, wherein the bulk hydrogel comprises an alginate polysaccharide having a molecular weight from 5,000 to 500,000 Da.

40. The method of claim 1, wherein said sacrificial porogen hydrogel microbeads comprise polymers with a molecular mass of approximately 50 kDa.

41. The method of claim 1, wherein said bulk hydrogel comprises polymers with a molecular mass of approximately 250 kDa.

42. The method of claim 1, wherein dendritic cells are recruited into said macropores and programmed to be activated antigen-presenting dendritic cells to elicit an antitumor response.

43. The method of claim 1, wherein said sacrificial porogen hydrogel micro-beads and said bulk hydrogel are biodegradable.

44. The method of claim 1, wherein said macropores comprise macropores that are 50 μm to 500 μm in diameter.

45. The method of claim 1, wherein said macropores comprise macropores that are 100 μm to 500 μm in diameter.

46. The method of claim 1, wherein said macropores comprise macropores that are 50 μm to 400 μm in diameter.

47. The method of claim 1, wherein said sacrificial porogen hydrogel micro-beads comprise oxidized alginate and said bulk hydrogel comprises oxidized alginate.

48. The method of claim 47, wherein said bulk hydrogel comprises less oxidized alginate than said sacrificial porogen hydrogel micro-beads.

49. The method of claim 48, wherein said sacrificial porogen hydrogel micro-beads comprise 3-7.5% oxidized alginate.

50. The method of claim 48, wherein said sacrificial porogen hydrogel micro-beads comprise a shorter alginate polymer than said bulk hydrogel.

* * * * *